US007419984B2

(12) United States Patent
Bhatt et al.

(10) Patent No.: US 7,419,984 B2
(45) Date of Patent: Sep. 2, 2008

(54) PYRIMIDINES AND USES THEREOF

(75) Inventors: Rama Bhatt, Shoreline, WA (US);
Baoqing Gong, Shoreline, WA (US);
Feng Hong, Seattle, WA (US); Scott A Jenkins, Seattle, WA (US); J Peter Klein, Vashon, WA (US); Cory T Kohm, Seattle, WA (US); John Tulinsky, Seattle, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 312 days.

(21) Appl. No.: 10/671,070

(22) Filed: Sep. 24, 2003

(65) Prior Publication Data
US 2004/0204386 A1    Oct. 14, 2004

Related U.S. Application Data

(60) Provisional application No. 60/460,776, filed on Apr. 4, 2003, provisional application No. 60/419,694, filed on Oct. 17, 2002.

(51) Int. Cl.
C07D 239/48 (2006.01)
A61K 31/505 (2006.01)
(52) U.S. Cl. .................. 514/275; 514/256; 544/323; 544/324; 544/326; 544/328; 544/329
(58) Field of Classification Search ............... 544/323, 544/324, 326, 328, 329; 514/275, 256
See application file for complete search history.

(56) References Cited

U.S. PATENT DOCUMENTS

| 2,691,655 | A | * | 10/1954 | Hitchings et al. | ............ 544/323 |
| 3,119,823 | A | | 1/1964 | Shapiro | .................. 260/249.9 |
| 3,933,814 | A | | 1/1976 | Haberkorn et al. | .... 260/248 NS |
| 3,948,893 | A | | 4/1976 | Aichinger et al. | ..... 260/248 NS |
| 3,966,725 | A | | 6/1976 | Reisdorff et al. | ...... 260/248 NS |
| 4,219,552 | A | | 8/1980 | Haberkorn et al. | ........... 424/249 |
| 4,499,269 | A | | 2/1985 | Bennion et al. | ............. 544/198 |
| 5,102,927 | A | | 4/1992 | Rody et al. | .................. 524/100 |
| 5,260,362 | A | | 11/1993 | Rody et al. | .................. 524/100 |
| 5,545,836 | A | | 8/1996 | Reinehr et al. | .............. 544/216 |
| 5,702,717 | A | | 12/1997 | Cha et al. | .................... 424/425 |
| 5,856,331 | A | | 1/1999 | Bursten | ...................... 514/263 |
| 6,004,985 | A | | 12/1999 | Kochanny et al. | .......... 514/341 |
| 6,150,360 | A | | 11/2000 | Daeyaert et al. | ......... 514/236.2 |
| 6,150,362 | A | | 11/2000 | Henkin et al. | ............... 514/245 |
| 6,150,382 | A | | 11/2000 | Kochanny et al. | ........... 514/341 |
| 6,166,014 | A | | 12/2000 | Kochanny et al. | ........... 514/241 |
| 6,193,960 | B1 | | 2/2001 | Metzger et al. | ............... 424/59 |
| 6,288,228 | B1 | | 9/2001 | Henkin et al. | ............... 544/197 |

FOREIGN PATENT DOCUMENTS

| DE | 1200314 | 9/1965 |
| DE | 2226474 | 2/1973 |
| EP | 525 262 A1 | 2/1993 |
| FR | 1321624 | 3/1963 |
| JP | 48-28486 | 4/1973 |
| JP | 49-69688 | 7/1974 |
| SU | 274102 | 4/1970 |
| WO | WO 91/11465 | 8/1991 |
| WO | WO 00/25780 | 5/2000 |
| WO | WO 01/25220 | 4/2001 |
| WO | WO 02/12198 | * 2/2002 |
| WO | WO 02/36578 | 5/2002 |
| WO | WO 02/36586 | * 5/2002 |

OTHER PUBLICATIONS

Britten and Kohne, "Repeated Sequences in DNA," *Science* 161(3841): 529-540, Aug. 9, 1968.
Brodskii et al., "The mechanism underlying the action of secondary aromatic amine- type antioxidants and their ethers on the radiation oxidation of N-butylpropionamide and polycaproamide," *Chemical Abstracts*, Accession No. 69:3284, 1968.
Budesinsky et al., "Substituted 2,4-diamino-6-phenyl-1,3,5-triazines," *Chemical Abstracts*, Accession No. 97:6328, 1982.
Burmistrov et al., "6-Amino-4-arylamino-2-(o-hydroxyphenyl) triazines," *Chemical Abstracts*, Accession No. 61:47941, 1964.
Bursten et al., "Interleukin-1 Rapidly Stimulates Lysophosphatidate Acyltransferase and Phosphatidate Phosphohydrolase Activities in Human Mesangial Cells," *Journal of Biological Chemistry* 266(31): 20732-20743, Nov. 5, 1991.
Bursten et al., "Lipid A activation of glomerular mesangial cells: mimicry of the bioactive lipid, phosphatidic acid," *American Journal of Physiology* 262(2): C328-C338, Feb. 1992.
Chen, C. et al., "A Convenient Synthetic Method for Trisubstituted s-Triazines," *Chemical Abstracts*, Accession No. 124:146076, 1995.
Eberhardt et al., "Human Lysophosphatidic Acid Acyltransferase," *Journal of Biological Chemistry* 272(32): 20299-20305, Aug. 8, 1997.
Elkafrawy, A.F. et al., "Synthesis and reactions of some 4-aryl-2-benzylthio-1, 6-dihydro-6-thiono-1,3,5-triazines," *Chemical Abstracts*, Accession No. 115:279963, 1991.
English, D., "Phosphatidic acid: A lipid messenger involved in intracellular and extracellular signaling," *Cell Signal* 8(5): 341-347, 1996.
Fong and Engleman, "Dendritic Cells in Cancer Immunotherapy," *Annual Review of Immunology* 18: 245-273, 2000.
Hoess and Abremski, "The Cre-*lox* Recombination System," *Nucleic Acids and Molecular Biology* 4: 99-109, 1990.
Imamura et al, "Induction of in vitro tumor cell invasion of cellular monolayers by lysophosphatidic acid or phospholipase D," *Biochemical and Biophysical Research Communications* 193(2): 497-503, Jun. 15, 1993.
Kester, M., "Platelet-Activating Factor Stimulates Phosphatidic Acid Formation in Cultured Rat Mesangial Cells: Roles of Phospholipase D, Diglyceride Kinase, and De Novo Phospholipid Synthesis," *Journal of Cellular Physiology* 156: 317-325, 1993.

(Continued)

*Primary Examiner*—Deepak Rao

(57) ABSTRACT

The invention relates to pyrimidines and uses thereof, including to inhibit lysophosphatidic acid acyltransferase β (LPAAT-β) activity and/or proliferation of cells such as tumor-cells.

12 Claims, No Drawings

OTHER PUBLICATIONS

Köhler and Milstein, "Continuous cultures of fused cells secreting antibody of predefined specificity," *Nature* 256(5517): 495-497, Aug. 7, 1975.

Kume and Shimizu, "cDNA Cloning and Expression of Murine 1-Acyl-*sn*-glycerol-3-phosphate Acyltransferase," *Biochemical and Biophysical Research Communications* 237(3): 663-666, Aug. 28, 1997.

Leung et al., "Molecular Cloning of Two Alternatively Spliced Forms of Human Phosphatidic Acid Phosphatase cDNAs that Are Differentially Expressed in Normal and Tumor Cells," *DNA and Cell Biology* 17(4): 377-385, Apr. 1998.

Losman et al., "Baboon anti-idiotype antibodies mimic a carcinoembryonic antigen epitope," *Int. J. Cancer* 46(2): 310-314, Aug. 15, 1990.

Martin et al., "Increased concentrations of phosphatidate, diacylglycerol and ceramide in *ras*- and tyrosine kinase (*fps*)-transformed fibroblasts," *Oncogene* 14(13):1571-1580, Apr. 3, 1997.

Michalik, M. et al., "Synthesis of nitrogen-containing heterocycles," *Chemical Abstracts*, Accession No. 79:18680, 1973.

Miller and Rosman, "Improved Retroviral Vectors for Gene Transfer and Expression," *BioTechniques* 7(9): 980-EOA, Oct. 1989.

Moolenaar, W.H., "Lysophosphatidic Acid, a Multifunctional Phospholipid Messenger," *Journal of Biological Chemistry* 270(22): 12949-12952, Jun. 2, 1995.

Moussa, G.E.M. et al., "Some reactions on 4-aryl-2-substituted amino-1,6-dihydro-6-thioxo-1,3,5 triazines," *Chemical Abstracts*, Accession No. 113:59112, 1990.

Orlandi et al., "Cloning immunoglobulin variable domains for expression by the polymerase chain reaction," *Proc. Natl. Acad. Sci. USA* 86(10): 3833-3837, May 1989.

Pitts et al., "Rapid Synthesis of Triazine Inhibitors of Inosine Monophosphate Dehydrogenase," *Bioorganic & Medicinal Chemistry Letters* 12: 2137-2140, 2002.

Rizzo et al., "The Recruitment of Raf-1 to Membranes Is Mediated by Direct Interaction with Phosphatidic Acid and Is Independent of Association with Ras," *Journal of Biological Chemistry* 275(31): 23911-23918, Aug. 4, 2000.

Sauer, B., "Inducible Gene Targeting in Mice Using the Cre/*lox* System," *Methods: A Companion to Methods in Enzymology* 14(4): 381-392, Apr. 1998.

Schreurs et al., "Dendritic Cell-Based Vaccines: From Mouse Models to Clinical Cancer Immunotherapy," *Critical Reviews in Oncogenesis* 11(1): 1-17, 2000.

Shapiro, S.L. et al., "Guanamines. VIII. 6-(Substituted-phenyl) guanamines," *Chemical Abstracts*, Accession No. 56:60602, 1962.

Sharp et al., "Viral DNA in Transformed Cells. I. A Study of the Sequences of Adenovirus 2 DNA in a Line of Transformed Rat Cells Using Specific Fragments of the Viral Genome," *J. Mol. Biol.* 86(4): 709-726, Jul. 15, 1974.

Sluka et al., "2,4-diamino-6-phenyl-1,3,5-triazines," *Collection Czechoslov. Chem. Commun.* 43: 1639-1646, 1978.

Stamps et al., "A human cDNA sequence with homology to non-mammalian lysophosphatidic acid acyltransferases," *Biochemical Journal* 326:455-461, Sep. 1, 1997.

Sutton, W.D., "A crude nuclease preparation suitable for use in DNA reassociation experiments," *Biochimica et Biophysica Acta* 240(4): 522-531, Jul. 29, 1971.

West et al., "Cloning and Expression of Two Human Lysophosphatidic Acid Acyltransferase cDNAs That Enhance Cytokine-Induced Signaling Responses in Cells," *DNA and Cell Biology* 16(6): 691-701, Jun. 1997.

Wetmur and Davidson, "Kinetics of Renaturation of DNA," *Journal of Molecular Biology* 31(3): 349-370, Feb. 14, 1968.

Xu et al, "Lysophospholipids activate ovarian and breast cancer cells," *Biochemical Journal* 309: 933-940, Aug. 1, 1995.

Yuki, Y. et al., "Preparation of amino-s-triazines with amino-or nitrophenyl groups," *Chemical Abstracts*, Accession No. 75:151765, 1971.

* cited by examiner

PYRIMIDINES AND USES THEREOF

CROSS-REFERENCE TO RELATED APPLICATIONS

This application claims the benefit of U.S. Provisional Application No. 60/419,694, filed Oct. 17, 2002 and 60/460,776, filed Apr. 4, 2003, which applications are incorporated by reference herein in their entirety.

BACKGROUND OF THE INVENTION

1. Field of the Invention

The invention is in the field of organic and medicinal chemistry. In particular, the invention relates to pyrimidines and uses thereof, such as inhibiting the activity of lysophosphatidic acid acyltransferase β (LPAAT-β) activity and/or inhibiting the proliferation of a cell (e.g., tumor cell).

2. Description of the Related Art

Lysophosphatidic acid acyltransferase (LPAAT) catalyzes the acylation of lysophosphatidic acid (LPA) to phosphatidic acid. LPA is the simplest glycerophospho-lipid, consisting of a glycerol molecule, a phosphate group, and a fatty acyl chain. LPAAT adds a second fatty acyl chain to LPA, producing phosphatidic acid (PA). PA is the precursor molecule for certain phosphoglycerides, such as phosphatidylinositol, and diacylglycerols, which are necessary for the production of other phosphoglycerides, such as phosphatidylcholine, and for triacylglycerols, which are essential biological fuel molecules.

In addition to being a crucial precursor molecule in biosynthetic reactions, LPA has been added to the list of intercellular lipid messenger molecules. LPA interacts with G protein-coupled receptors, coupling to various independent effector pathways including inhibition of adenylate cyclase, stimulation of phospholipase C, activation of MAP kinases, and activation of the small GTP-binding proteins Ras and Rho (Moolenaar, *J. Biol. Chem.* 28:1294 (1995)). The physiological effects of LPA have not been fully characterized as yet. However, one of the physiological effects that is known is that LPA promotes the growth and invasion of tumor cells. It has been shown that the addition of LPA to ovarian or breast cancer cell lines induces cell proliferation, increases intracellular calcium levels, and activates MAP kinase (Xu et al., *Biochem. J.* 309:933 (1995)). In addition, LPA has been shown to induce MM1 tumor cells to invade cultured mesothelial cell monolayers (Imamura et al., *Biochem. Biophys. Res. Comm.* 193:497 (1993)).

Like LPA, PA is also a messenger molecule. PA is a key messenger in a common signaling pathway activated by proinflammatory mediators such as interleukin-1β, tumor necrosis factor αx, platelet activating factor, and lipid A (Bursten et al., *Am. J. Physiol.* 262:C328 (1992); Bursten et al., *J. Biol. Chem.* 255:20732 (1991); Kester, *J. Cell Physiol.* 156:317 (1993)). PA has been implicated in mitogenesis of several cell lines (English, Cell Signal 8:341 (1996)). PA level has been found to be increased in either ras or fps transformed cell lines compared to the parental Rat2 fibroblast cell line (Martin et al., *Oncogene* 14:1571 (1997)). Activation of Raf-1, an essential component of the MAPK signaling cascade, by extracellular signals is initiated by association with intracellular membranes. Recruitment of Raf 1 to membranes has been reported to be mediated by direct association with phosphatidic acid (Rizzo et al., *J. Biol. Chem.* 275:23911-8 (2000)). Thus, LPAAT, as an enzyme that regulates PA content in cells, may play a role in cancer, and may also mediate inflammatory responses to various proinflammatory agents.

LPAAT exists in a LPAAT-α form and a LPAAT-β form. Northern blot analysis shows that LPAAT-(α is expressed in all human tissues tested with the highest expression level found in skeletal muscle (West et al., *DNA Cell Biol.* 16:691 (1997)). The uniformity of LPAAT-(α expression has also been found in additional tissues such as prostate, testis, ovary, small intestine, and colon (Stamps et al. *Biochem. J.* 326:455 (1997)) as well as in mouse tissues (Kume et al., *Biochem. Biophys. Res. Commun.* 237:663 (1997)). A 2 kb and a 1.3 kb forms, possibly due to alternative utilization of polyadenylation signals at the 3'-UTR, have been found in murine LPAAT-α mRNA (Kume et al., *Biochem. Biophys. Res. Commun* 237:663 (1997)), whereas only one major human LPAAT-α mRNA of 2 kb in size has been detected by Northern analysis (West et al., *DNA Cell Biol.* 16:691 (1997); Stamps et al., *Biochem. J.* 326:455 (1997)).

In contrast, LPAAT-β demonstrates a distinct tissue distribution of mRNA expression (West et al., *DNA Cell Biol.* 16:691 (1997)). LPAAT-β is most highly expressed in liver and heart tissues. LPAAT-β is also expressed at moderate levels in pancreas, lung, skeletal muscle, kidney, spleen, and bone marrow; and at low levels in thymus, brain and placenta. This differential pattern of LPAAT-β expression has been confirmed independently (Eberhardt et al., *J. Biol. Chem.* 272:20299 (1997)) with the only discrepancy being that high level, instead of moderate level, of LPAAT-β has been detected in pancreas, possibly due to slight lot variations in commercial RNA blots (Clontech, Palo Alto, Calif.). In addition, moderate LPAAT-β expression has been found in prostate, testis, ovary, small intestine, and colon with the small intestine containing relatively higher amounts (Eberhardt et al, *J. Biol. Chem.* 272:20299 (1997)). Within various brain sections, high expression has been found in the subthalamic nucleus and spinal cord; and least in the cerebellum, caudate nucleus, corpus callosum, and hippocampus. LPAAT-β can also be detected in myeloid cell lines THP-1, HL-60, and U937 with the mRNA levels remaining the same with or without phorbal-ester treatment. The size difference between human LPAAT-α and LPAAT-β mRNA is consistent with the sequence data, in which LPAAT-(α has a longer 3'-UTR. The differential tissue expression pattern of LPAAT-α and LPAAT-β mRNA would suggest these two genes are regulated differently and are likely to have independent functions. Therefore, a desirable feature in compounds that inhibit LPAAT activity is that they are specific in inhibiting one isoform of the enzyme over the other (i.e., LPAAT-β over LPAAT-α).

LPAAT-β mRNA has been found to be elevated in tumor tissues (e.g., uterus, fallopian tube, and ovary), as compared to its expression in the corresponding normal tissues. However, no significant difference was found in LPAAT-α mRNA level between the various tumor tissues and the normal adjacent tissues. In two of the tumor tissues (fallopian tube and ovary) where LPAAT-α mRNA was elevated, PAP2-α mRNA expression was found to be suppressed, as it was also in tumors of the colon, rectum, and breast. Thus, LPAAT-β (rather than LPAAT-α) appears to be a relevant target for inhibition.

There is a need in the art for improved compositions and methods. The present invention fills this need, and further provides other related advantages.

BRIEF SUMMARY OF THE INVENTION

Briefly stated, the present invention provides a variety of compounds and uses thereof. More specifically, the compounds of the present invention are pyrimidines that possess aromatic substituents which are directly or indirectly attached to two non-adjacent carbons of the pyrimidine ring. The compounds are generally of the formula:

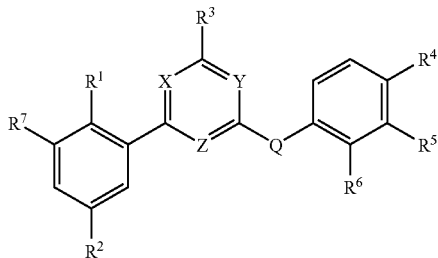

where $R^1$-$R^7$ are hydrogen or non-hydrogen substituents, Q is a heteroatom or heteroatom attached to one or more methylene groups, and two of X, Y and Z are N with the third being CH or a substituted C. In preferred embodiments:

X, Y and Z are N, CH or CR where R is alkyl, alkoxy, Cl, Br, $NH_2$, NHR' or NR'R" where R' and R" independently are alkyl;

Q is NR, RN—$(CH_2)_n$, $(CH_2)_n$—NR, O, O—$(CH_2)_n$, $(CH_2)_n$—O, S, S—$(CH_2)_n$ or $(CH_2)_n$—S, where n is 1-10 and R is H or alkyl;

$R^1$ is H, OH, alkyl, alkoxy, Cl, F, Br, $CR_3$ where $R_3$ is $Cl_3$, $F_3$ or $Br_3$, $NH_2$, NHR or NRR' where R and R' independently are alkyl;

$R^2$ and $R^7$ are independently H, OH, alkyl, alkoxy, Cl, F, Br, I or $CR_3$ where $R_3$ is $Cl_3$, $F_3$ or $Br_3$;

$R^3$ is H, alkyl, alkoxy, Cl, $CCl_3$, $NH_2$, NHR or NRR' where R and R' independently are alkyl or acyl;

$R^4$, $R^5$ and $R^6$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl, heterocycle, $N^+$(=O)$O^-$, C=N, $N_3$, $B(OH)_2$, SH, SR or $S(=O)_2R$ where R is alkyl, $NH_2$, NHR or NRR' where R and R' independently are alkyl, or $R^4$ and $R^5$ or $R^5$ and $R^6$ are taken together with the benzene ring to form a heterocycle;

and with the proviso that two of X, Y and Z are N.

A compound or salt thereof as described above may be combined with a pharmaceutical carrier or diluent to form a pharmaceutical composition of the present invention.

A compound, salt thereof or pharmaceutical composition of the present invention may be used in one or more methods. In one method, the activity of LPAAT-β may be reduced by the step comprising contacting LPAAT-β with a compound, salt thereof or pharmaceutical composition of the present invention in an amount effective to reduce LPAAT-β activity. In another method, the proliferation of a cell in which the activity of LPAAT-β is required for the proliferation of the cell may be inhibited by the step comprising contacting LPAAT-β with a compound, salt thereof or pharmaceutical composition of the present invention in an amount effective to inhibit the proliferation of the cell. In a further method, the treatment of a cancer in which LPAAT-β activity is associated may be effected by the step comprising administering to an animal in need a compound, salt thereof or pharmaceutical composition of the present invention in an amount effective to treat the cancer.

Also provided is a coated medical device for inhibiting the proliferation of a cell in which the activity of LPAAT-β is required for the proliferation of the cell comprising a medical device coated with a compound, salt thereof or pharmaceutical composition of the present invention.

These and other aspects of the present invention will become evident upon reference to the following detailed description.

DETAILED DESCRIPTION OF THE INVENTION

Prior to setting forth the invention, it may be helpful to an understanding thereof to set forth definitions of certain terms to be used hereinafter.

In the present description, the term "alkyl" refers to straight- or branched-chain hydrocarbons having from 1 to 10 carbon atoms and more preferably 1 to 8 carbon atoms which include, by way of example, methyl, ethyl, n-propyl, i-propyl, n-butyl, t-butyl and the like. The alkyl group may be substituted or unsubstituted. When substituted, the substituted group(s) is preferably one or more independently selected from alkyl, cycloalkyl, heteroalicyclic, aryl, heteroaryl, haloalkyl, halo, hydroxy, alkoxy, mercapto, cyano, sulfonamidyl, aminosulfonyl, acyl, acyloxy, substituted imino and substituted amino.

"Alkenyl" includes monovalent hydrocarbon radicals having straight, cyclic, or branched moieties, and combinations thereof which comprise at least one carbon-carbon double bond. The alkenyl group may be substituted or unsubstituted. When substituted, the substituted group(s) is preferably one or more independently selected from alkyl, acyl, cycloalkyl, heteroalicyclic, aryl, haloalkyl, alkoxy and substituted amino.

"Alkoxy" refers to the group "—O-alkyl" which includes, by way of example, methoxy, ethoxy, n-propoxy, i-propoxy, n-butoxy, t-butoxy and the like. It further refers to the group "—O-alkyl-W-alkyl" where W is O or N; for example, —O—$(CH_2)_n$—W—$(CH_2)_m$ where n and m are independently 1-10. The alkoxy group may be unsubstituted or substituted, for example with an alkyl, cycloalkyl, alkenyl, acyl, aryl or heterocycle group(s).

"Substituted amino" denotes the group —NRR, wherein each R group is independently selected from hydrogen, hydroxy, acyl, alkyl, cycloalkyl, aryl, or the R groups can be joined together with the nitrogen to form a heterocyclic ring (e.g., piperidine, piperazine, or a morpholine ring).

"Substituted imino" denotes the group =NR, wherein R is preferably selected from hydrogen, hydroxy, alkyl and acyl.

"Aryl" refers to an unsaturated aromatic carbocyclic group of 6 to 14 carbon atoms having a single ring (e.g., phenyl) or multiple condensed rings (e.g., naphthyl or anthryl). The aryl group may be unsubstituted or substituted; in the latter case, the substituent or substituents preferably are selected independently from alkyl, aryl, haloalkyl, halo, hydroxy, alkoxy, mercapto, cyano, sulfonamidyl, aminosulfonyl, acyl, acyloxy, nitro, and substituted amino.

"Heterocycle" includes "heteroaryl" and "heteroalicyclic". Examples of heterocycles include oxazole, piperidine, piperazine and morpholine.

"Heteroaryl" is a monocyclic or fused ring (i.e., rings which share an adjacent pair of atoms) group having in the ring(s) one or more atoms selected preferably from nitrogen, oxygen and sulfur and, in addition, having a completely conjugated π-electron system. Exemplary heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more independently selected from alkyl, aryl, haloalkyl, halo, hydroxy, alkoxy, mercapto, cyano, sulfonamidyl, aminosulfonyl, acyl, acyloxy, nitro and substituted amino.

"Cycloalkyl" encompasses cyclic alkyl groups that contain between 3 and 8 carbon atoms and have a single cyclic ring, illustrated by cyclopropyl, cyclobutyl, cyclopentyl, and cyclooctyl. The cycloalkyl ring may be substituted or unsubstituted. Again, a substituted cycloalkyl ring carries one or more substituent groups, independently selected preferably from alkyl, aryl, haloalkyl, halo, hydroxy, alkoxy, mercapto, cyano, sulfonamidyl, aminosulfonyl, acyl, acyloxy, vitro, and substituted amino.

"Heteroalicyclic" refers to a monocyclic or fused ring group having in the ring(s) one or more atoms selected preferably from nitrogen, oxygen and sulfur. The rings may also have one or more double bonds. However, the rings do not have a completely conjugated π-electron system. The heteroalicyclic ring may be substituted or unsubstituted. When substituted, the substituted group(s) preferably are selected independently from alkyl, aryl, haloalkyl, halo, hydroxy, alkoxy, mercapto, cyano, sulfonamidyl, aminosulfonyl, acyl, acyloxy, vitro, and substituted amino.

"Halogen" or "halo" refers to fluoro, chloro, bromo, iodo.

"Acyl" containing group" refers to the C(O)—R" group, where R" is selected preferably from hydrogen, hydroxy, alkyl, haloalkyl, cycloalkyl, substituted amino, aryl optionally substituted with one or more alkyl, haloalkyl, alkoxy, halo and substituted amino groups, heteroaryl (bonded through a ring carbon) optionally substituted with one or more alkyl, haloalkyl, alkoxy, halo and substituted amino groups and heteroalicyclic (bonded through a ring carbon) optionally substituted with one or more alkyl, haloalkyl, alkoxy, halo and substituted amino groups. Acyl containing groups include aldehydes, ketones, acids, acid halides, esters and amides. Preferred acyl containing groups are carboxy groups, e.g., acids and esters. Esters include amino acid ester derivatives. The acyl containing group may be attached to a compound's backbone at either end of the acyl group, i.e., via the C or the R". Where the acyl containing group is attached via the R", then C will bear another substituent, such as hydrogen or alkyl.

The phrase "physiologically acceptable salt" refers to those salts that retain the biological effectiveness and properties of the particular compound. Physiologically acceptable salts are often useful because they may have improved stability and/or solubility in pharmaceutical compositions over the free base form or free acid form of the compound. A physiologically acceptable salt may be obtained by reaction of a free base with an inorganic acid such as hydrochloric acid, hydrobromic acid, nitric acid, phosphoric acid, sulfuric acid, and perchloric acid and the like, or with an organic acid such as acetic acid, oxalic acid, malic acid, maleic acid, methanesulfonic acid, ethanesulfonic acid, p-toluenesulfonic acid, salicylic acid, tartaric acid, citric acid, succinic acid or malonic acid, and the like. A physiologically acceptable salt may also be obtained by reaction of a free acid with a base such as sodium, potassium or lithium hydroxide, bicarbonate or carbonate, and the like.

As noted above, the present invention provides pyrimidines, physiologically acceptable salts thereof and uses thereof. The pyrimidines possess aromatic substituents that are directly or indirectly attached to two non-adjacent carbons of the pyrimidine ring.

The compounds are generally of the formula:

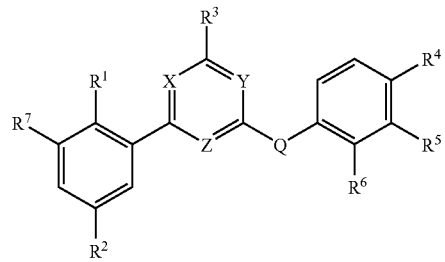

where $R^1$-$R^7$ are hydrogen or non-hydrogen substituents, Q is a heteroatom or heteroatom attached to one or more methylene groups, and two of X, Y and Z are N with the third being CH or a substituted C. The requirement that two of X, Y and Z are N is consistent with the compounds including a pyrimidine ring.

Preferred embodiments include the following selections for the general formula above. Preferred embodiments include where X, Y and Z are N, CH or CR. R of CR is alkyl, alkoxy, halo (preferably Cl or Br), $NH_2$, NHR' or NR'R" where R' and R" independently are alkyl. Particularly preferred is where X and Y are N.

Preferred embodiments include where Q is a heteroatom (preferably N, O or S) and may be attached to one or more methylene groups to provide additional spacing between the pyrimidine ring and the phenyl ring possessing $R^4$, $R^5$ and/or $R^6$. Q may be NR where R is H or alkyl. Where there are one or more methylene groups, the heteroatom may be oriented such that it is attached directly to the pyrimidine ring or attached directly to the phenyl ring possessing $R^4$, $R^5$ and/or $R^6$. For example, Q may be RN— $(CH_2)_n$, $(CH_2)_n$—NR, O—$(CH_2)_n$, $(CH_2)$, —O, S—$(CH_2)$, or $(CH_2)_n$—S, where n is typically 1-10 and R is H or alkyl. Particularly preferred is where Q is NH.

Preferred embodiments include where $R^1$ is H, OH, alkyl, alkoxy, halogen (preferably Cl, F or Br), $CR_3$, $NH_2$, NHR or NRR'. $R_3$ of $CR_3$ is (halo)$_3$, preferably $Cl_3$, $F_3$ or $Br_3$. R and R' of NHR and NRR' are independently alkyl. The term "independently," as used throughout, refers to independent selection of a group, but does not exclude the possibility that two groups are identical. For example, the alkyl group of R and R' of NRR' may be the same or different. Particularly preferred is where $R^1$ is alkyl, alkoxy or Cl.

Preferred embodiments include where $R^2$ and $R^7$ are independently H, OH, alkyl, alkoxy, halogen (preferably Cl, F or Br), or $CR_3$. $R_3$ of $CR_3$ is (halo)$_3$, preferably $Cl_3$, $F_3$ or $Br_3$. Particularly preferred is where $R^2$ is Cl or Br.

Preferred embodiments include where $R^3$ is H, alkyl, alkoxy, halogen (preferably Cl), $CR_3$, $NH_2$, NHR or NRR'. $R_3$ of $CR_3$ is (halo)$_3$, preferably $Cl_3$. R and R' of NHR and NRR' are independently alkyl or acyl. Particularly preferred is where $R^3$ is alkyl or $NH_2$.

Preferred embodiments include where $R^4$, $R^5$ and $R^6$ are independently H, OH, alkyl, alkenyl, alkynyl, alkoxy, $(CH_2)_n$—OR, halogen (preferably Cl, F or Br), $CR_3$, acyl, heterocycle, $N^+(=O)O^-$, C≡N, $N_3$, $B(OH)_2$, SH, SR, $S(=O)_2R$, $NH_2$, NHR or NRR'. R of $(CH_2)_n$—OR is H or alkyl, and n is typically 1-10, with $CH_2$—OH and $(CH_2)_2$—OH preferred. $R_3$ of $CR_3$ is (halo)$_3$, preferably $Cl_3$, $F_3$ or $Br_3$. A preferred heterocycle is oxazol. A preferred acyl is phenone (so forms benzophenone when taken with the benzene ring to which it is attached) or ester, such as an amino acid ester derivative. R of SR and S(=O)$_2$R is alkyl. R and R' of NHR and NRR' are independently alkyl. Particularly preferred is where R$^4$ or R$^5$ or R$^6$ is Cl, Br, (CH$_2$)$_2$—OH, N$^+$(=O)O$^-$, C≡N, or C(=O)R wherein R is alkyl or alkoxy. Also preferred is where R$^4$ or R$^5$ or R$^6$ is a non-polar substituent, e.g., alkyl. Alternatively, R$^4$ and R$^5$ (or R$^5$ and R$^6$) may be taken together with the benzene ring to form a heterocycle. A preferred heterocycle is indazolyl, benzotriazolyl, indolyl, benzothiazolyl, benzimidazolyl or benzodioxolyl. Particularly preferred is where R$^4$ and R$^5$ (or R$^5$ and R$^6$) are taken together with the benzene ring to form indazole.

Particularly preferred compounds of the present invention are shown in Table 1 of Example 193 below, and physiologically acceptable salts thereof.

It may be advantageous for certain uses to enhance the solubility and/or bioavailability of one or more of the compounds of the present invention. This may be accomplished, for example, by the addition of one or more substituents to the compound. For example, the addition of hydrophilic groups, such as hydroxyl groups, may be advantageous. Other substituents for enhancing solubility and/or bioavailability include amino acids (e.g., polyglutamate or polylysine), dipeptides, polymers (e.g., PEG or POG), monocarboxylic acids (e.g., hemi-succinate), and esters. Any group that enhances solubility and/or bioavailability of a compound of the present invention may be used, provided that the group does not significantly impair the relevant biological property of the compound, e.g., as an inhibitor of LPAAT-β activity.

It may be advantageous for certain uses to prepare a compound (or physiologically acceptable salt thereof) as a "prodrug." As used herein, the term "compound" encompasses a prodrug form of the parent compound. "Prodrug" herein refers to a chemical substance that is converted into the parent compound in vivo. Prodrugs often are useful because, in some situations, they may be easier to administer than the parent compound. They may, for instance, be bioavailable by oral administration whereas the parent compound is not. The prodrug may also have improved solubility in pharmaceutical compositions over the parent compound. An example of a prodrug would be a parent compound of the present invention which is administered as an ester (the "prodrug") to facilitate transmittal across a cell membrane where water solubility is detrimental to mobility. The ester is then metabolically hydrolyzed to the carboxylic acid, the active entity, once inside the cell where water solubility is beneficial. Such a prodrug is generally inactive (or less active) until converted to the active form.

Pharmaceutical compositions of the compounds and the physiologically acceptable salts thereof are preferred embodiments of this invention. Pharmaceutical compositions of the compounds of the present invention (i.e., compounds and salts thereof as described above) may be manufactured by processes well known in the art; e.g., by means of conventional mixing, dissolving, granulating, dragee-making, levigating, emulsifying, encapsulating, entrapping or lyophilizing processes.

Pharmaceutical compositions may be formulated in a conventional manner using one or more physiologically acceptable carriers or diluents. Proper formulation is generally dependent upon the route of administration chosen. The pyrimidines of the present invention may be formulated such that the formulation comprises a single pyrimidine or a mixture of two or more pyrimidines described herein. Alternatively, one or more pyrimidines may be formulated with one or more other agents which are active for a general or specific disease, disorder or condition.

For injection, the compounds of the invention may be formulated as sterile aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with physiologically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be made with the use of a solid carrier or diluent, optionally grinding the resulting mixture, and processing the mixture of granules, after adding suitable auxiliaries, if desired, to obtain tablets or dragee cores. Suitable carriers or diluents are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the embodiments of the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoro-ethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical compositions for parenteral administration include sterile aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation (see, for example, U.S. Pat. No. 5,702,717 for a biodegradable depot for the delivery of a drug). Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The pharmaceutical compositions herein also may comprise suitable solid or gel phase carriers or diluents. Examples of such carriers or diluents include but are not limited to calcium carbonate, calcium phosphate, various sugars, starches, cellulose derivatives, gelatin, and polymers such as polyethylene glycols.

The compounds of the invention may be provided as physiologically acceptable salts wherein the claimed compound may form the negatively or the positively charged species. Examples of salts in which the compound forms the positively charged moiety include quaternary ammonium salts such as the hydrochloride, sulfate, carbonate, lactate, tartarate, maleate, succinate, etc. formed by the reaction of an amino group with the appropriate acid.

As noted above, LPAAT-β appears to play a role in various cellular pathways that have a connection to various diseases, disorders or conditions. The disclosure of the present invention shows unexpectedly that the pyrimidines set forth above inhibit the activity of LPAAT-β. This surprising inhibition is also specific for LPAAT-β, as the compounds tested showed weak to no inhibitory activity for LPAAT-α. In particular, none of the compounds tested had an $IC_{50}$ of less than 40 µM for LPAAT-α. In one use of the compounds of the present invention, the activity of LPAAT-β is reduced. The method comprises contacting LPAAT-β with a compound or salt thereof or composition of the present invention in an amount effective to reduce the LPAAT-β activity. The LPAAT-β to be contacted may reside in a cell-free preparation or in intact cells, including cells within an animal.

In the context of the present invention, the term "animal" refers to any animal, including humans and other primates, rodents (e.g., mice, rats, and guinea pigs), lagamorphs (e.g., rabbits), bovines (e.g., cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc), as well as feral or wild animals, including such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term. A preferred animal within the present invention is a mammal, with humans particularly preferred.

In another use of the compounds of the present invention, the proliferation of a cell (in which the activity of LPAAT-β is required for the proliferation of the cell) is inhibited. The method comprises contacting the cell with a compound or salt thereof or composition of the present invention in an amount effective to inhibit the proliferation of the cell. The cell to be contacted may be in vitro or in vivo in an animal. An example of a cell whose proliferation it is desirable to inhibit is a tumor cell. However, there are other diseases, disorders and conditions with cell types other than tumor cells for which it may be desirable to inhibit proliferation of the cell. In the context of the present invention, the term "inhibiting" refers to both total inhibition and partial inhibition (i.e., the inhibition need not be 100%).

In another use of the compounds of the present invention, a cancer (in which LPAAT activity is associated) is treated. The method comprises administering to an animal in need, a compound or salt thereof or composition of the present invention in an amount effective to treat the cancer. In the context of the present invention, the term "treating a cancer" refers to any of a variety of positive effects from the treatment, including preventing the spread of a tumor, arresting tumor growth at a primary site, eradicating the tumor, relieving a symptom associated with the cancer, or prolonging the survival time of the animal treated. For example, as used herein, treating a cancer may have the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, (4) relieving to some extent (or, preferably, eliminating) one or more symptoms associated with the cancer, and/or (5) prolonging the survival time of the recipient. In addition, treatment further includes preventing tumor occurrence or recurrence. The method may further comprise inclusion of one or more other agents for treating a cancer. Alternatively, the method may be used in conjunction with one or more other cancer therapies, such as radiation, surgery or other chemotherapy.

Suitable routes of administration may include, without limitation, oral, rectal, transmucosal or intestinal administration or intramuscular, subcutaneous, intramedullary, intrathecal, direct intraventricular, intravenous, intraperitoneal or intranasal injections.

Alternately, one may administer the compound or composition in a local rather than systemic manner, for example, via injection of the compound or composition directly into a solid tumor, often in a depot or sustained release formulation.

Furthermore, one may administer the compound or composition in a targeted drug delivery system, for example, in a liposome coated with tumor-specific antibody. The liposomes will be targeted to and taken up selectively by the tumor.

Compounds and compositions suitable for use in the methods of the present invention are compounds and compositions wherein the active ingredients are contained in an amount effective to achieve its intended purpose. Determination of an effective amount is well within the capability of one of ordinary skill in the art, especially in light of the detailed disclosure provided herein.

For any compound or composition used in the methods of the invention, the effective amount or dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of LPAAT-β activity). Such information can be used to more accurately determine useful doses in humans.

Toxicity and therapeutic efficacy of the compounds described herein can be determined by standard pharmaceutical procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl, et al., in "The Pharmacological Basis of Therapeutics," (1975), Chapter 1, pp. 1).

Dosage amount and interval may be adjusted individually to provide plasma levels of the active moiety which are sufficient to maintain LPAAT-β inhibitory effects, or minimal effective concentration (MEC). The MEC will vary for each compound but can be estimated from in vitro data; e.g., the concentration necessary to achieve 50-90% inhibition of LPAAT-β using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

The amount of compound or composition administered will, of course, be dependent on the subject being treated, on the subject's weight, the severity of the affliction, the manner of administration and the judgment of the prescribing physician. An exemplary systemic daily dosage is about 5 to about 200 mg/kg of body weight. Normally, from about 10 to about 100 mg/kg of body weight of the compounds of the present invention, in one or more dosages per day, is effective to obtain the desired results. One of ordinary skill in the art can determine the optimal dosages and concentrations of the compounds of the preferred embodiments of the present invention with only routine experimentation.

The compounds of the present invention when used are substantially pure and preferably sterile. The phrase "substantially pure" encompasses compounds created by chemical synthesis or compounds substantially free of chemicals which may accompany the compounds in the natural state, as evidenced by thin layer chromatography (TLC) or high performance liquid chromatography (HPLC).

A compound or salt thereof of the present invention, or pharmaceutical composition of either, may be used to coat a medical device. A variety of medical devices, such as a stent, may be coated. The medical device may be composed of a bioadsorbable and biodegradable material. Due to the antiproliferative properties of the compounds of the present invention, a stent or other medical device that is coated with such a compound or salt thereof or pharmaceutical composition of either may be used for inhibiting the proliferation of a cell. The coated medical devices of the present invention may be used in a variety of ways. A preferred use is to inhibit the proliferation of tumor cells.

The following examples are offered by way of illustration and not by way of limitation.

EXAMPLES

Example 1

6-(5-Chloro-2-methoxy-phenyl)-N*4*-p-tolyl-pyrimidine-2,4-diamine

A mixture of 4,6-dichloro-pyrimidin-2-yl-amine (3.3 g, 20 mmol), p-tolylamine (3.4 g, 32 mmol) and N,N-diisopropylethylamine (12 ml) in ethanol (150 ml) was heated under reflux for 40 hours. After cooling to room temperature, filtration provided 6-chloro-N*4*-p-tolyl-pyrimidine-2,4-diamine (2.8 g, 60% yield) as a white solid.

To a mixture of 6-chloro-N*4*-p-tolyl-pyrimidine-2,4-diamine (2.8 g, 11.9 mmol), 5-chloro-2-methoxy-phenyl boronic acid (3.96 g, 21.5 mmol), palladium (II) acetate (0.2 g, 0.9 mmol) and triphenylphosphine (0.47 g, 1.8 mmol) was added a solution of sodium carbonate (6.36 g, 60 mmol) in water (20 ml) followed by glyme (100 ml). The mixture was stirred under an argon atmosphere at 90-95° C. for 18 hours. Filtration and concentration of the filtrate yielded a residue which was purified by flash chromatography on silica gel eluting with ethyl acetate-hexane (1:3) to provide the title compound (3.48 g, 86% yield) as a white powder. $^1$H NMR (DMSO-$d_6$) δ 2.27 (s, 3H, $CH_3$), 3.88 (s, 3H, $CH_3$), 6.27 (s, 2H, $NH_2$), 6.72 (s, 1H, Ar), 7.10 (d, 2H, J=8.3 Hz, Ar), 7.16 (d, 1H, J=8.9 Hz, Ar), 7.44 (dd, 1H, J=8.9 Hz, J=2.8 Hz, Ar), 7.63 (d, 2H, J-8.3 Hz, Ar), 7.92 (d, 1H, J=2.8 Hz, Ar), 9.10 (s, 1H, NH).

Example 2

6-(5-Chloro-2-methoxy-phenyl)-N*4*-(4-chloro-phenyl)-pyrimidine-2,4-diamine

A mixture of 4,6-dichloro-pyrimidin-2-yl-amine (2.0 g, 12.2 mmol), 4-chloro-phenylanmine (1.62 g, 12.2 mmol), and N,N-diisopropylethylamine (4.25 ml) in ethanol (75 ml) was heated under reflux for 40 hours. Additional portions of N,N-diisopropylethylamine (2 ml) and ethanol (20 ml) were added and the reaction mixture was heated under reflux for 48 hours. A cloudy mixture was obtained. Filtration and concentration of the filtrate yielded a residue which was purified by flash chromatography on silica gel eluting with ethyl acetate-hexane (1:3) to provide 6-chloro-N*4*-(4-chloro-phenyl)-pyrimidine-2,4-diamine (0.59 g, 19% yield) as white fluffy solid.

To a mixture of 6-chloro-N*4*-(4-chloro-phenyl)-pyrimidine-2,4-diamine (0.5 g, 1.96 mmol), 5-chloro-2-methoxy-phenyl boronic acid (0.73 g, 3.92 mmol), palladium (II) acetate (0.066 g, 0.294 mmol), and triphenylphosphine (0.154 g, 0.588 mmol) was added a solution of sodium carbonate (0.63 g, 5.88 mmol) dissolved in water (6 ml) followed by glyme (20 ml). The reaction mixture was stirred under an argon atmosphere at 90-95° C. for 18 hours. After cooling to room temperature, the mixture was filtered through a pad of celite under suction and concentrated. The residue was purified by flash chromatography on silica gel eluting with ethyl acetate-hexane (1:3) to provide the title compound (0.350 g, 49% yield) as a white powder. $^1$H NMR (CDCl$_3$) δ 3.86 (s, 3H, CH$_3$), 4.90 (s, 2H, NH$_2$), 6.58 (s, 1H, NH), 6.71 (s, 1H, Ar), 6.91 (d, 1H, J=8.8 Hz, Ar), 7.32-7.41 (m, 5H, Ar), 7.87 (d, 1H, J=2.7 Hz, Ar).

Example 3

6-(5-Chloro-2-methoxy-phenyl)-N*4*-(1H-indazol-6-yl)-pyrimidine-2,4-diamine

Using 1H-indazol-6-yl-amine in place of 4-chloro-phenylamine in the method described in Example 2 for the synthesis of 6-chloro-N*4*-(4-chloro-phenyl)-pyrimidine-2,4-diamine provided 6-chloro-N*4*-(1H-indazol-6-yl)-pyrimidine-2,4-diamine (42% yield).

Following the method described in Example 2,6-chloro-N*4*-(1H-indazol-6-yl)-pyrimidine-2,4-diamine and 5-chloro-2-methoxy-phenyl boronic acid provided a crude product which was purified by preparative thin layer chromatography on alumina plates eluting with methanol-ethyl acetate-hexane (1:4.5:4.5) yielding the title compound (45% yield) as a pale yellow solid. $^1$H NMR (DMSO-d$_6$) δ 3.89 (s, 3H, CH$_3$), 6.28 (s, 2H, NH$_2$), 6.81 (s, 1H, Ar), 7.18 (d, 1H, J=8.9 Hz, Ar), 7.29-7.34 (m, 1H, Ar), 7.44 (dd, 1H, J=8.7 Hz, J=2.8 Hz, Ar), 7.64 (d, 1H, J=8.7 Hz, Ar), 7.93-7.94 (m, 2H, Ar), 8.05 (s, 1H, Ar), 9.34 (s, 1H, NH), 12.80 (s, 1H, Ar).

Example 4

6-(5-Chloro-2-methoxy-phenyl)-N*4*-(4-trifluoromethylphenyl)-pyrimidine-2,4-diamine To a mixture of 4,6-dichloro-pyrimidin-2-yl-amine (0.304 g, 2.0 mmol), 5-chloro-2-methoxy-phenyl boronic acid (0.373 g, 2.0 mmol), palladium (II) acetate (0.068 g, 0.30 mmol) and triphenylphosphine (0.157 g, 0.60 mmol) was added a solution of sodium carbonate (1.36 g, 12.8 mmol) in water (5 ml) followed by glyme (20 ml). The mixture was stirred under an atmosphere of argon for 1 hour. Filtration and concentration of the filtrate provided a residue which was purified by flash chromatography on silica gel eluting with ethyl acetate-hexane (1:3) to provide 4-chloro-6-(5-chloro-2-methoxy-phenyl)-pyrimidin-2-yl-amine (0.314 g, 58% yield) as a white powder.

To a stirred suspension of 4-chloro-6-(5-chloro-2-methoxy-phenyl)-pyrimidin-2-yl-amine (0.050 g, 0.185 mmol) in ethanol (7.5 ml) was added a solution of hydrogen chloride in dioxane (4.0 M, 0.03 ml) followed by 4-(trifluoromethyl) aniline (0.06 g, 0.37 mmol). The mixture was stirred under reflux for 45 minutes. After evaporation of volatiles under reduced pressure, the residue was treated with 1.0 M hydrochloric acid (10 ml) and stirred for 30 min. Filtration provided the hydrochloride salt of the title compound which was dissolved in methanol (10 ml). A solution of sodium carbonate in water (1.0 M, 1 ml) was added. After stirring for 1 hour, volatiles were evaporated under reduced pressure. The crude product was treated with water (10 ml) and stirred for 15 minutes. Filtration provided the title compound (0.053 g, 74% yield) as a white powder. $^1$H NMR (DMSO-d$_6$) δ 3.90 (s, 3H, CH$_3$), 6.44 (s, 2H, NH$_2$), 6.81 (s, 1H, Ar), 7.19 (d, 1H, J=8.8 Hz, Ar), 7.46 (dd, 1H, J=8.8 Hz, J=2.6 Hz, Ar), 7.61 (d, 2H, J=8.5 Hz, Ar), 7.94 (d, 1H, J=2.6 Hz, Ar), 7.26 (d, 2H, J=8.5 Hz, Ar), 9.63 (s, 1H, NH).

Example 5

N*4*-(4-Bromo-phenyl)-6-(5-chloro-2-methoxy-phenyl)-pyrimidine-2,4-diamine

To a stirred suspension of 4-chloro-6-(5-chloro-2-methoxy-phenyl)-pyrimidin-2-yl-amine (0.054 g, 0.20 mmol) in ethanol (7.5 ml) was added a solution of hydrogen chloride in dioxane (4.0 M, 0.025 ml) followed by 4-bromoaniline (0.069 g, 0.40 mmol). After heating under reflux for 45 minutes, volatiles were removed under reduced pressure. The residue was treated with 1.0 M hydrochloric acid (10 ml) and stirred for 30 minutes. Filtration provided the hydrochloride salt of the title compound (0.08 g, 90% yield). $^1$H NMR (DMSO-d$_6$) δ 3.90 (s, 3H, CH$_3$), 6.71 (s, 1H, Ar), 7.30 (d, 1H, J=9.0 Hz, Ar), 7.57-7.59 (m, 2H, Ar), 7.65 (dd, 1H, J=9.0 Hz, J=2.4 Hz, Ar), 7.70 (d, 1H, J=2.4 Hz, Ar), 7.80-7.86 (m, 2H, Ar), 11.08 (s, 1H, NH).

Example 6

4-[2-Amino-6-(5-chloro-2-methoxy-phenyl)-pyrimidin-4-ylamino]-phenol

Following the method described in Example 5,4-chloro-6-(5-chloro-2-methoxy-phenyl)-pyrimidin-2-yl-amine and 4-hydroxyaniline provided the title compound (66% yield). $^1$H NMR (DMSO-d$_6$) δ 3.86 (s, 3H, CH$_3$), 6.20 (s, 2H, NH$_2$), 6.62 (s, 1H, Ar), 6.72 (d, 2H, J=8.7 Hz, Ar), 7.15 (d, 1H, J=8.9 Hz, Ar), 7.41-7.47 (m, 3H, Ar), 7.86 (d, 1H, J=2.6 Hz, Ar), 9.09 (s, 1H, NH).

Example 7

6-(5-Chloro-2-methoxy-phenyl)-N*4*-(4-methoxy-phenyl)-pyrimidine-2,4-diamine

Following the method described in Example 4,4-chloro-6-(5-chloro-2-methoxy-phenyl)-pyrimidin-2-yl-amine and 4-methoxyaniline provided the title compound (88% yield). $^1$H NMR (DMSO-d$_6$) δ 3.74 (s, 3H, CH$_3$), 3.87 (s, 3H, CH$_3$), 6.20 (s, 2H, NH$_2$), 6.66 (s, 1H, Ar), 6.88 (d, 2H, J=9.0 Hz, Ar), 7.16 (d, 1H, J-8.9 Hz, Ar), 7.43 (dd, 1H, J=8.9 Hz, J-2.7 Hz, Ar), 7.62 (d, 2H, J=9.0 Hz, Ar), 7.92 (d, 1H, J=2.7 Hz, Ar), 9.01 (s, 1H, NH).

Example 8

N*4*-Benzothiazol-6-yl-6-(5-chloro-2-methoxy-phenyl)-pyrimidine-2,4-diamine

Following the method described in Example 4,4-chloro-6-(5-chloro-2-methoxy-phenyl)-pyrimidin-2-yl-amine and benzothiazol-6-yl-amine provided the title compound (85% yield). $^1$H NMR (DMSO-d$_6$) δ 3.90 (s, 3H, CH$_3$), 6.47 (s, 2H, NH$_2$), 6.80 (d, 1H, J=2.1 Hz, Ar), 7.18-7.20 (m, 1H, Ar), 7.44-7.47 (m, 1H, Ar), 7.59-7.61 (m, 1H, Ar), 7.94-7.99 (m, 3H, Ar), 9.04 (s, 1H, Ar), 9.20 (s, 1H, J=2.1 Hz, Ar), 9.54 (s, 1H, NH).

Example 9

4-[2-Amino-6-(5-chloro-2-methoxy-phenyl)-pyrimidin-4-ylamino]-benzoic acid methyl ester Following the method described in Example 4, 4-chloro-6-(5-chloro-2-methoxy-phenyl)-pyrimidin-2-yl-amine and methyl 4-aminobenzoate provided the title compound (87% yield). $^1$H NMR (DMSO-$d_6$) δ 3.83 (s, 3H, CH$_3$), 3.90 (s, 3H, CH$_3$), 6.48 (s, 2H, NH$_2$), 6.82 (s, 1H, Ar), 7.19 (d, 1H, J-8.9 Hz, Ar), 7.43 (dd, 1H, J=8.9 Hz, J—2.7 Hz, Ar), 7.87-7.97 (m, 5H, Ar), 9.67 (s, 1H, NH).

Example 10

{4-[2-Amino-6-(5-chloro-2-methoxy-phenyl)-pyrimidin4-ylamino]-phenyl}-methanol To a stirred solution of the title compound of Example 9 in tetrahydrofuran (5.0 ml), cooled to 0° C. was added a solution of lithium aluminum hydride in tetrahydrofuran (1.0 M, 0.5 ml). After stirring at 0° C. for 2 hours, aqueous sodium hydroxide solution (1.0 M, 5.0 ml) was added carefully. The mixture was extracted with tetrahydrofuran (2×10 ml). The organic phase was washed with saturated aqueous sodium chloride solution and dried over magnesium sulfate. Evaporation of the solvent under reduced pressure provided the title compound (0.031 g, 87% yield) as a white powder. $^1$H NMR (DMSO-$d_6$) δ 3.88 (s, 3H, CH$_3$), 4.44 (d, 2H, J=5.7 Hz, CH$_2$), 5.06 (t, 1H, J=5.7 Hz, OH), 6.29 (s, 2H, NH$_2$), 6.72 (s, 1H, Ar), 7.17 (d, 1H, J=8.9 Hz, Ar), 7.23 (d, 2H, J=8.5 Hz, Ar), 7.45 (dd, 1H, J=8.9 Hz, J=2.8 Hz, Ar), 7.70 (d, 2H, J=8.5 Hz, Ar), 7.91 (d, 1H, J=2.8 Hz, Ar), 9.20 (s, 1H, NH).

Example 11

6-(5-Chloro-2-methoxy-phenyl)-N*4*-(4-nitro-phenyl)-pyrimidine-2,4-diamine

Following the method described in Example 4, 4-chloro-6-(5-chloro-2-methoxy-phenyl)-pyrimidin-2-yl-amine and 4-nitroaniline provided the title compound (80% yield). $^1$H NMR (DMSO-$d_6$) δ 3.91 (s, 3H, CH$_3$), 6.60 (s, 2H, NH$_2$), 6.86 (s, 1H, Ar), 7.20 (d, 1H, J=8.9 Hz, Ar), 7.48 (dd, 1H, J=8.9 Hz, J=2.8 Hz, Ar), 7.95 (d, 1H, J=2.8 Hz, Ar), 8.08 (d, 2H, J=9.2 Hz, Ar), 8.17 (d, 2H, J=9.2 Hz, Ar), 10.02 (s, 1H, NH).

Example 12

N*4*-(4-Amino-phenyl)-6-(5-chloro-2-methoxy-phenyl)-pyrimidine-2,4-diamine

A mixture of the title compound of Example 11 (0.060 g, 0.16 mmol) and tin (II) chloride (0.19 g, 1.0 mmol) in a solution of 1.0 M hydrochloric acid and methanol (1:10, 15 ml) was heated under reflux for 2 hours. After evaporation of volatiles under reduced pressure, the residue was treated with aqueous sodium hydroxide solution (1.0 M, 10 ml) and stirred for 15 minutes. Filtration provided the title compound (0.035 g, 64% yield) as a white powder. $^1$H NMR (DMSO-$d_6$) δ 3.84 (s, 3H, CH$_3$), 4.83 (s, 2H, NH$_2$), 6.08 (s, 2H, NH$_2$), 6.54 (d, 2H, J=8.7 Hz, Ar), 6.58 (s, 1H, Ar), 7.13 (d, 1H, J=8.9 Hz, Ar), 7.25 (d, 2H, J=8.7 Hz, Ar), 7.41 (dd, 1H, J=8.9 Hz, J-2.8 Hz, Ar), 7.89 (d, 1H, J=2.8 Hz, Ar), 8.67 (s, 1H, NH).

Example 13

N*4*-Benzo [1,3]dioxol-5-yl-6-(5-chloro-2-methoxy-phenyl)-pyrimidine-2,4-diamine Following the method described in Example 4, 4-chloro-6-(5-chloro-2-methoxy-phenyl)-pyrimidin-2-yl-amine and 3,4-methylenedioxyaniline provided the title compound (77% yield). $^1$H NMR (DMSO-$d_6$) δ 3.88 (s, 3H, CH$_3$), 5.98 (s, 2H, CH$_2$), 6.28 (s, 2H, NH$_2$), 6.67 (s, 1H, Ar), 6.84 (d, 1H, J=8.4 Hz, Ar), 7.00 (dd, 1H, J=8.3 Hz, J=1.7 Hz, Ar), 7.16 (d, 1H, J=8.9 Hz, Ar), 7.44 (dd, 1H, J=8.9 Hz, J—2.7 Hz, Ar), 7.59 (s, 1H, Ar), 7.92 (d, 1H, J=2.7 Hz, Ar), 9.09 (s, 1H, NH).

Example 14

N*4*-(4-Bromo-phenyl)-6-(2,5-dichloro-phenyl)-pyrimidine-2,4-diamine

To a mixture of 4,6-dichloro-pyrimidin-2-yl-amine (0.625 g, 3.81 mmol), 2,5-dichloro-phenyl boronic acid (0.726 g, 3.81 mmol), palladium (II) acetate (0.128 g, 0.57 mmol) and triphenylphosphine (0.30 g, 1.14 mmol) was added a solution of sodium carbonate (2.0 g, 19.0 mmol) in water (5 ml) followed by glyme (20 ml). The mixture was stirred under an argon atmosphere for 6 hours. Filtration and concentration of the filtrate yielded the crude product which was purified by flash chromatography on silica gel eluting with ethyl acetate-chloroform (1:8). After evaporation of solvents under reduced pressure, the residue was dissolved in ethanol (100 ml) and stirred while a solution of hydrogen chloride in dioxane (4.0 M, 2.5 ml) was added. After evaporation of volatiles under reduced pressure, the residue was treated with ethyl acetate (25 ml) and stirred for 16 hours. Filtration provided the hydrochloride salt of 4-chloro-6-(2,5-dichloro-phenyl)-pyrimidin-2-yl-amine (0.330 g, 28% yield) as a white powder.

A mixture of the hydrochloride salt of 4-chloro-6-(2,5-dichloro-phenyl)-pyrimidin-2-yl-amine (0.03 g, 0.096 mmol) and 4-bromoaniline (0.034 g, 0.020 mmol) in ethanol (7.5 ml) was heated under reflux for 1 hour. After evaporation of the solvent under reduced pressure, the residue was treated with 1.0 N hydrochloric acid (10 ml) and stirred for 30 minutes. Filtration provided the crude product, which was treated with ethyl acetate (10 ml) and stirred for 1 hour. After filtration the solid was dissolved in methanol (10 ml) and treated with aqueous sodium carbonate solution (1.0 M, 1 ml). After stirring for 1 hour, the solvent was evaporated under reduced pressure and the solid was treated with water (10 ml). After stirring for 15 minutes, filtration provided the title compound (59% yield) as a white powder. $^1$H NMR (DMSO-$d_6$) δ 6.31 (s, 1H, Ar), 6.54 (s, 2H, NH$_2$), 7.45 (d, 2H, J=8.9 Hz, Ar), 7.52 (dd, 1H, J=8.6 Hz, J-2.6 Hz, Ar), 7.60 (d, 1H, J=8.6 Hz, Ar), 7.64 (d, 1H, J=2.6 Hz, Ar), 7.77 (d, 2H, J=8.9 Hz, Ar), 9.46 (s, 1H, NH).

Example 15

6-(2,5-Dichloro-phenyl)-N*4*-p-tolyl-pyrimidine-2,4-diamine

Following the method described in Example 14, the hydrochloride salt of 4-chloro-6-(2,5-dichloro-phenyl)-pyrimidin-2-yl-amine and p-tolylamine provided the title compound (70% yield). $^1$H NMR (DMSO-$d_6$) δ 2.27 (s, 3H, CH$_3$), 6.27 (s, 1H, Ar), 6.41 (s, 2H, NH$_2$), 7.11 (d, 2H, J=8.0 Hz, Ar), 7.50-7.62 (m, 5H, Ar), 9.19 (s, 1H, NH).

Example 16

6-(2,5-Dichloro-phenyl)-N*4*-(4-methoxy-phenyl)-pyrimidine-2,4-diamine

Following the method described in Example 14, the hydrochloride salt of 4-chloro-6-(2,5-dichloro-phenyl)-pyrimidin-2-yl-amine and 4-methoxyaniline provided the title compound (58% yield). $^1$H NMR (DMSO-$d_6$) δ 3.74 (s, 3H, CH$_3$), 6.22 (s, 1H, Ar), 6.36 (s, 2H, NH$_2$), 6.89 (d, 2H, J=8.9 Hz, Ar), 7.51 (dd, 1H, J=8.6 Hz, J=2.6 Hz, Ar), 7.57-7.63 (m, 4H, Ar), 9.11 (s, 1H, NH).

Example 17

4-[2-Amino-6-(2,5-dichloro-phenyl)-pyrimidin-4-ylamino]-phenol

Following the method described in Example 14, the hydrochloride salt of 4-chloro-6-(2,5-dichloro-phenyl)-pyrimidin-2-yl-amine and 4-hydroxyaniline provided the title compound (57% yield). $^1$H NMR (DMSO-$d_6$) δ 6.18 (s, 1H, Ar), 6.31 (s, 2H, NH$_2$), 7.71 (d, 2H, J=8.8 Hz, Ar), 7.43 (d, 2H, J=8.8 Hz, Ar), 7.52 (dd, 1H, J=8.6 Hz, J=2.6 Hz, Ar), 7.57 (d, 1H, J=8.6 Hz, Ar), 7.61 (d, 1H, J=2.6 Hz, Ar), 8.97 (s, 1H, OH), 9.13 (s, 1H, NH).

Example 18

6-(2,5-Dichloro-phenyl)-N*4*-(4-trifuoromethyl-phenyl)-pyrimidine-2,4-diamine Following the method described in Example 14, the hydrochloride salt of 4-chloro-6-(2,5-dichloro-phenyl)-pyrimidin-2-yl-amine and 4-trifluoromethyl-aniline provided the title compound (60% yield). $^1$H NMR (DMSO-$d_6$) δ 6.38 (s, 1H, Ar), 6.63 (s, 2H, NH$_2$), 7.54 (dd, 1H, J=8.6 Hz, J=2.6 Hz, Ar), 7.60-7.66 (m, 4H, Ar), 8.00 (d, 2H, J=8.6 Hz, Ar), 9.73 (s, 1H, NH).

Example 19

6-(2,5-Dichloro-phenyl)-N*4*-(1H-indazol-6-yl)-pyrimidine-2,4-diamine

Following the method described in Example 14, the hydrochloride salt of 4-chloro-6-(2,5-dichloro-phenyl)-pyrimidin-2-yl-amine and 1H-indazol-6-yl-amine provided the title compound (30% yield). $^1$H NMR (DMSO-$d_6$) δ 6.38 (s, 1H, Ar), 6.45 (s, 2H, Ar), 7.30-7.32 (m, 1H, Ar), 7.52 (dd, 1H, J=8.6 Hz, J=2.7 Hz, Ar), 7.60 (m, 1H, Ar), 7.65 (m, 2H, Ar), 7.96 (s, 1H, Ar), 8.03 (s, 1H, Ar), 9.43 (s, 1H, NH), 12.81 (s, 1H, Ar).

Example 20

N*4*-(4-Chloro-phenyl)-6-(2,5-dichloro-phenyl)-pyrimidine-2,4-diamine

Following the method described in Example 5, 4-chloro-6-(2,5-dichloro-phenyl)-pyrimidin-2-yl-amine and 4-chloroaniline provided the hydrochloride salt of the title compound (37% yield). $^1$H NMR (DMSO-$d_6$) δ 6.47 (s, 1H, Ar), 7.46 (d, 2H, J=8.8 Hz, Ar), 7.72-7.74 (m, 2H, Ar), 7.82-7.86 (m, 3H, Ar).

Example 21

4-[2-Amino-6-(2,5-dichloro-phenyl)-pyrimidin-4-yl-amino]-benzoic acid methyl ester Following the method described in Example 14, the hydrochloride salt of 4-chloro-6-(2,5-dichloro-phenyl)-pyrimidin-2-yl-amine and methyl 4-aminobezoate provided the title compound (67% yield). $^1$H NMR (DMSO-$d_6$) δ 3.83 (s, 3H, CH$_3$), 6.40 (s, 1H, Ar), 6.64 (s, 2H, NH$_2$), 7.54 (dd, 1H, J=8.6 Hz, J=2.6 Hz, Ar), 7.60 (d, 1H, J=8.6 Hz, Ar), 7.66 (d, 1H, J=2.6 Hz, Ar), 7.88-7.96 (m, 4H, Ar), 9.74 (s, 1H, NH).

Example 22

{4-[2-Amino-6-(2,5-dichloro-phenyl)-pyrimidin-4-yl-amino]-phenyl}-methanol

Following the method described in Example 10, the title compound of Example 21 and lithium aluminum hydride provided the title compound (44% yield). $^1$H NMR (DMSO-$d_6$) δ 4.45 (d, 2H, J=5.7 Hz, CH$_2$), 5.07 (t, 1H, J=5.7 Hz, OH), 6.30 (s, 1H, Ar), 6.45 (s, 2H, NH$_2$), 7.24 (d, 2H, J=8.6 Hz, Ar), 7.52 (dd, 1H, J=8.6 Hz, J=2.6 Hz, Ar), 7.59 (d, 2H, J=8.6 Hz, Ar), 7.64 (d, 1H, J=2.6 Hz, Ar), 7.69 (d, 1H, J=8.6 Hz, Ar), 9.27 (s, 1H, NH).

Example 23

N*4*-Benzo[1,3]dioxol-5-yl-6-(2,5-dichloro-phenyl)-pyrimidine-2,4-diamine

Following the method described in Example 14, the hydrochloride salt of 4-chloro-6-(2,5-dichloro-phenyl)-pyrimidin-2-yl-amine and 3,4-methylenedioxy-aniline provided the title compound (72% yield). $^1$H NMR (DMSO-$d_6$) δ 5.99 (s, 2H, CH$_2$), 6.23 (s, 1H, Ar), 6.44 (s, 2H, NH$_2$), 6.85 (d, 1H, J=8.4 Hz, Ar), 6.98 (dd, 1H, J=8.4 Hz, J=2.1 Hz, Ar), 7.51 (dd, 1H, J=8.6 Hz, J=2.6 Hz, Ar), 7.57-7.60 (m, 2H, Ar), 7.63 (d, 1H, J=2.6 Hz, Ar), 9.19 (s, 1H, NH).

Example 24

4-[2-Amino-6-(2,5-dichloro-phenyl)-pyrimidin-4-ylamino]-benzonitrile

Following the method described in Example 14, the hydrochloride salt of 4-chloro-6-(2,5-dichloro-phenyl)-pyrimidin-2-yl-amine and 4-aminobenzonitrile provided the title compound (78% yield). $^1$H NMR (DMSO-$d_6$) δ 6.40 (s, 1H, Ar), 6.70 (s, 2H, NH$_2$), 7.54 (dd, 1H, J=8.6 Hz, J=2.6 Hz, Ar), 7.55 (d, 1H, J=8.6 Hz, Ar), 7.61 (d, 1H, J=2.6 Hz, Ar), 7.72 (d, 2H, J=8.8 Hz, Ar), 8.01 (d, 2H, J=8.8 Hz, Ar), 9.84 (s, 1H, NH).

Example 25

6-(2,5-Dichloro-phenyl)-N*4*-(4-nitro-phenyl)-pyrimidine-2,4-diamine

Following the method described in Example 14, the hydrochloride salt of 4-chloro-6-(2,5-dichloro-phenyl)-pyrimidin-2-yl-amine and 4-nitroaniline provided the title compound (57% yield). $^1$H NMR (DMSO-$d_6$) δ 6.44 (s, 1H, Ar), 6.74 (s, 2H, NH$_2$), 7.55 (dd, 1H, J=8.6 Hz, J=2.6 Hz, Ar), 7.62 (d, 1H, J=8.6 Hz, Ar), 7.67 (d, 1H, J=2.6 Hz, Ar), 8.06 (d, 2H, J=9.3 Hz, Ar), 8.17 (d, 2H, J=9.3 Hz, Ar), 10.09 (s, 1H, NH).

Example 26

6-(5-Chloro-2-methyl-phenyl)-N*4*-p-tolyl-pyrimidine-2,4-diamine

Magnesium turnings (0.346 g, 14.25 mmol) were activated by heating in an oven at 120° C. for 16 hours. Using oven-dried glassware, anhydrous tetrahydrofuran (50 ml) and a crystal of iodine were added to the magnesium. 4-Chloro-2-iodotoluene was added by syringe and air was removed. Maintaining a positive flow of argon, the reaction was heated under reflux for 5.5 hours. After cooling to −78° C. (dry ice-acetone), a solution of trimethyl borate (2.47 g, 23.76 mmol) in anhydrous tetrahydrofuran (10 ml) was added dropwise. After slowly warming to room temperature, the mixture was stirred for 16 hours. After careful addition of 1 M hydrochloric acid (20 ml), the mixture was extracted with ether (3×50 ml). The combined extracts were washed with water (3×50 ml), dried over magnesium sulfate, and concentrated under reduced pressure. The residue was washed with hexane to yield 5-chloro-2-methyl-phenyl boronic acid (0.537 g, 26% yield) as a white powder.

To a mixture of 4,6-dichloro-2-amino-pyrimidine (0.481 g, 2.93 mmol), 5-chloro-2-methyl-phenyl boronic acid (0.5 g, 2.93 mmol), palladium (II) acetate (0.1 g, 0.44 mmol), and triphenylphosphine (0.23 g, 0.88 mmol) was added a solution of sodium carbonate (1.5 g, 14.6 mmol) in water (5.0 ml) followed by glyme (20 ml). The mixture was stirred under an argon atmosphere for 16 hours. After addition of acetone (15 ml), the mixture was filtered through a pad of celite under suction and the filtrate was concentrated under vacuum. The residual solid was purified by flash chromatography on silica gel eluting with ethyl acetate-hexane (1:9). After concentration under reduced pressure, the solid was dissolved in methanol and a solution of hydrogen chloride in dioxane (4.0 M, 5 ml) was added. After concentration under vacuum, the solid was treated with ethyl acetate (5 ml) and stirred for one hour. Filtration provided the hydrochloride salt of 4-chloro-6-(5-chloro-2-methyl-phenyl) pyrimidin-2-yl-amine (0.30 g, 35% yield) as a white powder.

To a stirred suspension of the hydrochloride salt of 4-chloro-6-(5-chloro-2-methyl-phenyl)-pyrimidin-2-yl-amine (0.01 g, 0.0344 mmol) in ethanol (5 ml) was added a solution of hydrogen chloride in dioxane (4.0 M, 0.01 ml) followed by p-tolylamine (0.074 g, 0.068 mmol). The mixture was heated under reflux for 75 minutes. After evaporation of volatiles under reduced pressure, the residue was treated 1.0 M hydrochloric acid (10 ml) and stirred for 30 minutes. After filtration the solid was dissolved in methanol (5 ml) and treated with a solution of sodium carbonate in water (1.0 M, 1.0 ml). After stirring for 30 minutes volatiles were evaporated under reduced pressure. The residue was treated with water (10 ml) and stirred for 15 minutes. Filtration provided the title compound (0.011 g, 98% yield) as a white powder. $^1$H NMR (DMSO-d$_6$) δ 2.27 (s, 3H, CH$_3$), 2.34 (s, 3H, CH$_3$), 6.07 (s, 1H, Ar), 6.33 (s, 2H, NH$_2$), 7.10 (d, 2H, J=8.3 Hz, Ar), 7.30 (d, 1H, J=8.2 Hz, Ar), 7.35-7.40 (m, 2H, Ar), 7.61 (d, 1H, J=8.4 Hz, Ar), 9.09 (s, 1H, NH).

Example 27

6-(5-Chloro-2-methyl-phenyl)-N*4*-(4-chloro-phenyl)-pyrimidine-2,4-diamine

Following the method described in Example 26, 4-chloro-6-(5-chloro-2-methyl-phenyl)-pyrimidin-2-yl-amine and 4-chloroaniline provided the title compound (78% yield). $^1$H NMR (DMSO-d$_6$) δ 2.34 (s, 3H, CH$_3$), 6.10 (s, 1H, Ar), 6.45 (s, 2H, NH$_2$), 7.30-7.33 (m, 3H, Ar), 7.37 (dd, 1H, J=8.1 Hz, J=2.3 Hz, Ar), 7.41 (d, 1H, J=2.2 Hz, Ar), 7.80-7.83 (m, 2H, Ar), 9.35 (s, 1H, NH).

Example 28

6-(5-Chloro-2-methyl-phenyl)-N*4*-(4-methoxy-phenyl)-pyrimidine-2,4-diamine

Following the method described in Example 26, 4-chloro-6-(5-chloro-2-methyl-phenyl)-pyrimidin-2-yl-amine and 4-methoxy-phenylamine provided the title compound (52% yield). $^1$H NMR (DMSO-d$_6$) δ 2.34 (s, 3H, CH$_3$), 3.74 (s, 3H, CH$_3$), 6.01 (s, 1H, Ar), 6.28 (s, 2H, NH$_2$), 6.87-6.89 (m, 2H, Ar), 7.30 (d, 1H, J=8.2 Hz, Ar), 7.34-7.39 (m, 2H, Ar), 7.60 (d, 2H, J=8.9 Hz, Ar), 9.01 (s, 1H, NH).

Example 29

6-(5-Chloro-2-methyl-phenyl)-N*4*-(4-trifluoromethyl-phenyl)-pyrimidine-2,4-diamine Following the method described in Example 26, 4-chloro-6-(5-chloro-2-methyl-phenyl)-pyrimidin-2-yl-amine and 4-trifluoromethyl-phenylamine provided the title compound (46% yield). $^1$H NMR (DMSO-d$_6$) δ 2.36 (s, 3H, CH$_3$), 6.17 (s, 1H, Ar), 6.54 (s, 2H, NH$_2$), 7.32 (d, 1H, J=8.3 Hz, Ar), 7.38 (dd, 1H, J=8.1 Hz, J—2.3 Hz, Ar), 7.43 (d, 1H, J=2.1 Hz, Ar), 7.61 (d, 2H, J=8.7 Hz, Ar), 8.00 (d, 2H, J=8.5 Hz, Ar), 9.63 (s, 1H, NH).

Example 30

N*4*-(4-Bromo-phenyl)-6-(5-chloro-2-methyl-phenyl)-pyrimidine-2,4-diamine

Following the method described in Example 26, 4-chloro-6-(5-chloro-2-methyl-phenyl)-pyrimidin-2-yl-amine and 4-bromoaniline provided the title compound (84% yield). $^1$H NMR (DMSO-d$_6$) δ 2.35 (s, 3H, CH$_3$), 6.10 (s, 1H, Ar), 6.45 (s, 2H, NH$_2$), 7.31 (d, 1H, J=8.3 Hz, Ar), 7.37 (dd, 1H, J=8.2 Hz, J=2.3 Hz, Ar), 7.41 (d, 1H, J=2.3 Hz, Ar), 7.43-7.45 (m, 2H, Ar), 7.78-7.75 (m, 2H, Ar), 9.35 (s, 1H, NH).

Example 31

6-(5-Chloro-2-methyl-phenyl)-N*4*-(1H-indazol-6-yl)-pyrimidine-2,4-diamine

Following the method described in Example 26, 4-chloro-6-(5-chloro-2-methyl-phenyl)-pyrimidin-2-yl-amine and 1H-indazol-6-yl-amine provided the title compound (73% yield). $^1$H NMR (DMSO-d$_6$) δ 2.37 (s, 3H, CH$_3$), 6.17 (s, 1H, Ar), 6.35 (s, 2H, NH$_2$), 7.30-7.33 (m, 2H, Ar), 7.37 (dd, 1H, J=8.2 Hz, J=2.3 Hz, Ar), 7.43 (d, 1H, J=2.3 Hz, Ar), 7.64 (d, 1H, J=8.6 Hz, Ar), 7.95 (s, 1H, Ar), 8.04 (s, 1H, Ar), 9.33 (s, 1H, NH), 12.80 (s, 1H, Ar).

Example 32

4-[2-Amino-6-(5-chloro-2-methyl-phenyl)-pyrimidin4-ylamino]-benzonitrile

Following the method described in Example 26, 4-chloro-6-(5-chloro-2-methyl-phenyl)-pyrimidin-2-yl-amine and 4-amino-benzonitrile provided the title compound (71% yield). ¹H NMR (DMSO-d₆) δ 2.36 (s, 3H, CH₃), 6.19 (s, 1H, Ar), 6.61 (s, 2H, NH₂), 7.32 (d, 1H, J=8.2 Hz, Ar), 7.38 (dd, 1H, J=8.2 Hz, J=2.3 Hz, Ar), 7.43 (d, 1H, J-2.3 Hz, Ar), 7.72 (d, 2H, J=8.8 Hz, Ar), 8.00 (d, 2H, J=8.8 Hz, Ar), 9.73 (s, 1H, NH).

Example 33

{4-[2-Amino-6-(5-chloro-2-methyl-phenyl)-pyrimidin4-ylamino]-phenyl}-methanol

Following the method described in Example 14, the hydrochloride salt of 4-chloro-6-(5-chloro-2-methyl-phenyl)-pyrimidin-2-yl-amine and methyl 4-aminobenzoate provided 4-[2-amino-6-(5-chloro-2-methyl-phenyl)-pyrimidin-4-ylamino]-benzoic acid methyl ester (85% yield).

Following the method described in Example 10, 4-[2-amino-6-(5-chloro-2-methyl-phenyl)-pyrimidin-4-ylamino]-benzoic acid methyl ester provided the title compound (76% yield). ¹H NMR (DMSO-d₆) δ 2.35 (s, 3H, CH₃), 4.45 (d, 2H, J=5.4 Hz, CH₂), 5.06 (t, 1H, J=5.4 Hz, OH), 6.09 (s, 1H, Ar), 6.36 (s, 2H, NH₂), 7.24 (d, 2H, J=8.1 Hz, Ar), 7.30-7.40 (m, 3H, Ar), 7.68 (d, 2H, J=8.1 Hz, Ar), 9.17 (s, 1H, NH).

Example 34

6-(5-Chloro-2-methoxy-phenyl)-N*2*-(4-chloro-phenyl)-pyrimidine-2,4-diamine

A mixture of 2,6-dichloro-pyrimidin-4-yl-amine (0.492 g, 3.0 mmol) and 4-chloro-aniline (1.54 g, 12.0 mmol) in dioxane (25 ml) was heated under reflux for 3 hours. After cooled to room temperature, the mixture was filtered. Concentration of the filtrate under reduced pressure provided the crude product which was purified by flash chromatography on silica gel eluting with ethyl acetate-hexane (1:3) to provide 6-chloro-N*2*-(4-chloro-phenyl)-pyrimidine-2,4-diamine (0.32 g, 42% yield) as a white powder.

A mixture of 6-chloro-N*2*-(4-chloro-phenyl)-pyrimidine-2,4-diamine (0.077 g, 0.30 mmol), 5-chloro-2-methoxy-phenyl boronic acid (0.112 g, 0.60 mmol), palladium (II) acetate (0.017 g, 0.075 mmol), 2-(dicyclohexylphosphino) biphenyl (0.105 g, 0.30 mmol) and potassium phosphate (0.254 g, 1.2 mmol) in dry toluene (3.5 ml) was heated at 90-100° C. under an argon atmosphere for 18 hours. After cooling to room temperature, ether (20 ml) was added and the mixture was washed with aqueous sodium hydroxide solution (1.0 M, 10 ml), with saturated aqueous sodium chloride solution (10 ml), and dried over magnesium sulfate. After concentrating under reduced pressure, the residue was purified by flash chromatography on silica gel eluting with ethyl acetate-hexane (1:3) to provide the title compound (0.032 g, 30% yield) as a white powder.

Alternatively, to a mixture of 2,6-dichloro-pyrimidin-4-yl-amine (1.64 g, 10.0 mmol), 5-chloro-2-methoxy-phenyl boronic acid (1.84 g, 10.0 mmol), palladium (II) acetate (0.337 g, 1.0 mmol) and triphenylphosphine (0.786 g, 3.0 mmol) was added a solution of sodium carbonate (5.3 g, 50.0 mmol) in water (10 ml) followed by glyme (50 ml). The mixture was stirred under an argon atmosphere for 24 hours. After addition of acetone (50 ml), filtration and concentration of the filtrate provided the crude product which was treated with chloroform (50 ml) and stirred for 1 hour. Filtration provided a solid which was dissolved in ethanol (50 ml). A solution of hydrogen chloride in dioxane (4.0 M, 5 ml) was added and volatiles were evaporated under reduce pressure. The residue was treated with ethyl acetate (25 ml) and stirred for 2 hours. Filtration provided the hydrochloride salt of 2-chloro-6-(5-chloro-2-methoxy-phenyl)-pyrimidin-4-yl-amine (0.42 g, 14% yield).

To a stirred suspension of the hydrochloride salt of 2-chloro-6-(5-chloro-2-methoxy-phenyl)-pyrimidin-4-yl-amine (0.023 g, 0.075 mmol) in ethanol (7.0 ml) was added 4-chloroaniline (0.025 g, 0.20 mmol). The mixture was stirred under reflux for 6 hours. After evaporation of the solvent under reduced pressure, the residue was treated with hydrochloric acid (1.0 M, 10 ml) and stirred for 30 minutes. Filtration provided the hydrochloride salt of 6-(5-chloro-2-methoxy-phenyl)-N*2*-(4-chloro-phenyl)-pyrimidine-2,4-diamine which was treated with methanol (10 ml) and stirred while a solution of sodium carbonate in water (1.0 M, 1 ml) was added. After stirring for 1 hour, solvents were evaporated under reduced pressure. The residual solid was treated with water (10 ml) and stirred for 15 minutes. Filtration provided the title compound (0.019 g, 70% yield) as a white powder. ¹H NMR (CDCl₃) δ 4.80 (s, 2H, NH₂), 6.62 (s, 1H, Ar), 6.94 (d, 1H, J=8.8 Hz, Ar), 6.98 (s, 1H, NH), 7.27-7.30 (m, 2H, Ar), 7.36 (dd, 1H, J=8.8 Hz, J=2.8 Hz, Ar), 7.61-7.63 (m, 2H, Ar), 7.93 (d, 1H, J=2.8 Hz, Ar), Example 35

6-(5-Chloro-2-methoxyphenyl)-N*2*-(1H-indazol-6yl)-pyrimidine-2,4-diamine

Following the method described in Example 34, the hydrochloride salt of 2-chloro-6-(5-chloro-2-methoxy-phenyl)-pyrimidin-4-yl-amine and 6-aminoindazole provided the title compound (85% yield). ¹H NMR (DMSO-d₆) δ 3.88 (s, 3H, CH₃), 6.58 (s, 1H, Ar), 6.15 (s, 2H, NH₂), 7.19 (d, 1H, J=8.9 Hz, Ar), 7.42-7.48 (m, 2H, Ar), 7.56 (d, 1H, J=8.6 Hz, Ar), 7.89 (s, 1H, Ar), 7.91 (d, 1H, J=2.8 Hz, Ar), 8.11 (s, 1H, Ar), 9.13 (s, 1H, NH), 12.70 (s, 1H, NH).

Example 36

N-(4-Bromo-phenyl)-2-(5-chloro-2-methoxy-phenyl)-pyrimidine4,6-diamine

Hydrogen chloride gas (~200 mmol) was passed into a solution of 5-chloro-2-methoxy-benzonitrile(1.68 g, 10.0 mmol) in ethanol (50 ml). After stirring for 48 hours, the mixture was concentrated under reduced pressure. The residue was treated with ethyl acetate (25 ml) and stirred for 1 hour. Filtration provided 5-chloro-2-methoxy-benzimidic acid ethyl ester (1.20 g, 56% yield) as a white powder.

A mixture of 5-chloro-2-methoxy-benzimidic acid ethyl ester (1.0 g, 4.0 mmol) and a solution of ammonia in methanol (7.0 M, 50 ml) was stirred for 48 hours. Evaporation of volatiles under reduced pressure provided 5-chloro-2-methoxy-benzylideneamine (0.875 g, 99% yield).

To a mixture of 5-chloro-2-methoxy-benzylideneamine (0.62 g, 2.8 mmol) and diethyl malonate (0.672 g, 4.2 mmol) in ethanol (10 ml) was added a 25% solution of sodium methoxide in methanol (1.51 g, 7.0 mmol). After stirring at 60-65° C. for 16 hours, solvents were evaporated under reduced pressure. The residue was treated with water (10 ml) and the mixture was acidified to pH 2 by addition of concentrated hydrochloric acid. After addition of hexane (20 ml), the mixture was stirred for 1 hour. Filtration provided 2-(5-chloro-2-methoxy-phenyl)-pyrimidine-4,6-diol (0.45 g, 64% yield) as a beige powder.

A mixture of 2-(5-chloro-2-methoxy-phenyl)-pyrimidine-4,6-diol (0.45 g, 1.55 mmol) and phosphorus oxychloride (20 ml) was heated under reflux for 6 hours. Unreacted phosphorus oxychloride was evaporated under reduced pressure. The residue was purified by flash chromatography on silica gel eluting with chloroform to provide 4,6-dichloro-2-(5-chloro-2-methoxy-phenyl)-pyrimidine (0.35 g, 68% yield) as a white powder.

A pressure bottle was charged with tetrahydrofuran (50 ml) and cooled to 0° C. Ammonia gas was passed through the tetrahydrofuran until saturated. To this solution was added 4,6-dichloro-2-(5-chloro-2-methoxy-phenyl)-pyrimidine (0.15 g, 0.52 mmol) and the mixture was heated at 75-80° C. for 18 hours. Evaporation of volatiles under reduced pressure provided the hydrochloride salt of 6-chloro-2-(5-chloro-2-methoxy-phenyl)-pyrimidin-4-yl-amine (0.10 g, 71%).

To a stirred suspension of the hydrochloride salt of 6-chloro-2-(5-chloro-2-methoxy-phenyl)-pyrimidin-4-yl-amine (0.020 g, 0.065 mmol) in ethanol (5.0 ml) was added 4-bromoaniline (0.022 g, 0.13 mmol). After heating under reflux for 20 hours, the solvent was evaporated under reduced pressure. The residue was treated with 1.0 M hydrochloric acid (10 ml) and stirred for 30 minutes. Filtration provided a solid which was treated with methanol (10 ml) and stirred while a solution of sodium carbonate in water (1.0 M, 1 ml) was added. After stirring for 1 hour, the solvents were evaporated under reduced pressure. The residue was treated with water (10 ml) and stirred for 15 minutes. Filtration provided the title compound (0.011 g, 42% yield) as a beige powder. $^1$H NMR (DMSO-$d_6$) δ 3.83 (s, 3H, CH$_3$), 5.74 (s, 1H, Ar), 6.50 (s, 2H, NH$_2$), 7.14 (d, 1H, J=8.9 Hz, Ar), 7.40-7.45 (m, 3H, Ar), 7.55 (d, 1H, J=2.7 Hz), 7.65-7.67 (m, 2H, Ar), 9.16 (s, 1H, NH).

Example 37

2-(5-Chloro-2-methoxy-phenyl)-N-(1H-indazol-6-yl)-pyrimidine4,6-diamine

Following the method described in Example 36, the hydrochloride salt of 6-chloro-2-(5-chloro-2-methoxy-phenyl)-pyrimidin-4-yl-amine and 6-aminoindazole provided the title compound (0.02 g, 83% yield). $^1$H NMR (DMSO-$d_6$) δ 3.83 (s, 3H, CH$_3$), 5.82 (s, 1H, Ar), 6.47 (s, 2H, NH$_2$), 7.14-7.18 (m, 2H, Ar), 7.44 (d, 1H, J—8.8 Hz, J=2.7 Hz, Ar), 7.50 (d, 1H, J=2.7 Hz, Ar), 7.61 (d, 1H, J=8.7 Hz, Ar), 7.91 (s, 1H, Ar), 8.03 (s, 1H, Ar), 9.13 (s, 1H, NH), 12.73 (s, 1H, NH).

Example 38

[6-(5-Chloro-2-methoxy-phenyl)-2-methyl-pyrimidin-4-yl]-(4-chloro-phenyl)-amine

To a mixture of 5-chloro-2-methoxy-benzoic acid (2.0 g, 10.7 mmol) and acetonitrile (50 ml) was added 1,1'-carbonyldiimidazole (2.1 g, 12.8 mmol) and stirred until gas evolution ceased (10 minutes). The resulting solution containing (5-chloro-2-methoxy-phenyl)-imidazol-1-yl-methanone was used immediately in the next step.

To a stirred mixture of ethyl malonate sodium salt (3.8 g, 24.7 mmol) and magnesium sulfate (3.2 g, 26.3 mmol) in acetonitrile (60 ml) was added triethylamine (4.7 ml, 33.5 mmol) under an argon atmosphere. After stirring for 2 hours, the solution containing (5-chloro-2-methoxy-phenyl)-imidazol-1-yl-methanone was added. After stirring at 80° C. for 2 hours, magnesium chloride (2.5 g, 26.3 mmol) was added and the mixture was stirred for 16 hours. After cooling to 10° C., concentrated hydrochloric acid (5 ml) was added and the mixture was stirred for 30 minutes. The layers were separated and the aqueous layer was extracted with ethyl acetate (3×60 ml). The combined organic layers were dried over magnesium sulfate and concentrated under reduced pressure. The residue was purified by flash chromatography on silica gel eluting with ethyl acetate-hexane (1:4 followed by 1:3) to provide 3-(5-chloro-2-methoxy-phenyl)-3-oxopropionic acid ethyl ester (2.3 g, 76% yield) as an oil. $^1$H NMR (CDCl$_3$) δ 1.23 (t, 3H, J=8.7 Hz CH$_3$), 3.89 (s, 3H, CH$_3$), 3.94 (s, 2H, CH$_2$), 4.17 (q, 2H, CH$_2$), 6.91 (d, 1H, J=8.6 Hz, Ar), 7.45 (dd, 1H, J=8.8 Hz, J=2.6 Hz, Ar), 7.85 (d, 1H, J=2.6 Hz, Ar).

A mixture of 3-(5-chloro-2-methoxy-phenyl)-3-oxopropionic acid ethyl ester (0.9 g, 3.2 mmol), acetamidine hydrochloride (448 mg, 4.7 mmol) and potassium carbonate (1.3 g, 9.6 mmol) in ethanol (15 ml) was stirred at 100° C. in thick wall tube for 60 hours. After cooling to room temperature, the mixture was poured into ice cold water. The solid was collected by filtration, washed with water and ether and dried under vacuum to provide 6-(5-chloro-2-methoxy-phenyl)-2-methyl-3H-pyrimidin-4-one (530 mg, 68% yield) as a white powder. $^1$H NMR (DMSO-$d_6$) δ 2.32 (s, 3H, CH$_3$), 3.85 (s, 3H, CH$_3$), 6.77 (s, 1H, CH, Ar), 7.15 (d, 1H, J=8.8 Hz, Ar), 7.45 (dd, 1H, J=8.8 Hz, J=2.9 Hz, Ar), 7.90 (d, 1H, J=2.9 Hz, Ar), 12.42 (s, 1H, NH).

To a suspension of 6-(5-chloro-2-methoxy-phenyl)-2-methyl-3H-pyrimidin-4-one (520 mg, 2.1 mmol) in dichloromethane (20 ml) and 1,4-dioxane (20 ml) was added N,N-dimethylformamide (0.2 ml) followed by a solution of oxalyl chloride in dichloromethane (2 M, 4.2 ml). After stirring for 1 hour, the mixture was concentrated under vacuum. The residue was partitioned between ethyl acetate (100 ml) and saturated aqueous sodium bicarbonate solution (60 ml). The organic phase was dried over magnesium sulfate and concentrated under vacuum to give 4-chloro-6-(5-chloro-2-methoxy-phenyl)-2-methyl-pyrimidine (530 mg, 94% yield) as a white powder. $^1$H NMR (DMSO-$d_6$) δ 2.67 (s, 3H, CH$_3$), 3.91 (s, 3H, CH$_3$), 7.26 (d, 1H, J=9.2 Hz, Ar), 7.59 (dd, 1H, J=8.8 Hz, J=2.6 Hz, Ar), 7.95 (s, 1H, Ar), 7.96 (d, 1H, J=2.9 Hz, Ar).

To an argon saturated solution of 4-chloro-6-(5-chloro-2-methoxy-phenyl)-2-methyl-pyrimidine (50 mg, 0.18 mmol), 4-chloroaniline (23 mg, 0.18 mmol), rac-2,2'-bis(diphenylphosphino)-1,1'-binaphthyl (66 mg, 0.1 mmol) and sodium tert-butoxide (26 mg, 0.27 mmol) in toluene (10 ml) was added tris(dibenzylideneacetone)-dipalladium (92 mg, 0.1 mmol). After stirring at 80° C. under an argon atmosphere for 6 hours, the mixture was concentrated under vacuum. The residue was purified by flash chromatography on silica gel eluting with ethyl acetate-hexane (1:5 followed by 1:3) to provide the title compound (33 mg, 51% yield) as a white powder.

Alternatively, a solution of 4-chloro-6-(5-chloro-2-methoxy-phenyl)-2-methyl-pyrimidine (50 mg, 0.18 mmol) and 4-chloroaniline (23 mg, 0.18 mmol) in ethanol (10 ml) was stirred at 80° C. under an argon atmosphere for 5 hours. After concentration under vacuum the crude product was crystallized (ethyl acetate) to give the title compound (40 mg, 60% yield). $^1$H NMR (DMSO-$d_6$) δ 2.53 (s, 3H, CH$_3$), 3.33 (s, 3H, CH$_3$), 7.23 (d, 1H, J=8.9 Hz, Ar), 7.33 (s, 1H, Ar), 7.41 (d, 2H, J=8.9 Hz, Ar), 7.51 (dd, 1H, J=8.9 Hz, J=2.8 Hz, Ar), 7.79 (d, 2H, J=8.9 Hz, Ar), 8.0 (d, 1H, J=2.8 Hz, Ar), 9.75 (s, 1H, NH).

Example 39

[6-(5-Chloro-2-methoxy-phenyl)-2-methyl-pyrimidin-4-yl]-(4-bromo-phenyl)-amine

Following the method described in Example 38, using 4-bromo-aniline in place of 4-chloroaniline provided the title compound (41% yield). $^1$H NMR (DMSO-$d_6$) δ 2.52 (s, 3H, CH$_3$), 3.73 (s, 3H, CH$_3$), 7.18 (d, 1H, J=8.8 Hz, Ar), 7.30 (d, 2H, J=8.8 Hz, Ar), 7.52 (dd, 1H, J=8.8 Hz, J=2.9 Hz, Ar), 7.69 (s, 1H, Ar), 7.74 (d, 2H, J=8.8 Hz, Ar), 7.99 (d, 1H, J=2.9 Hz, Ar).

Example 40

[6-(5-Chloro-2-methoxy-phenyl)-2-methyl-pyrimidin4-yl]-(1H-indazol-6-yl)-amine

Following the method described in Example 38 (alternate method), using 6-aminoindazol in place of 4-chloroaniline provided the title compound (71% yield). $^1$H NMR (DMSO-$d_6$) δ 2.58 (s, 3H, CH$_3$), 3.92 (s, 3H, CH$_3$), 7.19-7.21 (m, 1H, Ar), 7.23 (d, 1H, J=8.9 Hz, Ar), 7.39 (s, 1H, Ar), 7.51 (dd, 1H, J=8.9 Hz, J=2.8 Hz, Ar), 7.69 (d, 1H, J=8.6 Hz, Ar), 7.97 (s, 1H, Ar), 7.99 (d, 1H, J=2.6 Hz, Ar), 8.31 (s, 1H, Ar), 9.80 (s, 1H, NH), 12.85 (s, 1H, NH).

Example 41

[6-(5-Chloro-2-methyl-phenyl)-2-methyl-pyrimidin-4-yl]-(4-bromo-phenyl)-amine 3-(5-Chloro-2-methyl-phenyl)-3-oxopropionic acid ethyl ester was prepared according to the method described in Example 38 for the synthesis of 3-(5-chloro-2-methoxy-phenyl)-3-oxopropionic acid ethyl ester (71% yield).

4-Chloro-6-(5-chloro-2-methyl-phenyl)-2-methyl-pyrimidine was prepared according to the method described in Example 38 for the synthesis of 4-chloro-6-(5-chloro-2-methoxy-phenyl)-2-methyl-pyrimidine in two steps using 3-(5-chloro-2-methyl-phenyl)-3-oxopropionic acid ethyl ester and acetamidine hydrochloride (11% yield). $^1$H NMR (DMSO-$d_6$) δ 2.36 (s, 3H, CH$_3$), 2.68 (s, 3H, CH$_3$), 7.40 (d, 1H, J=8.3 Hz, Ar), 7.49 (dd, 1H, J=8.3 Hz, J=2.3 Hz, Ar), 7.57 (d, 1H, J=2.3 Hz, Ar), 7.79 (s, 1H, Ar).

Following the method described in Example 38, 4-chloro-6-(5-chloro-2-methyl-phenyl)-2-methyl-pyrimidine and 4-bromoaniline provided the title compound (21% yield). $^1$H NMR (DMSO-$d_6$) δ 2.48 (s, 3H, CH$_3$), 2.54 (s, 3H, CH$_3$), 6.71 (s, 1H, Ar), 7.36 (d, 1H, J=8.2 Hz, Ar), 7.42 (dd, 1H, J=8.2 Hz, J=2.2 Hz, Ar), 7.47 (d, 1H, J=2.1 Hz, Ar), 7.52 (d, 2H, J=8.8 Hz, Ar), 7.73 (d, 2H, J=8.8 Hz, Ar), 9.72 (s, 1H, NH).

Example 42

[6-(5-Chloro-2-methyl-phenyl)-2-methyl-pyrimidin-4-yl]-(4-chloro-phenyl)-amine

Following the method described in Example 38 (alternate method), 4-chloro-6-(5-chloro-2-methyl-phenyl)-2-methyl-pyrimidine and 4-chloroaniline provided the title compound (97% yield). $^1$H NMR (DMSO-$d_6$) δ 2.35 (s, 3H, CH$_3$), 2.53 (s, 3H, CH$_3$), 6.71 (s, 1H, Ar), 7.35-7.44 (m, 4H, Ar), 7.49 (d, 1H, J=2.2 Hz, Ar), 7.78 (d, 1H, J=8.8 Hz, Ar), 9.72 (s, 1H, NH).

Example 43

[6-(5-Chloro-2-methyl-phenyl)-2-methyl-pyrimidin-4-yl]-(1H-indazol-6-yl)-amine

Following the method described in Example 38 (alternate method), 4-chloro-6-(5-chloro-2-methyl-phenyl)-2-methyl-pyrimidine and 6-aminoindazol provided the title compound (64% yield). $^1$H NMR (DMSO-$d_6$) δ 2.32 (s, 3H, CH$_3$), 2.57 (s, 3H, CH$_3$), 6.78 (s, 1H, Ar), 7.18 (dd, 1H, J=8.7 Hz, J=1.6 Hz, Ar), 7.36 (d, 1H, J=8.2 Hz, Ar), 7.43 (dd, 1H, J=8.2 Hz, J=2.3 Hz, Ar), 7.49 (d, 1H, J=2.2 Hz, Ar), 7.69 (d, 1H, J=8.6 Hz, Ar), 7.97 (s, 1H, Ar), 8.33 (s, 1H, Ar), 9.75 (s, 1H, NH), 12.89 (s, 1H, NH).

Example 44

{4-[2-Amino-6-(5-chloro-2-ethoxy-phenyl)-pyrimidin-4-ylamino]-phenyl}-methanol

A mixture of 4,6-dichloro-pyrimidin-2-yl-amine (6.6 g, 40 mmol), 4-aminobenzyl alcohol (8.0 g, 65 mmol) and N,N-diisopropylethylamine (15 ml) in ethanol (200 ml) was heated under reflux for 72 hours. Concentration under reduced pressure provided a solid which was stirred with 1.0 M hydrochloric acid (200 ml) for 1 hour, filtered, dried under reduced pressure, stirred with ethyl acetate (200 ml) for 2 hours, filtered, and dissolved in methanol (300 ml). Aqueous sodium carbonate solution (1.0 M, 50 ml) was added. After stirring for 2 hours, volatiles were evaporated under reduced pressure and water (200 ml) was added. Filtration and drying provided [4-(2-amino-6-chloro-pyrimidin-4-yl-amino)-phenyl]-methanol (6.3 g, 63% yield) as a white powder.

To a mixture of [4-(2-amino-6-chloro-pyrimidin-4-yl-amino)-phenyl]-methanol (6.0 g, 24 mmol), 5-chloro-2-ethoxy-phenyl boronic acid (7.7 g, 38.4 mmol), palladium (II) acetate (0.54 g, 2.4 mmol) and triphenylphosphine (1.26 g, 4.8 mmol) was added a solution of sodium carbonate (12.7 g, 120 mmol) in water (80 ml) followed by glyme (300 ml). The mixture was stirred under an argon atmosphere at 95-105° C. for 18 hours. Filtration and concentration of the filtrate yielded a residue which was purified by flash chromatography on silica gel eluting with ethyl acetate-hexane (1:3) to provide the title compound (5.5 g, 62% yield) as a white powder. $^1$H NMR (DMSO-$d_6$) δ 1.38 (t, 3H, J=6.9 Hz, CH$_3$), 4.13 (q, 2H, J=6.9 Hz, CH$_2$), 4.45 (d, 2H, J=5.7 Hz, CH$_2$), 5.07 (t, 1H, J=5.7 Hz, OH), 6.26 (s, 2H, NH$_2$), 6.77 (s, 1H, Ar), 7.14 (d, 1H, J=8.9 Hz, Ar), 7.24 (d, 2H, J=8.4 Hz, Ar), 7.41 (dd, 1H, J=8.8, 2.8 Hz, Ar), 7.64 (d, 2H, J=8.3 Hz, Ar), 7.93 (d, 1H, J=2.8 Hz, Ar), 9.12 (s, 1H, NH).

Example 45

4-[2-Amino-6-(5-chloro-2-methoxy-phenyl)-pyrimidin-4-ylamino]-benzonitrile

Following the method described in Example 4, 4-chloro-6-(5-chloro-2-methoxy-phenyl)-pyrimidin-2-yl-amine and 4-aminobenzonitrile provided the title compound (90% yield). $^1$H NMR (DMSO-$d_6$) δ 3.90 (s, 3H, CH$_3$), 6.54 (s, 2H, NH$_2$), 6.81 (s, 1H, Ar), 7.19 (d, 1H, J=8.9 Hz, Ar), 7.47 (dd, 1H, J=8.8, 2.8 Hz, Ar), 7.71 (d, 2H, J=8.7 Hz, Ar), 7.94 (d, 1H, J=2.8 Hz, Ar), 8.02 (d, 2H, J=8.8 Hz, Ar), 9.76 (s, 1H, NH).

Example 46

6-(5-Chloro-2-ethoxy-phenyl)-N*4*-(4-nitro-phenyl)-pyrimidine-2,4-diamine

Following the method described in Example 4,4-chloro-6-(5-chloro-2-ethoxy-phenyl)-pyrimidin-2-yl-amine and 4-nitroaniline provided the title compound (84% yield). $^1$H NMR (DMSO-d$_6$) δ 1.42 (t, 3H, J=4.6 Hz, CH$_3$), 4.18 (q, 2H, J=4.5 Hz, CH$_2$), 6.59 (s, 2H, NH$_2$), 6.89 (s, 1H, Ar), 7.14 (d, 1H, J=8.9 Hz, Ar), 7.44 (dd, 1H, J=8.8, 2.8 Hz, Ar), 7.93 (d, 1H, J=2.8 Hz, Ar), 8.06-8.19 (m, 4H, Ar), 9.96 (s, 1H, NH).

Example 47

2-{4-[2-Amino-6-(5-chloro-2-ethoxy-phenyl)-pyrimidin4-ylamino]-phenyl}-ethanol Following the method described in Example 4,4-chloro-6-(5-chloro-2-ethoxy-phenyl)-pyrimidin-2-yl-amine and 4-aminophenethyl alcohol provided the title compound (94% yield). $^1$H NMR (DMSO-d$_6$) δ 1.37 (t, 3H, J=6.9 Hz, CH$_3$), 2.69 (t, 2H, J=7.0 Hz, CH$_2$), 3.56-3.61 (m, 2H, CH$_2$), 4.12 (q, 2H, J=6.9 Hz, CH$_2$), 4.62 (t, 1H, J=5.1 Hz, OH), 6.22 (s, 2H, NH$_2$), 6.77 (s, 1H, Ar), 7.12-7.15 (m, 3H, Ar), 7.40 (dd, 1H, J=8.8 Hz, 2.9 Hz, Ar), 7.56 (d, 2H, J=8.2 Hz, Ar), 7.94 (d, 1H, J=2.8 Hz, Ar), 9.53 (s, 1H, NH).

Example 48

2-{4-[2-Amino-6-(2,5-dichloro-phenyl)-pyrimidin4-ylamino]-phenyl}-ethanol

Following the method described in Example 4,4-chloro-6-(2,5-dichloro-phenyl)-pyrimidin-2-yl-amine and 4-aminophenethyl alcohol provided the title compound (46% yield). $^1$H NMR (DMSO-d$_6$) δ 2.68 (t, 2H, J=6.9 Hz, CH$_2$), 3.58-3.61 (m, 2H, CH$_2$), 4.62 (t, 1H, J=5.0 Hz, OH), 6.28 (s, 1H, Ar), 6.41 (s, 2H, NH$_2$), 7.14 (d, 2H, J=8.2 Hz, Ar), 7.50-7.63 (m, 5H, Ar), 9.21 (s, 1H, NH).

Example 49

2-{4-[2-Amino-6-(5-chloro-2-methyl-phenyl)-pyrimidin4-ylamino]-phenyl}-ethanol Following the method described in Example 4,4-chloro-6-(5-chloro-2-methyl-phenyl)-pyrimidin-2-yl-amine and 4-aminophenethyl alcohol provided the title compound (51% yield). $^1$H NMR (DMSO-d$_6$) δ 2.35 (s, 3H, CH$_3$), 2.68 (t, 2H, J=7.1 Hz, CH$_2$), 3.56-3.61 (m, 2H, CH$_2$), 4.62 (t, 1H, J=5.2 Hz, OH), 6.07 (s, 1H, Ar), 6.33 (s, 2H, NH$_2$), 7.14 (d, 2H, J=8.3 Hz, Ar), 7.30-7.40 (m, 3H, Ar), 7.61 (d, 2H, J=8.3 Hz, Ar), 9.11 (s, 1H, NH).

Example 50

2-{4-[2-Amino-6-(5-chloro-2-methoxy-phenyl)-pyrimidin-4-ylamino]-phenyl}-ethanol Following the method described in Example 4,4-chloro-6-(5-chloro-2-methoxy-phenyl)-pyrimidin-2-yl-amine and 4-aminophenethyl alcohol provided the title compound (86% yield). $^1$H NMR (DMSO-d$_6$) δ 2.68 (t, 2H, J=6.9 Hz, CH$_2$), 3.57-3.61 (m, 2H, CH$_2$), 3.88 (s, 3H, CH$_3$), 4.62 (s, 1H, OH), 6.26 (s, 2H, NH$_2$), 6.72 (s, 1H, Ar), 7.12-7.18 (m, 3H, Ar), 7.43-7.45 (m, 1H, Ar), 7.63 (d, 2H, J=7.9 Hz, Ar), 7.92 (s, 1H, Ar), 9.13 (s, 1H, NH).

Example 51

6-(5-Chloro-2-methoxy-phenyl)-5-methyl-N*4*-(1H-indazol-6-yl)-pyrimidine-2,4-diamine To a stirred mixture of guanidine hydrochloride (1.91 g, 20.0 mmol) and diethyl methylmalonate (3.48 g, 20.0 mmol) in ethanol (30 ml) was added sodium methoxide (2.7 g, 50.0 mmol, 25% in methanol) dropwise. The cloudy mixture was stirred at 60-70° C. for 16 hours. After evaporation of volatiles under reduced pressure, the residue was treated with 1.0 M hydrochloric acid until pH=2. Filtration and drying provided 2-amino-4,6-dihydroxy-5-methyl-pyrimidine (2.5 g, 90% yield) as a white powder.

A mixture of 2-amino-4,6-dihydroxy-5-methyl-pyrimidine (2.0 g, 14.2 mmol) in phosphorus oxychloride (25 ml) was stirred under reflux for 4 hours. Volatiles were evaporated under reduced pressure. The residue was purified by flash chromatography on silica gel eluting with ethyl acetate-hexane (1:3) to provide 2-amino-4,6-dichloro-5-methyl-pyrimidine (0.4 g, 16% yield) as a white powder.

To a mixture of 2-amino-4,6-dichloro-5-methyl-pyrimidine (0.18 g, 1.0 mmol), 5-chloro-2-methoxy-phenyl boronic acid (0.19 g, 1.0 mmol), palladium (II) acetate (0.034 g, 0.15 mmol) and triphenylphosphine (0.079 g, 0.30 mmol) was added a solution of sodium carbonate (0.64 g, 6.0 mmol) in water (5 ml) followed by glyme (20 ml). The mixture was stirred under an argon atmosphere at room temperature for 72 hours. Filtration and concentration of the filtrate yielded a residue which was purified by flash chromatography on silica gel eluting with ethyl acetate-hexane (1:3) to provide 2-amino-4-chloro-6-(5-chloro-2-methoxyphenyl)-5-methyl-pyrimidine (0.06 g, 21% yield) as a white powder.

Following the method described in Example 4,2-amino-4-chloro-6-(5-chloro-2-methoxyphenyl)-5-methyl-pyrimidine and 1H-indazol-6-yl-amine provided the title compound (60% yield). $^1$H NMR (DMSO-d$_6$) δ 1.86 (s, 3H, CH$_3$), 3.78 (s, 3H, CH$_3$), 5.97 (s, 2H, NH$_2$), 7.13 (d, 1H, J=8.9 Hz, Ar), 7.22 (s, 1H, Ar), 7.44 (d, 2H, J=8.7 Hz, Ar), 7.64 (d, 1H, J=8.8 Hz, Ar), 7.98 (s, 2H, Ar), 8.18 (s, 1H, NH), 12.83 (s, 1H, NH).

Example 52

5-Bromo-6-(5-chloro-2-methoxy-phenyl)-N*4*-(1H-indazol-6-yl)-pyrimidine-2,4-diamine To a stirred mixture of 4,6-dichloro-pyrimidin-2-yl-amine (2.46 g, 15.0 mmol) and sodium acetate (6.15 g, 75.0 mmol) in acetic acid (150 ml) was added bromine (3.24 g, 20.25 mmol) dropwise. The mixture was then stirred at 60° C. for 2 hours. Volatiles were evaporated under reduced pressure. The residue was stirred with water (500 ml) for 1 hour, filtered, and dried under reduced pressure to provide 2-amino-4,6-dichloro-5-bromo-pyrimidine (3.2 g, 88% yield) as a white solid.

To a mixture of 2-amino-4,6-dichloro-5-bromo-pyrimidine (1.22 g, 5.0 mmol), 5-chloro-2-methoxy-phenyl boronic acid (1.03 g, 5.5 mmol), palladium (II) acetate (0.17 g, 0.75 mmol) and triphenylphosphine (0.393 g, 1.5 mmol) was added a solution of sodium carbonate (3.18 g, 30 mmol) in water (20 ml) followed by glyme (100 ml). The mixture was stirred under an argon atmosphere at room temperature for 72 hours. Filtration and concentration of the filtrate yielded a residue which was purified by flash chromatography on silica gel eluting with ethyl acetate-hexane (1:3) to provide 5-bromo-4-chloro-6-(5-chloro-2-methoxy-phenyl)-pyrimidin-2ylamine (0.40 g, 23% yield) as a beige powder.

Following the method described in Example 4, 5-bromo-4-chloro-6-(5-chloro-2-methoxy-phenyl)-pyrimidin-2ylamine and 1H-indazol-6-yl-amine provided the title compound (68% yield). $^1$H NMR (DMSO-d$_6$) δ 3.79 (s, 3H, CH$_3$), 6.46 (s, 2H, NH$_2$), 7.15 (d, 1H, J=8.9 Hz, Ar), 7.24 (d, 1H, J=2.7 Hz, Ar), 7.38 (dd, 1H, J=8.7 Hz, 1.6 Hz, Ar), 7.46 (dd, 1H, J=8.9 Hz, 2.7 Hz, Ar), 7.68 (d, 1H, J=8.6 Hz, Ar), 7.84 (s, 1H, Ar), 7.80 (s, 1H, Ar), 8.43 (s, 1H, NH), 12.93 (s, 1H, NH).

Example 53

6-(5-Chloro-2-ethoxy-phenyl)-N*4*-p-tolyl-pyrimidine-2,4-diamine

To a mixture of 4,6-dichloro-pyrimidin-2-ylamine (0.50 g, 3.0 mmol), 5-chloro-2-ethoxy-phenyl boronic acid (0.61 g, 3.0 mmol), palladium (II) acetate (0.10 g, 0.46 mmol), and triphenylphosphine (0.24 g, 0.91 mmol) was added a solution of sodium carbonate (1.6 g, 15.2 mmol) in water (5 ml) followed by glyme (20 ml). The mixture was stirred under an argon atmosphere at room temperature for 3.5 hours. Acetone (20 ml) was added and the mixture was filtered through a pad of celite under suction. The filtrated was concentrated under reduced pressure and the residue was purified by flash chromatography on silica gel eluting with 15% ethyl acetate-hexane followed by 20% ethyl acetate-hexane to provide 4-chloro-6-(5-chloro-2-ethoxy-phenyl)-pyrimidin-2-ylamine (0.625 g, 73% yield) as a white powder.

To a stirred suspension of 4-chloro-6-(5-chloro-2-ethoxy-phenyl)-pyrimidin-2-ylamine (0.030 g, 0.106 mmol) in ethanol (5 ml) was added a solution of hydrogen chloride in dioxane (4.0 M, 0.015 ml) followed by p-tolylamine (0.014 g, 0.127 mmol). After heating under reflux for 3.5 hours, the volatiles were evaporated under reduced pressure. The residue was treated with 1.0 M hydrochloric acid (10 ml) and stirred overnight. After filtration, the solid was dissolved in methanol (10 ml) and treated with aqueous sodium carbonate solution (1.0 M, 1 ml). After stirring for 0.5 hours, the volatiles were evaporated under reduced pressure, the solid was stirred with water (10 ml) for 15 minutes, and filtered to provide the title compound (0.020 g, 53% yield) as a white powder. $^1$H NMR (DMSO-d$_6$) δ 1.37 (t, 3H, J=6.8 Hz, CH$_3$), 2.27 (s, 3H, CH$_3$), 4.12 (q, 2H, J=6.6 Hz, CH$_2$), 6.25 (s, 2H, NH$_2$), 6.75 (s, 1H, Ar), 7.10-7.14 (m, 3H, Ar), 7.40-7.42 (m, 1H, Ar), 7.55 (d, 2H, J=8.0 Hz, Ar), 7.92 (s, 1H, Ar), 9.05 (s, 1H, NH).

Example 54

6-(5-Chloro-2-ethoxy-phenyl)-N*4*-(1H-indazol-6-yl)-pyrimdine-2,4-diamine

Following the method described in Example 53, 4-chloro-6-(5-chloro-2-ethoxy-phenyl)-pyrimidin-2-ylamine and 1H-indazol-6-ylamine provided the title compound (65% yield). $^1$H NMR (DMSO-d$_6$) δ 1.34 (t, 3H, J=6.9 Hz, CH$_3$), 4.13 (q, 2H, J=6.9 Hz, CH$_2$), 6.26 (s, 2H, NH$_2$), 6.85 (s, 1H, Ar), 7.14 (d, 1H, J=8.9 Hz, Ar), 7.30 (d, 1H, J=8.6 Hz, Ar), 7.41 (dd, 1H, J-8.9 Hz, 2.7 Hz, Ar), 7.65 (d, 1H, J=8.9 Hz, Ar), 7.95-7.97 (m, 3H, Ar), 9.27 (s, 1H, NH), 12.80 (s, 1H, NH).

Example 55

6-(5-Chloro-2-ethoxy-phenyl)-N*4*-(4-chloro-phenyl)-pyrimidine-2,4-diamine

Following the method described in Example 53, 4-chloro-6-(5-chloro-2-ethoxy-phenyl)-pyrimidin-2-ylamine and 4-chloro-phenylamine provided the title compound (45% yield). $^1$H NMR (DMSO-d$_6$) δ 1.39 (t, 3H, J=6.9 Hz, CH$_3$), 4.14 (q, 2H, J=6.5 Hz, CH$_2$), 6.36 (s, 2H, NH$_2$), 6.78 (s, 1H, Ar), 7.15 (d, 1H, J=8.9 Hz, Ar), 7.32 (d, 2H, J=8.9 Hz, Ar), 7.41 (dd, 1H, J=8.8, 2.8 Hz, Ar), 7.79 (d, 2H, J=8.9 Hz, Ar), 7.91 (d, 1H, J=2.8 Hz), 9.31 (s, 1H, NH).

Example 56

6-(5-Chloro-2-ethoxy-phenyl)-N*4*-(4-trifluoromethyl-phenyl)-pyrimidine-2,4-diamine Following the method described in Example 53, 4-chloro-6-(5-chloro-2-ethoxy-phenyl)-pyrimidin-2-ylamine and 4-trifluoromethyl-phenylamine provided the title compound (78% yield). $^1$H NMR (DMSO-d$_6$) δ 1.40 (t, 3H, J=6.9 Hz, CH$_3$), 4.15 (q, 2H, J=6.9 Hz, CH$_2$), 6.45 (s, 2H, NH$_2$), 6.84 (s, 1H, Ar), 7.16 (d, 1H, J=8.9 Hz, Ar), 7.43 (dd, 1H, J=8.8 Hz, 2.8 Hz, Ar), 7.61 (d, 2H, J=8.9 Hz, Ar), 7.93 (d, 1H, J=2.8 Hz, Ar), 7.99 (d, 2H, J=8.9 Hz), 9.59 (s, 1H, NH).

Example 57

4-[2-Amino-6-(5-chloro-2-ethoxy-phenyl)-pyrimidin4-ylamino]-benzonitrile

Following the method described in Example 53, 4-chloro-6-(5-chloro-2-ethoxy-phenyl)-pyrimidin-2-ylamine and 4-amino-benzonitrile provided the title compound (74% yield). $^1$H NMR (DMSO-d$_6$) δ 1.41 (t, 3H, J=6.9 Hz, CH$_3$), 4.15 (q, 2H, J=7.0 Hz, CH$_2$), 6.53 (s, 2H, NH$_2$), 6.84 (s, 1H, Ar), 7.17 (d, 1H, J-8.9 Hz, Ar), 7.43 (dd, 1H, J=8.8, 2.9 Hz, Ar), 7.71 (d, 2H, J=8.9 Hz, Ar), 7.92 (d, 1H, J=2.9 Hz, Ar), 8.00 (d, 2H, J=8.9 Hz, Ar), 9.70 (s, 1H, NH).

Example 58

6-(5-Chloro-2-ethoxy-phenyl)-N*4*-(4-methoxy-phenyl)-pyrimidine-2,4-diamine

Following the method described in Example 53, 4-chloro-6-(5-chloro-2-ethoxy-phenyl)-pyrimidin-2-ylamine and 4-methoxy-phenylamine provided the title compound (61% yield). $^1$H NMR (DMSO-d$_6$) δ 1.34 (t, 3H, J=6.9 Hz, CH$_3$), 3.74 (s, 3H, CH$_3$), 4.10 (q, 2H, J=7.0 Hz, CH$_2$), 6.18 (s, 2H, NH$_2$), 6.71 (s, 1H, Ar), 6.89 (d, 2H, J=8.6 Hz, Ar), 7.12 (d, 1H, J=8.9 Hz, Ar), 7.39 (dd, 1H, J=8.8 Hz, 2.9 Hz, Ar), 7.53 (d, 2H, J=8.6 Hz, Ar), 7.94 (d, 1H, J=2.8 Hz, Ar), 8.93 (s, 1H, NH).

Example 59

{4-[2-Amino-6-(5-bromo-2-ethoxy-phenyl)-pyrimidin4-ylamino]-phenyl}-phenyl-methanone 4-Chloro-6-(5-bromo-2-ethoxy-phenyl)-pyrimidin-2-ylamine was prepared according to the method described in Example 4 for 4-chloro-6-(5-chloro-2-methoxy-phenyl)-pyrimidin-2-ylamine. The product was dissolved in methanol (40 ml). A solution of hydrogen chloride in dioxane (4.0 M, 5 ml) was added and the solution was concentrated under reduced pressure. The residual solid was stirred with aqueous 1.0 M hydrochloric acid for 0.5 hours and filtered to provide the hydrochloride salt of 4-chloro-6-(5-bromo-2-ethoxy-phenyl)-pyrimidin-2-ylamine (1.37 g, 22% yield).

Following the method described in Example 53, the hydrochloride salt of 4-chloro-6-(5-bromo-2-ethoxy-phenyl)-pyrimidin-2-ylamine and (4-amino-phenyl)-phenyl-methanone provided the title compound (59% yield). $^1$H NMR (DMSO-d$_6$) δ 1.40 (t, 3H, J=6.9 Hz, CH$_3$), 4.16 (q, 2H, J=6.8 Hz, CH$_2$), 6.49 (s, 2H, NH$_2$), 6.88 (s, 1H, Ar), 7.12 (d, 1H, J=8.9 Hz, Ar), 7.54-7.59 (m, 3H, Ar), 7.65-7.68 (m, 1H, Ar), 7.71-7.75 (m, 4H, Ar), 8.00 (d, 2H, J=8.7 Hz, Ar), 8.06 (s, 1H, Ar) 9.70 (s, 1H, NH).

Example 60

6-(5-Bromo-2-ethoxy-phenyl)-N*4*-(4-trifuoromethyl-phenyl)-pyrimidin-2,4-diamine Following the method described in Example 14, the hydrochloride salt of 4-chloro-6-(5-bromo-2-ethoxy-phenyl)-pyrimidin-2-ylamine and 4-trifluoromethyl-phenylamine provided the title compound (86% yield). $^1$H NMR (DMSO-d$_6$) δ 1.40 (t, 3H, J=6.9 Hz, CH$_3$), 4.15 (q, 2H, J=6.8 Hz, CH$_2$), 6.45 (s, 2H, NH$_2$), 6.84 (s, 1H, Ar), 7.11 (d, 1H, J=8.9 Hz, Ar), 7.53-7.56 (m, 1H, Ar), 7.61 (d, 2H, J=8.6 Hz, Ar), 7.99 (d, 2H, J=8.5 Hz, Ar), 8.06 (s, 1H, Ar), 9.58 (s, 1H, NH).

Example 61

4-[2-Amino-6-(5-bromo-2-ethoxy-phenyl)-pyrimidin-4-ylamino]-benzoic acid methyl ester Following the method described in Example 14, the hydrochloride salt of 4-chloro-6-(5-bromo-2-ethoxy-phenyl)-pyrimidin-2-ylamine and 4-amino-benzoic acid methyl ester provided the title compound (0.056 g, 71% yield). $^1$H NMR (DMSO-d$_6$) δ 1.40 (t, 3H, J=6.9 Hz, CH$_3$), 3.83 (s, 3H, CH$_3$), 4.15 (q, 2H, J=6.9 Hz, CH$_2$), 6.46 (s, 2H, NH$_2$), 6.85 (s, 1H, Ar), 7.11 (d, 1H, J=8.9 Hz, Ar), 7.54 (dd, 1H, J=8.6 Hz, J=2.7 Hz, Ar), 7.91 (q, 4H, J=9.0 Hz, Ar), 8.05 (d, 1H, J=2.7 Hz, Ar), 9.60 (s, 1H, NH).

Example 62

{4-[2-Amino-6-(5-bromo-2-ethoxy-phenyl)-pyrimidin4-ylamino]-phenyl}-methanol

To a stirred suspension of the title compound of Example 61 (0.050 g, 0.113 mmol) in tetrahydrofuran, cooled to 0° C., was added a solution of lithium aluminum hydride in tetrahydrofuran (1 M, 0.5 ml) dropwise over 1 minute. After stirring at 0° C. for 2 hours, aqueous sodium hydroxide solution (1 M, 0.5 ml) was added and the mixture was extracted with tetrahydrofuran (3×25 ml). The combined extracts were washed with saturated aqueous sodium chloride solution and dried over magnesium sulfate. After evaporation of the solvent under reduced pressure, the residue was purified by preparative thin layer chromatography, eluting with tetrahydrofuran-chloroform (1:1) followed by tetrahydrofuran-chloroform (2:1), to provide the title compound (0.013 g, 28% yield). $^1$H NMR (DMSO-d$_6$) δ 1.38 (t, 3H, J=6.9 Hz, CH$_3$), 4.13 (q, J=6.9 Hz, 2H, CH$_2$), 4.45 (d, 2H, J=5.7 Hz, CH$_2$), 5.07 (t, 1H, J=5.6 Hz, OH), 6.28 (s, 2H, NH$_2$), 6.76 (s, 1H, Ar), 7.09 (d, 1H, J=8.9 Hz, Ar), 7.24 (d, 2H, J=8.4, Hz, Ar), 7.53 (dd, 1H, J=8.9 Hz, 2.5 Hz, Ar), 7.64 (d, 2H, J=8.3 Hz, Ar), 8.04 (s, 1H, Ar), 9.09 (s, 1H, NH).

Example 63

Succinic acid mono-{4-[2-amino-6-(5-chloro-2-ethoxy-phenyl)-pyrimidin-4-ylamino]-benzyl}-ester To a stirred suspension of the title compound of Example 44 (0.300 g, 0.809 mmol) and succinic anhydride (0.097 g, 0.971 mmol) in chloroform (10 ml) was added 4-dimethyl-amino-pyridine (0.138 g, 1.13 mmol). After stirring for 16 hours, the mixture was concentrated under reduced pressure. Water (10 ml) was added and the mixture was adjusted to pH 2 by addition of aqueous potassium hydrogen sulfate solution (0.5 M). The solid was filtered and dried under reduced pressure to provide the title compound (0.381 g, 81% yield). $^1$H NMR (DMSO-d$_6$) δ1.38 (t, 3H, J=6.9 Hz, CH$_3$), 2.48-2.50 (m, 2H, CH$_2$), 2.50-2.52 (m, 2H, CH$_2$), 4.13 (q, 2H, J=6.9 Hz, CH$_2$), 5.05 (s, 2H, CH$_2$), 6.28 (s, 2H, NH$_2$), 6.79 (s, 1H, Ar), 7.14 (d, 1H, J=8.9 Hz, Ar), 7.29 (d, 2H, J=8.9 Hz, Ar), 7.41 (dd, 1H, J=8.9 Hz, 2.9 Hz, Ar), 7.71 (d, 2H, J=8.5 Hz, Ar), 7.93 (s, 1H, Ar), 9.22 (s, 1H, NH), 12.05 (s, 1H, COOH).

Example 64

Amino acetic acid-4-[2-amino-6-(5-chloro-2-ethoxy-phenyl)-pyrimidin-4-ylamino]-benzyl ester To a stirred suspension of the title compound of Example 44 (0.400 g, 1.08 mmol), N-(tert-butoxycarbonyl)-glycine (0.227 g, 1.29 mmol) and 4-dimethyl-amino-pyridine (0.184 g, 1.51 mmol) in dichloromethane (20 ml) was added 1-[3-(dimethyl-amine)-propyl]-3-ethyl carboduimide (0.282 g, 1.51 mmol). After stirring for 6 hours, the mixture was purified by flash chromatography on silica gel eluting in ethyl acetate-hexane (2:3) to provide tert-butoxycarbonylamino-acetic acid 4-[2-amino-6-(5-chloro-2-ethoxy-phenyl)-pyrimidin-4-ylamino]-benzyl ester.

A solution of tert-butoxycarbonylamino-acetic acid 4-[2-amino-6-(5-chloro-2-ethoxy-phenyl)-pyrimidin-4-ylamino]-benzyl ester in ethyl acetate (15 ml) was treated with a solution of hydrogen chloride in dioxane (4.0 M, 15 ml). After stirring for 16 hours, the solid was filtered and dried under reduced pressure to provide the hydrochloride salt of the title compound (0.273 g, 48% yield). $^1$H NMR (DMSO-d$_6$) δ 1.39 (t, 3H, J=6.4 Hz, CH$_3$), 3.89 (d, 2H, J=4.9 Hz, CH$_2$), 4.17 (q, 2H, J=6.2 Hz, CH$_2$), 5.25 (s, 2H, CH$_2$), 6.70 (s, 1H, Ar), 7.28 (d, 1H, J=8.7 Hz, Ar), 7.46 (d, 2H, J=8.4 Hz, Ar), 7.62-7.67 (m, 2H, Ar), 7.88 (d, 2H, J=7.4 Hz, Ar), 8.37 (s, 3H), 11.10 (s, 1H), 12.68 (s, 1H).

Example 65

{4-[6-(5-Chloro-2-ethoxy-phenyl)-2-methylamino-pyrimidin4-ylamino]-phenyl}-methanol To a stirred mixture of 4,6-dichloro-pyrimidin-2-ylamine (5.0 g, 30.5 mmol) and pyridine (2.6 ml, 32 mmol) in dichloromethane (100 ml), cooled in an ice bath, was added trifluoroacetic anhydride (4.5 ml, 32 mmol). After stirring at room temperature for 1 hour, the mixture was diluted with dichloromethane (100 ml) and washed with cold saturated sodium chloride solution (100 ml) and dried over sodium sulfate. Concentrating under reduced pressure provided N-(4,6-dichloro-pyrimidin-2-yl)-2,2,2-trifluoro-acetamide (7.9 g, 100% yield).

To a mixture of N-(4,6-dichloro-pyrimidin-2-yl)-2,2,2-trifluoro-acetamide (4.6 g, 17.7 mmol) and potassium carbonate (4.9 g, 35.4 mmol) in acetone (100 ml) was added iodomethane (1.3 ml, 21.2 mmol). After stirring for 12 hours, the mixture was filtered through a pad of celite under suction. The filtrate was concentrated under reduced pressure and the residue was treated with methanol (150 ml) tetrahydrofuran (30 ml), and a solution of potassium carbonate (5.0 g, 51 mmol) in water (15 ml). After stirring for 1 hour, the mixture was concentrated under reduced pressure. The residue was partitioned between ethyl acetate (150 ml) and saturated aqueous sodium chloride solution (100 ml). The organic phase was dried over magnesium sulfate. After evaporation of the solvent under reduced pressure, the residue was purified by flash chromatography eluting with ethyl acetate-hexane (1:6 followed by 1:4) to give N-(4,6-dichloro-pyrimidin-2-yl)-methyl-amine (2.7 g, 85% yield). $^1$H NMR (CDCl$_3$) δ 3.04 (d, 3H, J=5.1 Hz, CH$_3$), 5.50 (br s, 1H, NH), 6.63 (s, 1H, Ar).

To an argon saturated solution of N-(4,6-dichloro-pyrimidin-2-yl)-methyl-amine (200 mg, 1.1 mmol), 5-chloro-2-ethoxy-phenylboronic acid (248 mg, 1.21 mmol) and palladium acetate (38 mg, 0.16 mmol) in dimethyl ethylene glycol (20 ml) was added a solution of sodium carbonate (240 mg, 2.2 mmol) in water (5 ml) followed by triphenylphosphine (66 mg, 0.33 mmol). After stirring at 70° C. under an argon atmosphere for 60 hours, the mixture was filtered through a pad of celite under suction and the filtrate was dried over magnesium sulfate. Evaporation of the solvent under reduced pressure provided [4-chloro-6-(5-chloro-2-ethoxy-phenyl)-pyrimidin-2-yl]-methyl-amine (300 mg, 90% yield).

A mixture of [4-chloro-6-(5-chloro-2-ethoxy-phenyl)-pyrimidin-2-yl]-methyl-amine (260 mg, 0.87 mmol), 4-aminobenzoic acid ethyl ester (300 mg, 2.0 mmol), a solution of hydrogen chloride in 1,4-dioxane (4 M, 1 ml), and ethanol (20 ml) was heated under reflux for 5 hours. After concentrating under reduced pressure, the residue was stirred with hydrochloric acid (1 M, 15 ml) for 30 minutes. The solid was filtered and treated with a solution of sodium carbonate (5.0 g) in water (15 ml). After stirring for 30 minutes, the solid was filtered and dried under reduced pressure for 12 hours to yield 4-[6-(5-chloro-2-ethoxy-phenyl)-2-methylamino-pyrimidin-4-ylamino]-benzoic acid sodium salt (300 mg, 87% yield). $^1$H NMR (DMSO-d$_6$) δ 1.38 (t, 3H, J=6.9 Hz, CH$_3$), 2.95 (br s, 3H, CH$_3$), 4.16 (q, 2H, J=7.0 Hz, CH$_2$), 6.85 (br s, 1H, Ar), 7.23 (d, 1H, J=8.6 Hz, Ar), 7.56 (br s, 1H, Ar), 7.78 (br s, 1H, Ar), 7.97 (br s, 4H, Ar).

To a mixture of 4-[6-(5-chloro-2-ethoxy-phenyl)-2-methylamino-pyrimidin-4-ylamino]-benzoic acid sodium salt (100 mg, 0.25 mmol) in tetrahydofuran (20 ml) was added lithium aluminum hydide (100 mg, 2.63 mmol) in 10 portions at room temperature. After stirring for 1 hour, methanol (5 ml) was carefully added followed by hydrochloric acid (1 M, 10 ml). After stirring for 10 minutes, the mixture was filtered. The filtrate was concentrated under reduced pressure and the residue was treated with methanol (5 ml) and a solution of sodium carbonate (5.0 g) in water (15 ml). The mixture was concentrated under reduced pressure to remove methanol. Filtration and drying of the solid under reduced pressure for 12 hours yielded the title compound (80 mg, 83% yield). $^1$H NMR (DMSO-d$_6$) δ 1.39 (t, 3H, J=6.93 Hz, CH$_3$), 2.86 (d, 3H, J=4.7 Hz, OH), 4.13 (q, 2H, J=7.0 Hz, CH$_2$), 4.45 (d, 2H, J=5.7 Hz, CH$_2$), 5.07 (t, 1H, J=5.7 Hz, CH$_2$), 6.75 (br s, 2H, Ar), 7.14 (d, 1H, J=8.9 Hz, Ar), 7.24 (d, 2H, J=8.5 Hz, Ar), 7.40 (dd, 1H, J=8.8 Hz, J=2.8 Hz, Ar), 7.67 (d, 2H, J=8.3 Hz, Ar), 7.93 (s, 1H, NH), 9.17 (s, 1H, NH).

Example 66

6-(5-Chloro-2-ethoxy-phenyl)-N*4*-(4-oxazol-5-yl-phenyl)-pyrimidine-2,4-diamine

A mixture of 4-nitro-benzaldehyde (5.0 g, 33.1 mmol), tosylmethyl isocyanide (6.4 g, 33.1 mmol) and potassium carbonate (7.8 g, 82.7 mmol) in methanol (100 ml) was heated under reflux for 30 minutes. After concentrating under reduced pressure, the residue was stirred with water (50 ml). The solid that was filtered to afford 5-(4-nitro-phenyl)-oxazole (5.6 g, 89% yield). $^1$H NMR (acetone-d$_6$) δ 7.89 (s, 1H, Ar), 8.05 (d, 2H, J=9.3 Hz, Ar), 8.35-8.38 (m, 3H, Ar).

A mixture of 5-(4-nitro-phenyl)-oxazole (2.0 g, 10.5 mmol), iron powder (2.4 g, 42.8 mmol) in acetic acid (5 ml) and methanol (30 ml) was stirred at 60° C. for 1 hour. After filtration through a pad of celite under suction, the filtrate was concentrated under reduced pressure. The residue was purified by flash chromatography eluting with ethyl acetate-hexane (3:4 followed by 3:2) to give 4-oxazol-5-yl-phenyl-amine (1.4 g, 83% yield). $^1$H NMR (acetone-d$_6$) δ 5.0 (br s, 2H, NH), 6.76 (d, 2H, J=8.7 Hz, Ar), 7.12 (s, 1H, Ar), 7.45 (d, 2H, J=8.6 Hz, Ar), 8.04 (s, 1H, Ar).

To a mixture of 4-chloro-6-(5-chloro-2-ethoxy-phenyl)-pyrimidin-2-ylamine (100 mg, 0.37 mmol) and ethanol (20 ml) was added a solution of hydrogen chloride in 1,4-dioxane (4 M, 0.1 ml). After stirring for 10 minutes, 4-oxazol-5-yl-phenyl-amine (60 mg, 0.37 mmol) was added and the mixture was heated under reflux for 5 hours. After concentrating under reduced pressure, the residue was stirred with ethyl acetate (10 ml) and saturated aqueous sodium bicarbonate solution (10 ml). The solid was filtered and purified by flash chromatography eluting with ethyl acetate-hexane (1:1 followed by 3:2) to yield the title compound (110 mg, 75% yield). $^1$H NMR (acetone-d$_6$) δ 1.44 (t, 3H, J=7.0 Hz, CH$_3$), 4.17 (q, 2H, J=7.0 Hz, CH$_2$), 5.88 (br s, 2H, NH), 7.04 (s, 1H, Ar), 7.12 (d, 1H, J=8.5 Hz, Ar), 7.37 (dd, 1H, J=8.8 Hz, J=2.9 Hz, Ar), 7.46 (s, 1H, Ar), 7.68 (d, 2H, J=8.7 Hz, Ar), 7.88-7.91 (m, 2H, Ar), 8.07 (d, 1H, J=2.8 Hz, Ar), 8.16 (s, 1H, Ar), 8.64 (br s, 1H, NH).

Example 67

(S)-2-Amino-succinic acid 4-{4-[2-amino-6-(5-chloro-2-ethoxy-phenyl)-pyrimidin4-ylamino]-benzyl} ester (S)-2-tert-Butoxycarbonylamino-succinic acid 4-{4-[2-amino-6-(5-chloro-2-ethoxy-phenyl)-pyrimidin-4-ylamino]-benzyl} ester 1-tert-butyl ester was prepared according to the method described for Example 64 by using the title compound of Example 44 and 2-tert-butoxycarbonylamino-succinic acid 1-tert-butyl ester.

Following the method described in Example 64, (S)-2-tert-butoxycarbonylamino-succinic acid 4-{4-[2-amino-6-(5-chloro-2-ethoxy-phenyl)-pyrimidin-4-ylamino]-benzyl} ester 1-tert-butyl ester and hydrogen chloride provided the title compound (69% yield). $^1$H NMR (DMSO-d$_6$) δ 1.39 (t, 3H, J=7.0 Hz, CH$_3$), 3.00-3.03 (m, 2H, CH$_2$), 4.17 (q, 2H, J=6.9 Hz, CH$_2$), 4.24 (s, 1H, CH), 5.16 (s, 2H, CH$_2$), 6.74 (s, 1H, Ar), 7.28 (d, 1H, J=8.9 Hz, Ar), 7.43 (d, 2H, J=8.4 Hz, Ar), 7.61-7.68 (m, 2H, Ar), 7.88 (d, 2H, J=8.0 Hz, Ar), 8.52 (s, 3H), 11.23 (s, 1H), 12.77 (s, 1H).

Example 68

2-Amino-propionic acid 4-[2-amino-6-(5-chloro-2-ethoxy-phenyl)-pyrimidin-4-ylamino]-benzyl ester (S)-2-tert-Butoxycarbonylamino-propionic acid 4-[2-amino-6-(5-chloro-2-ethoxy-phenyl)-pyrimidin-4-ylamino]-benzyl ester was prepared according to the method described for Example 64 by using the title compound of Example 44 and 2-tert-butoxycarbonylamino-propionic acid. Following the method described in Example 64, (S)-2-tert-butoxycarbonylamino-propionic acid 4-[2-amino-6-(5-chloro-2-ethoxy-phenyl)-pyrimidin-4-ylamino]-benzyl ester and hydrogen chloride provided the title compound (51% yield).
$^1$H NMR (DMSO-$d_6$) δ 1.37-1.45 (m, 6H, CH$_3$), 4.14-4.18 (m, 2H, CH$_2$), 5.25 (s, 2H, CH$_2$), 6.72 (s, 1H, Ar), 7.28 (d, 1H, J=8.9 Hz, Ar), 7.46 (d, 2H, J=8.3 Hz, Ar), 7.62-7.67 (m, 2H, Ar), 7.89 (d, 2H, J=7.5 Hz, Ar), 8.50 (s, 3H), 11.20 (s, 1H), 12.75 (s, 1H).

Example 69

Succinic acid mono-(2-{4-[2-amino-6-(5-chloro-2-ethoxy-phenyl)-pyrimidin4-ylamino]-phenyl}-ethyl) ester Following the method described in Example 63, the title compound of Example 47 and succinic anhydride provided the title compound (96% yield). $^1$H NMR (MeOH-$d_4$) δ 1.42 (t, 3H, J=7.0 Hz, CH$_3$), 2.57-2.58 (m, 4H, CH$_2$), 2.57 (t, 2H, J=7.0 Hz, CH$_2$), 4.16 (q, 2H, J=6.9 Hz, CH$_2$), 4.30 (t, 2H, J=6.8 Hz, CH$_2$), 6.50 (s, 1H, Ar), 7.15 (d, 1H, J=8.9 Hz, Ar), 7.29 (d, 2H, J=8.4 Hz, Ar), 7.47 (dd, 1H, J=8.9 Hz, J=2.7 Hz, Ar), 7.60-7.64 (m, 3H, Ar).

Example 70

2-{4-[2-Amino-6-(5-bromo-2-ethoxy-phenyl)-pyrimidin-4-ylamino]-phenyl}-ethanol Following the method described in Example 4, 4-chloro-6-(5-bromo-2-ethoxy-phenyl)-pyrimidin-2-yl-amine and 4-aminophenethyl alcohol provided the title compound (95% yield). $^1$H NMR (DMSO-$d_6$) δ 1.36 (t, 3H, J=7.0 Hz, CH$_3$), 2.68 (t, 2H, J=7.0 Hz, CH$_2$), 3.55-3.60 (m, 2H, CH$_2$), 4.11 (q, 2H, J=6.8 Hz, CH$_2$), 4.61 (t, 1H, J=5.2 Hz, OH), 6.23 (s, 2H, NH$_2$), 6.75 (s, 1H, Ar), 7.07 (d, 1H, J=8.9 Hz, Ar), 7.13 (d, 2H, J=8.3 Hz, Ar), 7.49-7.56 (m, 3H, Ar), 8.05 (d, 1H, J=2.6 Hz, Ar), 9.04 (s, 1H, NH).

Example 71

N*4*-(4-Chloro-phenyl)-6-(5-methoxy-2-methyl-phenyl)-pyrimidine-2,4-diamine

4-Chloro-6-(5-methoxy-2-methyl-phenyl)-pyrimidin-2-yl-amine was prepared according to the method described in Example 4 for 4-chloro-6-(5-chloro-2-methoxy-phenyl)-pyrimidine-2-yl-amine.
Following the method described in Example 4, 4-chloro-6-(5-methoxy-2-methyl-phenyl)-pyrimidin-2-yl-amine and 4-chloro-aniline provided the title compound as hydrochloride salt (75% yield). $^1$H NMR (DMSO-$d_6$) δ 2.25 (s, 3H, CH$_3$), 3.79 (s, 3H, CH$_3$), 6.33 (s, 1H, Ar), 7.05-7.09 (m, 2H, Ar), 7.33 (d, 1H, J=8.3 Hz, Ar), 7.46 (d, 2H, J=8.8 Hz, Ar), 7.87 (d, 2H, J=7.4 Hz, Ar), 10.85 (s, 1H), 12.70 (s, 1H).

Example 72

2-[2-Amino-6-(4-chloro-phenylamino)-pyrimidin-4-yl]-4-bromo-phenol

To a stirred suspension of 4-(5-bromo-2-ethoxy)-phenyl)-6-chloro-pyrimidin-2-ylamine (0.493 g, 1.5 mmol) in dichloromethane was added boron tribromide (1.0 M in dichloromethane, 8.0 ml, 8.0 mmol) dropwise. After stirring at room temperature for 16 hours, volatiles were evaporated under reduced pressure. The residue was treated with water (100 ml) and stirred for 1 hour. Filtration provided 2-(2-amino-6-chloro-pyrimidin-4-yl)-4-bromo-phenol (0.30 g, 67% yield) as a yellow powder.
Following the method described in Example 4, 2-(2-amino-6-chloro-pyrimidin-4-yl)-4-bromo-phenol and 4-chloro-aniline provided the title compound (93% yield). $^1$H NMR (DMSO-$d_6$) δ 6.55 (s, 1H, Ar), 6.84 (d, 1H, J=8.8 Hz, Ar), 6.98 (s, 2H, NH$_2$), 7.32-7.35 (m, 2H, Ar), 7.44 (dd, 1H, J=8.8 Hz, J=2.5 Hz, Ar), 7.75 (d, 1H, J=2.5 Hz, Ar), 7.79-7.81 (m, 2H, Ar), 9.49 (s, 1H, NH), 14.50 (s, 1H).

Example 73

N*4*-(4-Chloro-phenyl)-6-(2,5-dimethyl-phenyl)-pyrimidine-2,4-diamine

4-Chloro-6-(2,5-dimethyl-phenyl)-pyrimidin-2-yl-amine was prepared according to the method described in Example 4 for 4-chloro-6-(5-chloro-2-methoxy-phenyl)-pyrimidine-2-yl-amine.
Following the method described in Example 4, 4-chloro-6-(2,5-dimethyl-phenyl)-pyrimidin-2-yl-amine and 4-chloro-aniline provided the title compound (82% yield). $^1$H NMR (DMSO-$d_6$) δ 2.29 (s, 3H, CH$_3$), 2.31 (s, 3H, CH$_3$), 6.06 (s, 1H, Ar), 6.34 (s, 2H, NH$_2$), 7.05-7.16 (m, 3H, Ar), 7.30 (d, 2H, J=8.9 Hz, Ar), 7.80 (d, 2H, J=8.9 Hz, Ar), 9.27 (s, 1H, NH).

Example 74

2-{4-[2-Amino-6-(2,5-dimethyl-phenyl)-pyrimidin-4-ylamino]-phenyl}-ethanol

Following the method described in Example 4, 4-chloro-6-(2,5-dimethyl-phenyl)-pyrimidin-2-yl-amine and 4-aminophenethyl alcohol provided the title compound as hydrochloride salt (85% yield). $^1$H NMR (DMSO-$d_6$) δ 2.29 (s, 6H, CH$_3$), 6.30 (s, 1H, Ar), 7.24-7.31 (m, 5H, Ar), 7.68 (d, 2H, J=8.0 Hz, Ar), 10.67 (s, 1H), 12.54 (s, 1H).

Example 75

5-[2-Amino-6-(5-bromo-2-methyl-phenyl)-pyrimidin-4-ylamino]-2-chloro-N-methyl-benzamide Following the method described in Example 4, 4-chloro-6-(5-bromo-2-methyl-phenyl)-pyrimidin-2-yl-amine and 5-amino-2-chloro-N-methyl-benzamide provided the title compound as hydrochloride salt (90% yield). $^1$H NMR (DMSO-$d_6$) δ 2.34 (s, 3H, CH$_3$), 2.78 (d, 3H, J=4.6 Hz, CH$_3$), 6.39 (s, 1H, Ar), 7.39 (d, 1H, J=8.9 Hz, Ar), 7.50 (d, 1H, J=8.8 Hz, Ar), 7.68-7.70 (m, 2H, Ar), 7.80 (s, 1H, Ar), 7.95 (s, 1H, Ar), 8.35-8.38 (m, 1H, NH), 10.95 (s, 1H), 12.80 (s, 1H).

Example 76

**6-(5-Fluoro-2-methyl-phenyl)-N*4*-(4-trifluoromethyl-phenyl)-pyrimidine-2,4-diamine**

4-Chloro-6-(5-fluoro-2-methyl-phenyl)-pyrimidin-2-yl-amine was prepared according to the method described in Example 4 for 4-chloro-6-(5-chloro-2-methoxy-phenyl)-pyrimidine-2-yl-amine.

Following the method described in Example 4,4-chloro-6-(5-fluoro-2-methyl-phenyl)-pyrimidin-2-yl-amine and 4-trifluoromethyl-aniline provided the title compound as hydrochloride salt (87% yield). $^1$H NMR (DMSO-$d_6$) δ 2.37 (s, 3H, $CH_3$), 6.49 (s, 1H, Ar), 7.30-7.40 (m, 2H, Ar), 7.45-7.48 (m, 1H, Ar), 7.45 (d, 2H, J=8.6 Hz, Ar), 8.08 (s, 2H, J=7.2 Hz, Ar), 11.20 (s, 1H), 13.05 (s, 1H).

Example 77

5-[2-Amino-6-(5-chloro-2-methyl-phenyl)-pyrimidin4-ylamino]-2-bromo-N-methyl-benzamide

Following the method described in Example 4,4-chloro-6-(5-chloro-2-methyl-phenyl)-pyrimidin-2-yl-amine and 5-amino-2-bromo-N-methyl-benzamide provided the title compound as hydrochloride salt (78% yield). $^1$H NMR (DMSO-$d_6$) δ 2.35 (s, 3H, $CH_3$), 2.78 (d, 3H, J=4.5 Hz, $CH_3$), 6.35 (s, 1H, Ar), 7.45 (d, 1H, J=7.9 Hz, Ar), 7.55-7.58 (m, 2H, Ar), 7.64 (d, 1H, J=8.6 Hz, Ar), 7.77 (s, 1H, Ar), 7.86 (s, 1H, Ar), 8.35-8.38 (m, 1H, NH), 10.90 (s, 1H), 12.60 (s, 1H).

Example 78

5-[2-Amino-6-(5-bromo-2-methyl-phenyl)-pyrimidin-4-ylamino]-2-bromo-N-methyl-benzamide

Following the method described in Example 4,4-chloro-6-(5-bromo-2-methyl-phenyl)-pyrimidin-2-yl-amine and 5-amino-2-bromo-N-methyl-benzamide provided the title compound as the hydrochloride salt (66% yield). $^1$H NMR (MeOH-$d_4$) δ 2.37 (s, 3H, $CH_3$), 2.94 (d, 3H, J=4.7 Hz, $CH_3$), 6.28 (s, 1H, Ar), 7.34-7.36 (m, 1H, Ar), 7.63-7.67 (m, 3H, Ar), 7.73-7.78 (m, 1H, Ar), 7.93 (s, 1H, Ar), 8.40-8.50 (m, 1H, NH).

Example 79

5-[2-Amino-6-(5-chloro-2-methyl-phenyl)-pyrimidin4-ylamino]-isoindole-1,3-dione

Following the method described in Example 4,4-chloro-6-(5-chloro-2-methyl-phenyl)-pyrimidin-4-yl-amine and 5-amino-isoindole-1,3-dione provided the title compound as hydrochloride salt (60% yield). $^1$H NMR (DMSO-$d_6$) δ 2.38 (s, 3H, $CH_3$), 6.54 (s, 1H, Ar), 7.46 (d, 1H, J=8.2 Hz, Ar), 7.57-7.60 (m, 2H, Ar), 7.83 (d, 1H, J=8.2 Hz, Ar), 8.23 (d, 1H, J=8.1 Hz, Ar), 8.30 (s, 1H, Ar), 11.33 (s, 1H), 11.46 (s, 1H), 13.00 (s, 1H).

Example 80

N-[4-(5-Chloro-2-methyl-phenyl)-6-(4-trifluoromethyl-phenylamino)-pyrimidin-2-yl]-succinamic acid

A mixture of the title compound of Example 29 (0.19 g, 0.50 mmol) and succinic anhydride (0.30 g, 3.0 mmol) in toluene (18 ml) was heated under reflux for 6 hours. After cooled to room temperature, the mixture was filtered. The filtrate was washed with saturated aqueous sodium bicarbonate solution (3×10 ml), dried over magnesium sulfate, and concentrated under reduced pressure to provide 1-[4-(5-chloro-2-methyl-phenyl)-6-(4-trifluoromethyl-phenylamino)-pyrimidin-2-yl]-pyrrolidine-2,5-dione as a white solid (96% yield).

To a stirred solution of 1-[4-(5-chloro-2-methyl-phenyl)-6-(4-trifluoromethyl-phenylamino)-pyrimidin-2-yl]-pyrrolidine-2,5-dione (0.15 g, 0.33 mmol), tetrahydrofuran (15 ml), and water (15 ml), cooled in an ice bath, was added aqueous sodium hydroxide solution (0.25 M, 4.0 ml, 1.0 mmol) dropwise. After stirring for 1 hour, hydrochloric acid (0.25 M, 8.0 ml, 2.0 mmol) was added dropwise. Evaporation of the tetrahydrofuran under reduced pressure and filtration provided the title compound as hydrochloride salt (93% yield). $^1$H NMR ($CD_3OD$) δ 2.48 (s, 3H, $CH_3$), 2.73-2.76 (m, 2H, $CH_2$), 2.89-2.92 (m, 2H, $CH_2$), 6.81 (s, 1H, Ar), 7.45 (d, 1H, J=8.3 Hz, Ar), 7.54 (dd, 1H, J=8.3 Hz, J=2.2 Hz, Ar), 7.60 (d, 1H, J=2.2 Hz, Ar), 7.76 (d, 2H, J=8.6 Hz, Ar), 8.04 (d, 2H, J=7.9 Hz, Ar).

Example 81

[6-(5-Bromo-2-methyl-phenyl)-(4-azido-phenyl)-pyrimidine]-2,4-diamine

2-Methyl-5-bromo-iodobenzene was synthesized according to the method described by Lulinski, P., Skulski, L., *Bull. Chem. Soc. Jpn.* 2000 73:951-956. To a mixture of acetic acid (100 ml) and acetic anhydride (50 ml), cooled in an ice bath, was added sodium periodate (15.4 g, 72 mmol) and iodine (12.2 g, 48 mmol). While stirring vigorously, concentrated sulfuric acid (21 ml) was added slowly followed by 4-bromo-toluene (23.1 g, 135 mmol). After stirring for 2 hours, the ice bath was removed and the mixture was protected from light. After stirring for 16 hours, the mixture was poured into a mixture of 10% aqueous sodium sulfite solution (250 ml) and ice (250 g), and extracted with dichloromethane (3×100 ml). The combined extracts were washed with water (100 ml), dried over sodium sulfate, and concentrated under reduced pressure. The residual oil was purified by distillation (87-92° C., 1 mm) to provide 2-methyl-5-bromo-iodobenzene (28.2 g, 70% yield) as colorless oil. $^1$H NMR (DMSO-$d_6$) δ 7.99 (s, 1H), 7.50 (d, J=8.1 Hz, 1H), 7.28 (d, J=8.1 Hz, 1H), 2.33 (s, 3H).

To a solution of 2-methyl-5-bromo-iodobenzene (12 g, 40.4 mmol) in tetrahydrofuran (75 ml), cooled to −78° C., was added a solution of isopropylmagnesium chloride (4.6 g, 44.5 mmol) in tetrahydrofuran (22.2 ml) dropwise over 20 minutes. After stirring at −78° C. for 30 minutes, the mixture was warmed slowly to −20° C. and stirred for 1 hour. After cooling again to −78° C., trimethylborate (8.4 g, 80.8 mmol) was added dropwise. After warming to 0° C., the mixture was stirred for 2 hours, treated with 1 M hydrochloric acid (35 ml), and extracted with ethyl acetate (2×50 ml). The combined extracts were washed with water (50 ml), dried over sodium sulfate, and concentrated under reduced pressure. The residual solid was suspended in hexane (50 ml), filtered, washed with hexane (30 ml) and dried under reduced pressure to provide 2-methyl-5-bromo-phenylboronic acid (7.32 g, 84% yield) as a white solid. $^1$H NMR (DMSO-$d_6$) δ 7.92 (s, 1H), 7.46 (d, J=8.1 Hz, 1H), 7.13 (d, J=8.1 Hz, 1H), 2.59 (s, 3H).

To a mixture of 2-methyl-5-bromo-phenylboronic acid (7.0 g, 32.6 mmol), 2-amino-4,6-dichloropyrimidine (6.95 g, 42.4 mmol), and degassed ethylene glycol dimethyl ether (150 ml) was added a solution of sodium carbonate (17.3 g, 163 mmol) in water (50 ml). The mixture was stirred vigorously and palladium acetate (0.73 g, 3.26 mmol) was added followed by triphenylphosphine (1.71 g, 6.52 mmol). After stirring for 16 hours, the mixture was diluted with water (100 ml) and extracted with ethyl acetate (3×100 ml). The combined extracts were washed with water (100 ml), dried over sodium sulfate, and concentrated under reduced pressure. The residue was purified by flash chromatography on silica gel eluting with ethyl acetate-hexane (1:4) to provide 2-amino-4-chloro-6-(2-methyl-5-bromo-phenyl)-pyrimidine (7.8 g, 80% yield) as a pale yellow powder. $^1$H NMR (DMSO-$d_6$) δ 7.58 (d, J=2.0 Hz, 1H), 7.55 (dd, J=2.0, 8.1 Hz, 1H), 7.28 (d, J=8.1 Hz, 1H), 7.26 (br s, 2H), 6.86 (s, 1H), 2.32 (s, 3H).

To a mixture of 2-amino-4-chloro-6-(2-methyl-5-bromo-phenyl)-pyrimidine (85 mg, 0.25 mmol) and 4-azidoaniline hydrochloride (51 mg, 0.30 mmol) in anhydrous 1,4-dioxane (3 ml) was added a solution of hydrogen chloride in dioxane (4 M, 0.4 ml). After heating at 80° C. for 16 hours, the mixture was concentrated under reduced pressure. The residue was treated with water (10 ml) followed by aqueous sodium bicarbonate solution (1 M, 3 ml) and extracted with ethyl acetate (2×15 ml). The combined extracts were washed with water (10 ml), dried over sodium sulfate, and concentrated under reduced pressure. The residue was purified by preparative TLC eluting with 3% methanol-dichloromethane to yield the title compound (42 mg, 42% yield). $^1$H NMR (CDCl$_3$) δ 7.46 (d, J=2.0 Hz, 1H), 7.38 (dd, J=2.0, 8.1 Hz, 1H), 7.33 (d, J=8.8 Hz, 2H), 7.09 (d, J=8.1 Hz, 1H), 7.05 (br s, 1H), 7.01 (d, J=8.8 Hz, 2H), 6.04 (s, 1H), 5.16 (br s, 2H), 2.31 (s, 3H).

Example 82

6-(5-Bromo-2-methyl-phenyl)-N*4*-(4-trifluoromethyl-phenyl)-pyrimidine-2,4-diamine A mixture of 3-iodo-4-methyl-phenylamine (5.0 g, 21 mmol) and 48% hydrobromic acid (30 ml) was heated at 90° C. for 30 minutes. After cooling in an ice bath, a solution of sodium nitrite (1.7 g, 25.2 mmol) in water (5 ml) was added and stirred for 15 minute. This mixture was added to a mixture of copper bromide (I) (3.6 g, 25.2 mmol), 48% hydrobromic acid (20 ml) and ice (50 g) cooled in an ice bath. After stirring for 20 minutes, the mixture was heated at 90° C. for 1 hour. After stirring at room temperature for 16 hours, the mixture was treated with water (350 ml) and extracted with dichloromethane (100 ml). The organic layer was washed with saturated aqueous sodium bicarbonate solution (100 ml), washed with saturated aqueous sodium chloride solution (100 ml), dried over magnesium sulfate, and concentrated under reduced pressure. The residue was purified by flash chromatography eluting with hexane to give 5-bromo-2-methyl-1-iodo-benzene (4.4 g, 71% yield). $^1$H NMR (acetone-$d_6$) δ 2.40 (s, 3H, CH$_3$), 7.30 (d, 1H, J=8.2 Hz, Ar), 7.50 (dd, 1H, J=8.2 Hz, J=2.0 Hz, Ar), 8.00 (d, 1H, J=2.0 Hz, Ar).

4-(5-Bromo-2-methyl-phenyl)-6-chloro-pyrimidin-2-ylamine) was synthesized in 2 steps from 5-bromo-2-methyl-1-iodo-benzene as described in Example 81.

Following the method described in Example 26, 4-(5-bromo-2-methyl-phenyl)-6-chloro-pyrimidin-2-ylamine and 4-trifluoromethyl-phenylamine provided the title compound (80% yield). $^1$H NMR (acetone-$d_6$) δ 2.39 (s, 3H, CH$_3$), 6.03 (br s, 2H, NH$_2$), 6.28 (s, 1H, Ar), 7.24 (d, 1H, J=8.2 Hz, Ar), 7.48 (dd, 1H, J=8.2 Hz, J=2.0 Hz, Ar), 7.59-7.62 (m, 3H, Ar), 8.06 (d, 2H, J=8.6 Hz, Ar), 8.86 (s, 1H, NH).

Example 83

3-(4-{4-[2-Amino-6-(5-chloro-2-methyl-phenyl)-pyrimidin-4-ylamino]-phenyl}-oxazol-2-yl)-propionic acid To a mixture of 2-bromo-1-(4-nitro-phenyl)-ethanone (2.0 g, 8.2 mmol) in tetrahydrofuran (15 ml) and ethanol (15 ml) was added a solution of sodium azide (586 mg, 9.8 mmol) in water (1.5 ml). After stirring for 20 minutes, the mixture was concentrated under reduced pressure. The residue was treated with saturated aqueous sodium chloride solution (200 ml) and extracted with ethyl acetate (200 ml). The organic layer was dried over magnesium sulfate and concentrated under reduced pressure to give crude 2-azido-1-(4-nitrophenyl)-ethanone.

To a mixture of crude 2-azido-1-(4-nitrophenyl)-ethanone (8.2 mmol) and 1,2,-dichloroethane (80 ml) was added 3-chlorocarbonyl-propionic acid methyl ester (1.1 ml, 9.0 mmol) and triphenylphosphine (2.4 g, 9.0 mmol). The mixture was stirred at 85° C. for 12 hours. After cooling to room temperature, the mixture was purified by flash chromatography on silica gel eluting with ethyl acetate-hexane (1:4 followed by 1:1) to give 3-[5-(4-nitro-phenyl)-oxazol-2-yl]-propionic acid methyl ester (520 mg, 23% yield for 2 steps). $^1$H NMR (acetone-$d_6$) δ 2.92 (t, 2H, J=7.1 Hz, CH$_2$), 3.19 (t, 2H, J=7.1 Hz, CH$_2$), 3.68 (s, 3H, CH$_3$), 7.74 (s, 1H, Ar), 7.98 (d, 2H, J=9.0 Hz, Ar), 8.34 (d, 2H, J=9.0 Hz, Ar).

Following the method described in Example 66 for the synthesis of 4-oxazol-5-yl-phenylamine 3-[5-(4-nitro-phenyl)-oxazol-2-yl]-propionic acid methyl ester was converted to 3-[4-(4-amino-phenyl)-oxazol-2-yl]-propionic acid methyl ester (70% yield). $^1$H NMR (acetone-$d_6$) δ 2.85 (t, 2H, J=7.2 Hz, CH$_2$), 3.08 (t, 2H, J=7.2 Hz, CH$_2$), 3.67 (s, 3H, CH$_3$), 4.94 (bs, 2H, NH$_2$), 6.73 (d, 2H, J=8.7 Hz, Ar), 7.08 (s, 1H, Ar), 7.39 (d, 2H, J=8.7 Hz, Ar).

Following the method described in Example 26, 4-(5-chloro-2-methyl-phenyl)-6-chloro-pyrimidin-2-ylamine and 3-[4-(4-amino-phenyl)-oxazol-2-yl]-propionic acid methyl ester provided 3-(4-{4-[2-amino-6-(5-chloro-2-methyl-phenyl)-pyrimidin-4-ylamino]-phenyl}-oxazol-2-yl)-propionic acid methyl ester.

A mixture of 3-(4-{4-[2-amino-6-(5-chloro-2-methyl-phenyl)-pyrimidin-4-ylamino]-phenyl}-oxazol-2-yl)-propionic acid methyl ester (106 mg, 0.21 mmol), methanol (15 ml), and a solution of sodium hydroxide (500 mg, 12.5 mmol) in water (10 ml) was heated to 70° C. for 2 hours. After cooled to room temperature, the reaction mixture was neutralized to pH=1 using concentrated hydrochloric acid. Solid was collected via filtration and dried to give title compound in its hydrochloric acid salt form, (106 mg, 64% in two steps). $^1$H NMR (DMSO-$d_6$) δ 2.40 (s, 3H, CH$_3$), 2.76 (t, 2H, J=7.0 Hz, CH$_2$), 3.04 (t, 2H, J=7.0 Hz, CH$_2$), 6.57 (br s, 2H, NH$_2$), 7.44 (d, 1H, J=8.2 Hz, Ar), 7.53-7.57 (m, 3H, Ar), 7.67 (d, 2H, J=8.7 Hz, Ar), 7.94-8.00 (m, 2H, Ar).

Example 84

6-(5-Bromo-2-methyl-phenyl)-N*4*-(4-chloro-phenyl)-pyrimidine-2,4-diamine

Following the method described in Example 26, 4-(5-bromo-2-methyl-phenyl)-6-chloro-pyrimidin-2-ylamine and 4-chloro-phenylamine provided the title compound (76% yield). $^1$H NMR (DMSO-$d_6$) δ 2.35 (s, 3H, CH$_3$), 6.39 (s, 1H, Ar), 7.40 (d, 1H, J=8.4 Hz, Ar), 7.47 (d, 2H, J=8.5 Hz, Ar), 7.70-7.71 (m, 2H, Ar), 7.84-7.89 (m, 2H, Ar), 10.95 (br s, 1H, NH).

Example 85

6-(5-Bromo-2-methyl-phenyl)-N*4*-(4-bromo-phenyl)-pyrimidine-2,4-diamine

Following the method described in Example 26, 4-(5-bromo-2-methyl-phenyl)-6-chloro-pyrimidin-2-ylamine and 4-bromo-phenylamine provided the title compound (91% yield). $^1$H NMR (DMSO-d$_6$) δ 2.34 (s, 3H, CH$_3$), 6.37 (s, 1H, Ar), 7.40 (d, 1H, J=8.9 Hz, Ar), 7.59 (d, 2H, J=8.7 Hz, Ar), 7.70-7.71 (m, 2H, Ar), 7.82-7.84 (m, 2H, Ar), 10.89 (br s, 1H, NH).

Example 86

4-[2-Amino-6-(5-bromo-2-methyl-phenyl)-pyrimidin-4-ylamino]-benzonitrile

Following the method described in Example 26, 4-(5-bromo-2-methyl-phenyl)-6-chloro-pyrimidin-2-ylamine and 4-amino-benzonitrile provided the title compound (72% yield). $^1$H NMR (CD$_3$OD) δ 2.40 (s, 3H, CH$_3$), 6.38 (s, 1H, Ar), 7.39 (d, 1H, J=8.9 Hz, Ar), 7.68-7.69 (m, 2H, Ar), 7.78-7.80 (m, 2H, Ar), 8.07 (d, 2H, J=7.6 Hz, Ar).

Example 87

6-(5-Bromo-2-methyl-phenyl)-N*4*-(4-oxazol-4-yl-phenyl)-pyrimidine-2,4-diamine

Following the method described in Example 26, 4-(5-bromo-2-methyl-phenyl)-6-chloro-pyrimidin-2-ylamine and 4-oxazol-4-yl-phenylamine provided the title compound (61% yield). $^1$H NMR (CD$_3$OD) δ 2.41 (s, 3H, CH$_3$), 6.37 (s, 1H, Ar), 7.38 (d, 1H, J=7.8 Hz, Ar), 7.61 (s, 1H, Ar), 7.66-7.69 (m, 2H, Ar), 7.81 (d, 2H, J=8.7 Hz, Ar), 7.99 (d, 2H, J=8.5 Hz, Ar), 8.43 (br s, 1H, NH).

Example 88

6-(5-Bromo-2-methyl-phenyl)-N*4*-(4-nitro-phenyl)-pyrimidine-2,4-diamine

Following the method described in Example 26, 4-(5-bromo-2-methyl-phenyl)-6-chloro-pyrimidin-2-ylamine and 4-nitro-phenylamine provided the title compound (74% yield). $^1$H NMR (CD$_3$OD) δ 2.41 (s, 3H, CH$_3$), 6.42 (s, 1H, Ar), 7.39 (d, 1H, J=8.0 Hz, Ar), 7.67-7.70 (m, 2H, Ar), 8.14 (d, 2H, J=9.0 Hz, Ar), 8.31-8.34 (m, 2H, Ar).

Example 89

N*4*-(4-Chloro-phenyl)-6-[5-chloro-2-(2,2,2-trifluoro-ethoxy)-phenyl]-pyrimidine-2,4-diamine A mixture of 2-bromo-4-chloro-phenol (2.0 g, 9.6 mmol), trifluoro-methanesulfonic acid 2,2,2-trifluoro-ethyl ester (3.8 g, 16.4 mmol), potassium carbonate (8.0 g, 59 mmol), and N,N-dimethylformaldehyde (80 ml) was heated to 100° C. for 72 hours. After cooling to room temperature, the mixture was concentrated under reduced pressure. The residue was treated with water (150 ml) and extracted with ethyl acetate (160 ml). The organic extract was dried over magnesium sulfate and concentrated under reduced pressure. The residue was purified by flash chromatography on silica gel eluting with ethyl acetate-hexane (1:4) to give 2-bromo-4-chloro-1-(2,2,2-trifluoro-ethoxy)-benzene (3.0 g, 100% yield). $^1$H NMR (acetone-d$_6$) δ 4.80 (q, 2H, J=8.4 Hz, CH$_2$), 7.28 (d, 1H, J=8.9 Hz, Ar), 7.45 (dd, 1H, J=8.9 Hz, J=2.5 Hz, Ar), 7.69 (d, 1H, J—2.5 Hz, Ar).

To a mixture of 2-bromo-4-chloro-1-(2,2,2-trifluoro-ethoxy)-benzene (3.0 g, 10.4 mmol) and tetrahydrofuran (60 ml), cooled to −70° C., was added a solution of isopropyl-magnesium chloride in tetrahydrofuran (2 M, 5.7 ml). After warming to 0° C., the mixture was stirred for 1 hour. After cooling to −70° C., the mixture was treated with trimethylborate (1.2 g, 11.4 mmol). After stirring at room temperature for 12 hours, the mixture was treated with hydrochloric acid (2 M, 20 ml). After stirring for 40 minutes, the mixture was extracted with ethyl acetate (2×50 ml). The combined extracts were dried over magnesium sulfate and concentrated under reduced pressure. The residue was triturated with hexane (50 ml). Filtration and drying of the solid under reduced pressure gave 5-chloro-2-(2,2,2-trifluoro-ethoxy)-phenylboronic acid (1.6 g, 61% yield). $^1$H NMR (acetone-d$_6$) δ 4.86 (q, 2H, J=8.5 Hz, CH$_2$), 7.12 (d, 2H, J=4.6 Hz, OH), 7.20 (d, 1H, J=8.8 Hz, Ar), 7.49 (dd, 1H, J=8.8 Hz, J=2.8 Hz, Ar), 7.76 (d, 1H, J—2.7 Hz, Ar).

To a mixture of 5-chloro-2-(2,2,2-trifluoro-ethoxy)-phenylboronic acid (1.6 g, 6.3 mmol), 4,6-dichloro-pyrimidin-2-ylamine (1.2 g, 7.6 mmol), palladium acetate (211 mg, 0.95 mmol), and dimethyl ethylene glycol (100 ml), degassed with argon, was added a solution of sodium carbonate (4.0 g, 37.8 mmol) in water (15 ml) followed by triphenylphosphine (495 mg, 1.9 mmol). After stirring for 12 hours, the mixture was filtered through a pad of celite under suction. The organic layer was separated from the filtrate and dried over magnesium sulfate. The mixture was purified by flash chromatography on silica gel eluting with ethyl acetate-hexane (1:5 followed by 1:4) to give 4-chloro-6-[5-chloro-2-(2,2,2-trifluoro-ethoxy)-phenyl]-pyrimidin-2-ylamine, which was dissolved in ethyl acetate (10 ml) and treated with a solution of hydrogen chloride in dioxane (4 M, 2.5 ml). The solid was filtered to provide the hydrochloride salt of 4-chloro-6-[5-chloro-2-(2,2,2-trifluoro-ethoxy)-phenyl]-pyrimidin-2-ylamine (500 mg, 20% yield). $^1$H NMR (CD$_3$OD) δ 4.78 (q, 2H, J=8.5 Hz, CH$_2$), 7.31-7.33 (m, 2H, Ar), 7.65 (dd, 1H, J=8.9 Hz, J=2.8 Hz, Ar), 7.82 (d, 1H, J=2.6 Hz, Ar).

Following the method described in Example 26, the hydrochloride salt of 4-chloro-6-[5-chloro-2-(2,2,2-trifluoro-ethoxy)-phenyl]-pyrimidin-2-ylamine and 4-chloro-phenylamine provided the title compound (76% yield). $^1$H NMR (acetone-d$_6$) δ 4.76 (q, 2H, J=8.5 Hz, CH$_2$), 6.72 (s, 1H, Ar), 7.26-7.31 (m, 3H, Ar), 7.44 (dd, 1H, J=8.8 Hz, J=2.8 Hz, Ar), 7.80-7.83 (m, 2H, Ar), 7.94 (d, 1H, J=2.8 Hz, Ar).

Example 90

2-{4-[2-Amino-6-(5-chloro-2-ethoxy-phenyl)-pyrimidin-4-ylamino]-phenoxy}-ethanol A mixture of 2-(4-nitro-phenoxy)-ethanol (1.0 g, 5.5 mmol), 10% palladium on carbon (110 mg), methanol (40 ml), and ethyl acetate (20 ml) was treated with hydrogen gas (50 psi) on a Parr shaker for 1 hour. The mixture was filtered through a pad of celite under suction and the filtrate was concentrated under reduced pressure to give 2-(4-amino-phenoxy)-ethanol (820 mg, 99% yield). $^1$H NMR (DMSO-d$_6$) δ 3.61-3.64 (m, 2H, CH$_2$), 3.80 (t, 2H, J=5.0 Hz CH$_2$), 4.57 (br s, 2H, NH$_2$), 4.74 (t, 1H, J=5.6 Hz, OH), 6.47 (d, 2H, J=8.7 Hz, Ar), 6.62 (d, 2H, J=8.8 Hz, Ar).

Following the method described in Example 26, 4-chloro-6-(5-chloro-2-ethoxy)-phenyl)-pyrimidin-2-ylamine and 2-(4-amino-phenoxy)-ethanol provided the title compound (61% yield). $^1$H NMR (DMSO-d$_6$) δ 1.31 (t, 3H, J=6.9 Hz CH$_3$), 3.67-3.71 (m, 2H, CH$_2$), 3.93 (t, 2H, J=4.9 Hz CH$_2$), 4.07 (q, 2H, J=6.9 Hz CH$_2$), 4.83 (t, 1H, J=5.6 Hz OH), 6.16 (s, 2H, NH$_2$), 6.86 (d, 2H, J=8.9 Hz, Ar), 7.09 (d, 1H, J=8.9 Hz, Ar), 7.36 (dd, 1H, J=8.8 Hz, J=2.8 Hz, Ar), 7.50 (d, 2H, J=8.5 Hz, Ar), 7.90 (d, 1H, J=2.8 Hz, Ar), 8.90 (s, 1H, NH).

Example 91

N*4*-(4-Bromo-phenyl)-6-[5-bromo-2-(2,2,2-trifluoro-ethoxy)-phenyl]-pyrimidine-2,4-diamine Following the method described in Example 89 for the synthesis of 2-bromo-4-chloro-1-(2,2,2-trifluoro-ethoxy)-benzene 4-bromo-phenol and trifluoro-methanesulfonic acid 2,2,2-trifluoro-ethyl ester gave 1-bromo-4-(2,2,2-trifluoro-ethoxy)-benzene (40% yield). $^1$H NMR (acetone-d$_6$) δ 4.68 (q, 2H, J=8.5 Hz, CH$_2$), 7.04 (d, 2H, J=9.1 Hz, Ar), 7.49 (d, 2H, J=9.1 Hz, Ar).

Following the method described in Example 81 for the synthesis of 4-(5-bromo-2-methyl-phenyl)-6-chloro-pyrimidin-2-ylamine 1-bromo-4-(2,2,2-trifluoro-ethoxy)-benzene gave 4-[5-bromo-2-(2,2,2-trifluoro-ethoxy)-phenyl]-6-chloro-pyrimidin-2-ylamine (39% yield for 3 steps).

Following the method described in Example 26, 4-[5-bromo-2-(2,2,2-trifluoro-ethoxy)-phenyl]-6-chloro-pyrimidin-2-ylamine and 4-bromo-phenylamine provided the title compound (34% yield). $^1$H NMR (acetone-d$_6$) δ 4.76 (q, 2H, J=8.5 Hz, CH$_2$), 5.95 (bs, 2H, NH$_2$), 6.72 (s, 1H, Ar), 7.21 (d, 1H, J=8.8 Hz, Ar), 7.44 (d, 2H, J=8.9 Hz, Ar), 7.58 (dd, 1H, J=8.8 Hz, J=2.4 Hz, Ar), 7.75-7.78 (m, 2H, Ar), 8.07 (d, 1H, J=2.4 Hz, Ar), 8.62 (br s, 1H, NH).

Example 92

3-{4-[2-Amino-6-(5-chloro-2-ethoxy-phenyl)-pyrimidin4-ylamino]-phenyl}-propan-1-ol To a mixture of 3-(4-amino-phenyl)-propionic acid (1.85 g, 11.2 mmol) and tetrahydrofuran'(200 ml), was added lithium aluminum hydride (1.0 g, 26 mmol). After stirring for 3 hours, the mixture was quenched by addition of methanol (5 ml) and concentrated under reduced pressure. The residue was treated with saturated aqueous sodium chloride solution (100 ml) and extracted with ethyl acetate (200 ml). The organic extract was concentrated under reduced pressure to give 3-(4-amino-phenyl)-propan-1-ol (1.5 g, 89% yield).

Following the method described in Example 4,4-chloro-6-(5-chloro-2-ethoxy-phenyl)-pyrimidin-2-yl-amine and 3-(4-amino-phenyl)-propan-1-ol provided the title compound (26% yield). $^1$H NMR (DMSO-d$_6$) δ 1.34 (t, 3H, J=6.9 Hz, CH$_3$), 1.69 (m, 2H, CH$_2$), 2.55 (t, 2H, J=7.5 Hz, CH$_2$), 3.40 (q, 2H, J=6.4 Hz, CH$_2$), 4.10 (q, 2H, J=7.0 Hz, CH$_2$), 4.45 (t, 1H, J=5.1 Hz, OH), 6.21 (s, 2H, NH$_2$), 6.76 (s, 1H, Ar), 7.09-7.13 (m, 3H, Ar), 7.37-7.39 (m, 1H), 7.55 (d, 2H, J=8.2 Hz, Ar), 7.92 (m, 1H, Ar), 9.04 (s, 1H, NH).

Example 93

4-{4-[2-Amino-6-(5-chloro-2-ethoxy-phenyl)-pyrimidin4-ylamino]-phenyl}-butan-1-ol A mixture of 4-(4-nitro-phenyl)-butan-1-ol (2.0 g, 1.02 mmol), palladium on carbon (100 mg, 10%) and ethanol (25 ml) was treated with hydrogen gas on a Parr shaker (50 psi) for 1 hour. The mixture was filtered through a pad of celite under suction and the filtrate was concentrated under reduced pressure to afford 4-(4-amino-phenyl)-butan-1-ol (100% yield).

Following the method described in Example 4,4-chloro-6-(5-chloro-2-ethoxy-phenyl)-pyrimidin-2-yl-amine and 4-(4-amino-phenyl)-butan-1-ol provided the title compound (58% yield). $^1$H NMR (DMSO-d$_6$) δ 1.36 (t, 3H, J=6.9 Hz, CH$_3$), 1.42 (m, 2H, CH$_2$), 1.55 (m, 2H, CH$_2$), 2.54 (m, 2H, CH$_2$), 3.41 (q, 2H, J=5.3 Hz, CH$_2$), 4.11 (q, 2H, J=7.0 Hz, CH$_2$), 4.37 (t, 1H, OH), 6.23 (s, 2H, NH$_2$), 6.77 (s, 1H, Ar), 7.10-7.14 (m, 3H, Ar), 7.35-7.40 (m, 1H), 7.55 (d, 2H, Ar), 7.94 (m, 1H, Ar), 9.04 (s, 1H, NH).

Example 94

6-(5-Chloro-2-ethoxy-phenyl)-N*4*-(4-fluoro-phenyl)-pyrimidine-2,4-diamine

Following the method described in Example 4,4-chloro-6-(5-chloro-2-ethoxy-phenyl)-pyrimidin-2-yl-amine and 4-fluoro-phenylamine provided the title compound (68% yield). $^1$H NMR (DMSO-d$_6$) δ 1.35 (t, 3H, J=6.9 Hz, CH$_3$), 4.11 (q, 2H, J=7.0 Hz, CH$_2$), 6.27 (s, 2H, NH$_2$), 6.73 (s, 1H, Ar), 7.09-7.13 (m, 3H, Ar), 7.38-7.40 (m, 1H), 7.69-7.73 (m, 2H, Ar), 7.92 (m, 1H, Ar), 9.15 (s, 1H, NH).

Example 95

4-{4-[2-Amino-6-(5-chloro-2-ethoxy-phenyl)-pyrimidin4-ylamino]-phenyl}-butyric acid Following the method described in Example 4,4-chloro-6-(5-chloro-2-ethoxy-phenyl)-pyrimidin-2-yl-amine and 4-(4-amino-phenyl)-butyric acid provided 4-{4-[2-amino-6-(5-chloro-2-ethoxy-phenyl)-pyrimidin-4-ylamino]-phenyl}-butyric acid ethyl ester hydrochloride salt (90% yield).

A mixture of 4-{4-[2-amino-6-(5-chloro-2-ethoxy-phenyl)-pyrimidin-4-ylamino]-phenyl}-butyric acid ethyl ester (350 mg, 0.71 mmol), sodium hydroxide (150 mg, 3.8 mmol) and ethanol (5 ml) was stirred for 18 hours. Ethyl acetate (100 ml), saturated aqueous sodium chloride solution (100 ml) and concentrated hydrochloric acid (1 ml) were added and the mixture was stirred for 10 minutes. The organic layer was concentrated under reduced pressure. The residual solid was treated with water (25 ml) and stirred vigorously. Suction filtration afforded the title compound (200 mg 61% yield) as a white powder. $^1$H NMR (DMSO-d$_6$) δ 1.38 (m, 3H, CH$_3$), 1.83 (m, 2H, CH$_2$), 2.23 (m, 2H, CH$_2$), 2.61 (m, 2H, CH$_2$), 4.17 (m, 2H, CH$_2$), 6.60 (s, 1H, Ar), 7.20-7.29 (m, 3H, Ar), 7.61-7.71 (m, 4H, Ar), 10.76 (s, 1H, NH), 12.48 (s, 1H).

Example 96

4-[2-Amino-6-(5-chloro-2-ethoxy-phenyl)-pyrimidin-4-ylamino]-benzenesulfonamide

Following the method described in Example 4,4-chloro-6-(5-chloro-2-ethoxy-phenyl)-pyrimidin-2-yl-amine and 4-amino-benzenesulfonamide provided the title compound (43% yield). $^1$H NMR (DMSO-d$_6$) δ 1.40 (t, 3H, J=7.0 Hz, CH$_3$), 4.15 (q, 2H, J=7.0 Hz, CH$_2$), 6.45 (s, 2H, NH$_2$), 6.82 (s, 1H, Ar), 7.14-7.16 (m, 1H, Ar), 7.20 (s, 2H, NH$_2$), 7.40-7.41 (m, 1H, Ar), 7.71 (d, 2H, J=8.8 Hz, Ar), 7.93 (m, 2H, Ar), 9.56 (s, 1H, NH).

Example 97

6-(5-Chloro-2-methyl-phenyl)-N*4*-(4-fluoro-phenyl)-pyrimidine-2,4-diamine

Following the method described in Example 4,4-chloro-6-(5-chloro-2-methyl-phenyl)-pyrimidin-2-yl-amine and 4-fluoro-phenylamine provided the title compound (66% yield). $^1$H NMR (DMSO-d$_6$) δ 6.06 (s, 1H, Ar), 6.37 (s, 2H, NH$_2$), 7.11 (t, 2H, J=8.8 Hz, Ar), 7.29-7.40 (m, 3H, Ar), 7.74-7.77 (m, 2H, Ar), 9.22 (s, 1H, NH).

Example 98

N*4*-(4-Chloro-phenyl)-6-(2,3,5-trichloro-phenyl)-pyrimidine-2,4-diamine

Following the method described in Example 4,4-chloro-6-(2,3,5-trichloro-phenyl)-pyrimidin-2-yl-amine and 4-chloro-phenylamine provided the title compound (42% yield). $^1$H NMR (DMSO-d$_6$) δ 6.22 (s, 1H, Ar), 6.55 (s, 2H, NH$_2$), 7.32 (d, 2H, J=8.8 Hz, Ar), 7.58 (m, 1H, Ar), 7.80 (d, 2H, J=8.8 Hz, Ar), 7.93 (m, 1H, Ar), 9.47 (s, 1H, NH).

Example 99

N*4*-(4-Bromo-phenyl)-6-(2,3,5-trichloro-phenyl)-pyrimidine-2,4-diamine

Following the method described in Example 4,4-chloro-6-(2,3,5-trichloro-phenyl)-pyrimidin-2-yl-amine and 4-bromo-phenylamine provided the title compound (45% yield). $^1$H NMR (DMSO-d$_6$) δ 6.23 (s, 1H, Ar), 6.57 (s, 2H, NH$_2$), 7.45 (d, 2H, J=8.8 Hz, Ar), 7.59 (m, 1H, Ar), 7.76 (d, 2H, J=8.8 Hz, Ar), 7.93 (m, 1H, Ar), 9.47 (s, 1H, NH).

Example 100

2-{4-[2-Amino-6-(5-bromo-2-methyl-phenyl)-pyrimidin-4-ylamino]-phenyl}-ethanol

Following the method described in Example 4,4-chloro-6-(5-bromo-2-methyl-phenyl)-pyrimidin-2-yl-amine and 2-(4-amino-phenyl)-ethanol provided the title compound (12% yield). $^1$H NMR (DMSO-d$_6$) δ 2.32 (s, 3H, CH$_3$), 2.67 (t, 2H, J=7.1 Hz, CH$_2$), 3.57 (m, 2H, CH$_2$), 4.61 (m, 1H, OH), 6.06 (s, 1H, Ar), 6.32 (s, 2H, NH$_2$), 7.12 (d, 2H, J=8.4 Hz, Ar), 7.23 (d, 1H, J=8.1 Hz, Ar), 7.47-7.49 (m, 1H, Ar), 7.52 (m, 1H, Ar), 7.60 (d, 2H, J=8.3 Hz, Ar), 9.10 (s, 1H, NH).

Example 101

4-{4-[2-Amino-6-(5-bromo-2-methyl-phenyl)-pyrimidin4-ylamino]-phenyl}-butan-1-ol Following the method described in Example 4,4-chloro-6-(5-bromo-2-methyl-phenyl)-pyrimidin-2-yl-amine and 4-(4-amino-phenyl)-butan-1-ol provided the title compound (16% yield). $^1$H NMR (DMSO-d$_6$) δ 1.44 (m, 2H, CH$_2$), 1.57 (m, 2H, CH$_2$), 2.33 (m, 3H, CH$_3$), 2.53 (t, 2H, J=7.4 Hz, CH$_2$), 3.40 (m, 2H, CH$_2$), 4.37 (t, 1H, OH), 6.07 (s, 1H, Ar), 6.33 (s, 2H, NH$_2$), 7.11 (d, 2H, J=8.3 Hz, Ar), 7.24 (d, 1H, J=8.2 Hz, Ar), 7.48 (m, 1H, Ar), 7.53 (m, 1H, Ar), 7.61 (d, 2H, J=8.2 Hz, Ar), 9.11 (s, 1H, NH).

Example 102

6-(2,3,5-trichloro-phenyl) N*4*-(4-trifluoromethyl-phenyl)-pyrimidine-2,4-diamine Following the method described in Example 4,4-chloro-6-(2,3,5-trichloro-phenyl)-pyrimidin-2-yl-amine and 4-trifluoromethyl-phenylamine provided the title compound (45% yield). $^1$H NMR (DMSO-d$_6$) δ 6.30 (s, 1H, Ar), 6.66 (s, 2H, NH$_2$), 7.61-7.63 (m, 3H, Ar), 7.95 (m, 1H, Ar), 8.00 (d, 2H, J=8.5 Hz, Ar), 9.75 (s, 1H, NH).

Example 103

1-{4-[2-Amino-6-(5-chloro-2-methyl-phenyl)-pyrimidin4-ylamino]-phenyl}-2,2,2-trifluoro-ethanol To a mixture of 4-nitro-benzoic acid methyl ester (1.8 g, 9.9 mmol), trimethyl-trifluoromethyl-silane (2.0 ml, 12.8 mmol) and anhydrous dichloromethane (20 ml), cooled at −78° C., was added a solution of tetrabutylammonium fluoride in dichloromethane (1 M, 0.5 ml) previously dried over 4A molecular sieves. After stirring for 72 hours, hydrochloric acid (1 M, 50 ml) was added. The mixture was treated with saturated aqueous sodium chloride solution (100 ml) and extracted with ethyl acetate (100 ml). The organic extract was concentrated under reduced pressure. The residue was purified by flash chromatography on silica gel eluting with ethyl acetate-hexane (1:3) providing 2,2,2-trifluoro-1-(4-nitro-phenyl)-ethane-1,1-diol (1.1 g, 47% yield).

A mixture of 2,2,2-trifluoro-1-(4-nitro-phenyl)-ethane-1, 1-diol (1.1 g, 4.6 mmol), palladium on carbon (100 mg, 10%), and ethanol (50 ml) was treated with hydrogen gas on a Parr shaker (50 psi) for 1 hour. The mixture was filtered through celite under suction and the filtrate was concentrated under reduced pressure to afford 1-(4-amino-phenyl)-2,2,2-trifluoro-ethanol (100% yield).

Following the method described in Example 4,4-chloro-6-(5-chloro-2-methyl-phenyl)-pyrimidin-2-yl-amine and 1-(4-amino-phenyl)-2,2,2-trifluoro-ethanol provided the title compound (66% yield). $^1$H NMR (DMSO-d$_6$) δ 2.34 (s, 3H, CH$_3$), 5.08 (m, 1H, CH), 6.11 (s, 1H, Ar), 6.40 (s, 2H, NH$_2$), 6.70 (d, 1H, J=5.5 Hz, OH), 7.29-7.40 (m, 5H, Ar), 7.78 (d, 2H, J=8.5 Hz, Ar), 9.29 (s, 1H, NH).

Example 104

1-{4-[2-Amino-6-(5-chloro-2-methyl-phenyl)-pyrimidin-4-ylamino]-phenyl}-ethanone-oxime To a mixture of 1-(4-amino-phenyl)-ethanone (2.75 g, 20.3 mmol) and hydroxylamine hydrochloride salt (2.1 g, 30.5 mmol) in ethanol (200 ml) was added sodium hydroxide (4.1 g, 101.7 mmol) in water (50 ml). After stirring for 18 hours, the mixture was treated with saturated aqueous sodium chloride solution (100 ml) and extracted with dichloromethane (200 ml). The organic extract was concentrated under reduced pressure to afford 1-(4-amino-phenyl)-ethanone-oxime (30% yield).

Following the method described in Example 4,4-chloro-6-(5-chloro-2-methyl-phenyl)-pyrimidin-2-yl-amine and 1-(4-amino-phenyl)-ethanone-oxime provided the title compound (19% yield). ¹H NMR (DMSO-d₆) δ 2.14 (s, 3H, CH₃), 2.36 (s, 3H, CH₃), 6.13 (s, 1H, Ar), 6.42 (s, 2H, NH₂), 7.33-7.42 (m, 3H, Ar), 7.58 (d, 2H, J=8.6 Hz, Ar), 7.79 (d, 2H, J=8.7 Hz, Ar), 9.34 (s, 1H, NH), 11.00 (s, 1H, OH).

Example 105

N*4*-(4-Chloro-phenyl)-6-(2-trifluoromethyl-phenyl)-pyrimidine-2,4-diamine

Following the method described in Example 53, 2-trifluoromethyl-phenyl boronic acid was converted to 4-chloro-6-(2-trifluoromethyl-phenyl)-pyrimidin-2-ylamine (36% yield).

Following the method described in Example 53, 4-chloro-6-(2-trifluoromethyl-phenyl)-pyrimidin-2-ylamine and 4-chloro-phenylamine provided the title compound (28% yield). ¹H NMR (DMSO-d₆) δ 6.06 (s, 1H, Ar), 6.45 (s, 2H, NH₂), 7.32 (d, 2H, J=8.9 Hz, Ar), 7.49 (d, 1H, J=9.0 Hz, Ar), 7.62-7.75 (m, 2H, Ar), 7.81 (d, 3H, J=8.9 Hz, Ar), 9.37 (s, 1H, NH).

Example 106

N*4*-(4-Chloro-phenyl)-6-phenyl-pyrimidine-2,4-diamine

Following the method described in Example 53, phenyl boronic acid was converted to 4-chloro-6-phenyl-pyrimidin-2-ylamine (25% yield).

Following the method described in Example 53, 4-chloro-6-phenyl-pyrimidin-2-ylamine and 4-chloro-phenylamine provided the title compound as the hydrochloride salt (63% yield). ¹H NMR (DMSO-d₆) δ 6.70 (s, 1H, Ar), 7.47 (d, 2H, J=8.7 Hz, Ar), 7.66 (d, 3H, J=6.9 Hz, Ar), 7.88 (d, 4H, J=7.2 Hz, Ar), 9.42 (s, 1H, NH), 12.91 (s, 1H, NH).

Example 107

6-(3-Chloro-phenyl)-N*4*-(4-trifuoromethyl-phenyl)-pyrimidine-2,4-diamine

Following the method described in Example 53, 3-chloro-phenyl boronic acid was converted to 4-chloro-6-(3-chloro-phenyl)-pyrimidin-2-ylamine (60% yield).

Following the method described in Example 53, 4-chloro-6-(3-chloro-phenyl)-pyrimidin-2-ylamine and 4-trifluoromethyl-aniline provided the title compound as the hydrochloride salt (61% yield). ¹H NMR (DMSO-d₆) δ 6.57 (s, 1H, Ar), 7.58 (m, 4H, Ar), 7.72 (s, 1H, Ar), 7.84 (s, 1H, Ar), 8.01 (s, 2H, Ar), 10.75 (s, 1H, NH), 12.87 (s, 2H, NH₂).

Example 108

6-(5-Chloro-2-methyl-phenyl)-N*4*-(4-nitro-phenyl)-pyrimidine-2,4-diamine

Following the method described in Example 4, 4-chloro-6-(5-chloro-2-methyl-phenyl)-pyrimidin-2-yl-amine and 4-nitroaniline provided the title compound as the hydrochloride salt (64% yield). ¹H NMR (DMSO-d₆) δ 2.26 (s, 3H, CH₃), 6.38 (s, 1H, Ar), 7.30-7.49 (m, 3H, Ar), 8.06-8.17 (m, 4H, Ar), 11.17 (s, 1H, NH), 12.97 (s, 1H, NH₂).

Example 109

3-{4-[2-Amino-6-(5-Chloro-2-methyl-phenyl)-pyrimidin-4-ylamino]-phenyl}-propan-1-ol Following the method described in Example 4, 4-chloro-6-(5-chloro-2-methyl-phenyl)-pyrimidin-2-yl-amine and 4-amino-phenyl-propan-1-ol provided the title compound as the hydrochloride salt (67% yield). ¹H NMR (DMSO-d₆) δ 1.72 (t, 2H, J=7.4 Hz, CH₂), 2.37 (s, 3H, CH₃), 2.62 (t, 2H, J=7.8 Hz, CH₂), 3.41 (t, 2H, J=6.9 Hz, CH₂), 6.35 (s, 1H, Ar), 7.24 (d, 2H, J=8.3 Hz, Ar), 7.46 (d, 1H, J=8.0 Hz, Ar), 7.57-7.60 (m, 2H, Ar), 7.71 (d, 2H, J=7.8 Hz, Ar), 10.75 (s, 1H, NH), 12.70 (s, 1H, OH).

Example 110

4-{4-[2-Amino-6-(5-Chloro-2-methyl-phenyl)-pyrimidin-4-ylamino]-phenyl}-butan-1-ol Following the method described in Example 4, 4-chloro-6-(5-chloro-2-methyl-phenyl)-pyrimidin-2-yl-amine and 4-amino-phenyl-butan-1-ol provided the title compound as the hydrochloride salt (81% yield). ¹H NMR (DMSO-d₆) δ 1.41-1.48 (m, 2H, CH₂), 1.57-1.64 (m, 2H, CH₂), 2.38 (s, 3H, CH₃), 2.59 (t, 2H, J=7.4 Hz, CH₂), 3.41 (t, 2H, J=6.5 Hz, CH₂), 6.38 (s, 1H, Ar), 7.23 (d, 2H, J=8.3 Hz, Ar), 7.46 (d, 1H, J=8.1 Hz, Ar), 7.54-7.60 (m, 2H, Ar), 7.72 (d, 2H, J=7.7 Hz, Ar), 10.81 (s, 1H, NH), 12.73 (s, 1H, OH).

Example 111

6-(5-Chloro-2-methyl-phenyl)-N*4*-(3-methylsulfanyl-phenyl)-pyrimidine-2,4-diamine Following the method described in Example 4, 4-chloro-6-(5-chloro-2-methyl-phenyl)-pyrimidin-2-yl-amine and 3-methylsulfanyl-phenylamine provided the title compound (58% yield). ¹H NMR (DMSO-d₆) δ 2.36 (s, 3H, CH₃), 2.50 (s, 3H, CH₃), 6.11 (s, 1H, Ar), 6.40 (s, 2H, NH₂), 6.85 (d, 1H, J=7.8 Hz, Ar), 7.22 (t, 1H, J=7.9 Hz, Ar), 7.31 (d, 1H, J=8.2 Hz, Ar), 7.36-7.42 (m, 2H, Ar) 7.55 (d, 1H, J=8.0 Hz, Ar), 7.65 (s, 1H, Ar), 9.23 (s, 1H, NH).

Example 112

6-(3,5-Dichloro-phenyl)-N*4*-(4-trifuoromethyl-phenyl)-pyrimidine-2,4-diamine

Following the method described in Example 53, 3,5-dichloro-phenyl boronic acid was converted to 4-chloro-6-(3,5-dichloro-phenyl)-pyrimidin-2-ylamine (45% yield).

Following the method described in Example 53, 4-chloro-6-(3,5-dichloro-phenyl)-pyrimidin-2-ylamine and 4-trifluoromethyl-aniline provided the title compound as the hydrochloride salt (51% yield). ¹H NMR (DMSO-d₆) δ 2.37 (s, 3H, CH₃), 6.45 (s, 1H, Ar), 7.46 (d, 1H, J=8.1 Hz, Ar), 7.59 (d, 2H, J=8.1 Hz, Ar), 7.95-7.98 (m, 4H, Ar), 11.04 (s, 1H, NH), 12.90 (s, 2H, NH₂).

Example 113

{5-[2-Amino-6-(5-chloro-2-methyl-phenyl)-pyrimidin-4-ylamino]-2-chloro-phenyl}-methanol Following the method described in Example 4, 4-chloro-6-(5-chloro-2-methyl-phenyl)-pyrimidin-2-yl-amine and (5-amino-2-chloro-phenyl)-methanol provided the title compound (59% yield). $^1$H NMR (DMSO-d$_6$) δ 2.35 (s, 3H, CH$_3$), 4.55 (d, 2H, J=4.3 Hz, CH$_2$), 5.40 (s, 1H, OH), 6.13 (s, 1H, Ar), 6.40 (s, 2H, NH$_2$), 7.27 (d, 1H, J=8.7 Hz, Ar), 7.31 (d, 1H, J=8.2 Hz, Ar), 7.36-7.41 (m, 2H, Ar), 7.67 (d, 1H, J=1.9 Hz, Ar), 8.00-8.03 (dd, 1H, J=2.1 Hz, J=8.6 Hz, Ar), 9.38 (s, 1H, NH).

Example 114

3-[2-Amino-6-(5-chloro-2-methyl-phenyl)-pyrimidin4-ylamino]-benzoic acid ethyl ester Following the method described in Example 4,4-chloro-6-(5-chloro-2-methyl-phenyl)-pyrimidin-2-yl-amine and 3-amino-benzoic acid ethyl ester provided the title compound as the hydrochloride salt (34% yield). $^1$H NMR (DMSO-d$_6$) δ 1.44 (t, 3H, J=9.8 Hz, CH$_3$), 2.40 (s, 3H, CH$_3$), 4.41-4.46 (m, 2H, CH$_2$), 6.33 (s, 1H, Ar), 7.44-7.49 (m, 2H, Ar), 7.53-7.58 (m, 3H, Ar), 7.89 (d, 1H, J=7.5 Hz, Ar), 8.13 (d, 1H, J=7.5 Hz, Ar), 8.43 (s, 1H, NH).

Example 115

6-(5-Chloro-2-methyl-phenyl)-N*4*-(3-ethyl-phenyl)-pyrimidine-2,4-diamine

Following the method described in Example 4,4-chloro-6-(5-chloro-2-methyl-phenyl)-pyrimidin-2-yl-amine and 3-ethyl-phenylamine provided the title compound (91% yield). $^1$H NMR (DMSO-d$_6$) δ 1.29 (t, 3H, J=7.6 Hz, CH$_3$), 2.38 (s, 3H, CH$_3$), 2.69-2.74 (m, 2H, CH$_2$), 6.30 (s, 1H, Ar), 7.09 (d, 1H, J=7.4 Hz, Ar), 7.32-7.36 (m, 1H, Ar), 7.31 (d, 1H, J=Hz, Ar), 7.36-7.42 (m, 2H, Ar) 7.55 (d, 1H, Ar), 7.65 (s, 1H, Ar), 9.23 (s, 1H, NH).

Example 116

2-{4-[2-Amino-6-(5-chloro-2-methyl-phenyl)-pyrimidin-2-yl-amino]-phenyl}-propane-1,3-diol To a solution of diethyl malonate (320 mg, 2 mmol) in tetrahydrofuran (15 ml) was added a solution of potassium tert-butoxide in tetrahydrofuran (1 M, 2.2 ml, 2.2 mmol). After stirring for 10 minutes, 4-bromonitrobenzene (404 mg, 2 mmol) was added. After stirring for 12 hours, the reaction was quenched by addition of saturated aqueous ammonium chloride solution (50 ml) and extracted with ethyl acetate (2×50 ml). The combined extracts were dried over anhydrous magnesium sulfate and concentrated under reduced pressure to provide crude 2-(4-nitro-phenyl)-malonic acid diethyl ester.

A mixture of crude 2-(4-nitro-phenyl)-malonic acid diethyl ester and 10% palladium on carbon in ethyl acetate (20 ml) was treated with hydrogen gas (40 psi) on a Parr shaker for 2 hours. The mixture was filtered and the filtrate was concentrated under reduced pressure. The residue was purified by flash chromatography on silica gel eluting with 25% ethyl acetate-hexane to provide 2-(4-amino-phenyl)-malonic acid diethyl ester (450 mg, 90% yield for 2 steps).

To a solution of 2-(4-amino-phenyl)-malonic acid diethyl ester (450 mg, 1.8 mmol) in anhydrous ether (20 ml), cooled at 0-10° C., was added lithium aluminum hydride (68 mg, 1.8 mmol). After stirring at room temperature for 2 hours, the reaction was cooled to 10° C. and quenched by the addition of hydrated sodium sulfate (2 g). The mixture was filtered and the solid was rinsed with tetrahydrofuran (10 ml). The combined filtrates were concentrated under reduced pressure. The residue was purified by flash chromatography on silica gel eluting with 20% methanol-chloroform to provide 2-(4-amino-phenyl)-propane-1,3-diol (52 mg, 17% yield).

To a solution of 4-chloro-6-(5-chloro-2-methyl-phenyl)-pyrimidin-2-yl-amine (78.6 mg, 0.31 mmol) (prepared in example 26) and 2-(4-amino-phenyl)-propane-1,3-diol (52 mg, 0.31 mmol) in ethanol (5 ml) was added a solution of hydrogen chloride in dioxane (4 M, 0.1 ml). After heating under reflux for 2 hours, the mixture was concentrated under reduced pressure. The residue was purified by flash chromatography on silica gel eluting with 20% methanol-chloroform to give 2-{4-{4-amino-6-(5-chloro-2-methyl-phenyl)-{1,3,5} triazin-2-yl-amino]-phenyl}-propane-1,3-diol (20 mg, 17% yield). $^1$H NMR (DMSO-d$_6$) δ 2.34 (s, 3H, CH$_3$), 2.6-2.8 (m, 1H, CH), 3.55-3.85 (m, 4H, CH$_2$O), 4.5-4.52 (t, 2H, —OH), 6.07 (s, 1H, Ar), 6.30 (s, 2H, NH$_2$), 7.13-7.15 (d, 2H, Ar), 7.29-7.40 (m, 3H, Ar), 7.57-7.59 (d, 2H, Ar), 9.10 (s, 1H, NH).

Example 117

6-(5-Chloro-2-ethoxy-phenyl)-N*4*-(2-chloro-phenyl)-pyrimidine-2,4-diamine

Following the method described in Example 53, 4-chloro-6-(5-chloro-2-ethoxy-phenyl)-pyrimidin-2-ylamine and 2-chloroaniline provided the title compound (31% yield). $^1$H NMR (DMSO-d$_6$) δ 1.19-1.22 (t, 3H, CH$_3$), 4.0-4.1 (q, 2H, CH$_2$), 6.0-6.30 (s, 2H, NH$_2$), 6.65 (s, 1H, Ar), 7.05-7.29 (m, 4H, Ar), 7.316 (d, 1H, Ar) 7.354 (d, 1H, Ar) 7.90 (d, 1H, Ar) 8.8 (br s, 1H, NH).

Example 118

6-(2,3-Dichloro-phenyl)-N*4*-(4-chloro-phenyl)-pyrimidine-2,4-diamine

4-Chloro-6-(2,3-dichloro-phenyl)-pyrimidin-2-ylamine was prepared according to the method described for 4-chloro-6-(5-chloro-2-ethoxy-phenyl)-pyrimidin-2-ylamine (Example 53) using 2,3-dichlorophenyl boronic acid and 2-amino-4,6-dichloropyrimidine.

Following the method described in Example 53, 4-chloro-6-(2,3-dichloro-phenyl)-pyrimidin-2-ylamine and 4-chloroaniline provided the title compound (42% yield). $^1$H NMR (CD$_3$OD) δ 6.19 (s, 1H, Ar), 7.29 (d, 2H, Ar), 7.31 (d, 2H, Ar) 7.4 (d, 1H, Ar) 7.55 (d, 2H, Ar).

Example 119

6-(3-Bromo-phenyl)-N*4*-(4-trifluoromethyl-phenyl)-pyrimidine-2,4-diamine

4-Chloro-6-(3-bromo-phenyl)-pyrimidin-2-ylamine was prepared according to the method described for 4-chloro-6-(5-chloro-2-ethoxy-phenyl)-pyrimidin-2-ylamine (Example 53) using 3-bromophenyl boronic acid and 2-amino-4,6-dichloropyrimidine.

Following the method described in Example 53, 4-chloro-6-(3-bromo-phenyl)-pyrimidin-2-ylamine and 4-trifluoromethylaniline provided the title compound (30% yield). $^1$H NMR (CD$_3$OD) δ 6.50 (s, 1H, Ar), 7.25-7.35 (t, 1H, Ar), 7.4-7.6 (m, 4H, Ar) 7.88 (d, 1H, Ar), 7.90 (d, 1H, Ar) 7.96 (d, 2H, Ar), 8.10 (s, 1H, Ar).

Example 120

1-{4-[2-amino-6-(5-chloro-2-ethoxyphenyl)pyrimidin-4-ylamino]phenyl}-2-methyl-propan-2-ol Following the procedure described in Example 4,4-chloro-6-(5-chloro-2-ethoxyphenyl)pyrimidin-2-yl-amine and ethyl 4-aminophenylacetate provided {4-[2-amino-6-(5-chloro-2-ethoxyphenyl)pyrimidin-4-ylamino]phenyl}acetic acid ethyl ester (87% yield). $^1$H NMR (DMSO-$d_6$) δ 9.14 (s, 1 H), 7.92 (d, 1 H, J=2.8 Hz), 7.63 (d, 2 H, J=8.4 Hz), 7.40 (dd, 1 H, J=8.8, 2.8 Hz), 7.12-7.19 (m, 3 H), 6.77, (s, 1 H), 6.27 (s, 2 H), 4.05-4.14 (m, 4 H), 3.59 (s, 2 H), 1.37 (t, 3 H, J=6.9 Hz), 1.18 (t, 3 H, 7.1 Hz).

To a mixture of methylmagnesium bromide (0.35 ml of a 3.0 M solution in diethyl ether) and toluene (1.5 ml), cooled in an ice bath, was added a solution of {4-[2-amino-6-(5-chloro-2-ethoxyphenyl)pyrimidin-4-ylamino]phenyl} acetic acid ethyl ester (136 mg, 0.32 mmol) in toluene (0.5 ml). After stirring for 1 hour, the mixture was treated with tetrahydrofuran (10 ml) and a solution of saturated aqueous sodium chloride and 1 M hydrochloric acid (1:1, 10 ml). The layers were separated and the aqueous layer was extracted with tetrahydrofuran (10 ml). The combined organic layers were dried over sodium sulfate, filtered, and concentrated under reduced pressure. The residue was purified by flash chromatography on silica gel eluting with methanol-ethyl acetate (5:95) to provide the title compound (42 mg, 32% yield). $^1$H NMR (DMSO-$d_6$) δ 9.06 (s, 1 H), 7.92 (d, 1 H, J=2.8 Hz), 7.54 (d, 2 H, J=8.3 Hz), 7.39 (dd, 1 H, J=8.8, 2.8 Hz), 7.10-7.13 (m, 3 H), 6.76, (s, 1 H), 6.25 (s, 2 H), 4.27 (s, 1 H), 4.26 (q, 2 H, J=7.1 Hz), 2.60 (s, 2 H), 1.36 (t, 3 H, J=7.1 Hz), 1.05 (s, 6 H).

Example 121

1-{4-[2-amino-6-(5-chloro-2-ethoxyphenyl)pyrimidin-4-ylamino]phenyl}ethanone

Following the procedure described in Example 4,4-chloro-6-(5-chloro-2-ethoxyphenyl)pyrimidin-2-yl-amine and 4'-aminoacetophenone provided the title compound (94% yield). $^1$H NMR (DMSO-$d_6$) δ 9.60 (s, 1 H), 7.88-7.93 (m, 5 H), 7.42 (dd, 1 H, J=8.8, 2.8 Hz), 7.15 (d, 1 H, J=8.9 Hz), 6.85, (s, 1 H), 6.46 (s, 2 H), 4.15 (q, 2 H, J=6.9 Hz), 2.52 (s, 3 H), 1.40 (t, 3 H, J=6.9 Hz).

Example 122

6-(5-chloro-2-ethoxyphenyl)-N*4*-(4-chlorophenyl)-N*4*-methylpyrimidine-2,4-diamine Following the procedure described in Example 4,4-chloro-6-(5-chloro-2-ethoxyphenyl)pyrimidin-2-yl-amine and 4-chloro-N-methylaniline provided the title compound (59% yield). $^1$H NMR (DMSO-$d_6$) δ 8.04 (d, 1 H, J=2.8 Hz) 7.52 (d, 2 H, J=8.6 Hz), 7.32-7.37 (m, 3 H), 7.01 (d, 1 H, J=8.9 Hz), 6.52, (s, 1 H), 6.25 (s, 2 H), 3.92 (q, 2 H, J=6.9 Hz), 3.38 (s, 3 H), 0.99 (t, 3 H, J=6.9 Hz).

Example 123

1-{4-[2-amino-6-(5-chloro-2-methylphenyl)pyrimidin4-ylamino]phenyl}ethanone

Following the procedure described in Example 4,4-chloro-6-(5-chloro-2-methylphenyl)pyrimidin-2-yl-amine and 4-aminoacetophenone provided the title compound (66% yield). $^1$H NMR (DMSO-$d_6$) δ 9.70 (s, 1 H), 7.88-7.95 (m, 4H), 7.31-7.43 (m, 3 H), 6.61, (s, 2 H), 6.20 (s, 1 H), 2.52 (s, 3 H), 2.35 (s, 3 H).

Example 124

6-(5-chloro-2-ethoxyphenyl)-N*4*-(4-methanesulfonylphenyl)pyrimidine-2,4-diamine Following the procedure described in Example 4,4-chloro-6-(5-chloro-2-ethoxyphenyl)pyrimidin-2-yl-amine and 4-methanesulfonylaniline provided the title compound (67% yield). $^1$H NMR (DMSO-$d_6$) δ 9.72 (s, 1 H), 8.03 (d, 2 H, J=8.9 Hz), 7.92 (d, 1 H, J=2.8 Hz), 7.79 (d, 2 H, J=8.9 Hz), 7.42 (dd, 1 H, J=8.8, 2.8 Hz), 7.16 (d, 1 H, J=8.9 Hz), 6.84, (s, 1 H), 6.51 (s, 2 H), 4.12 (q, 2 H, J=6.9 Hz), 3.17 (s, 3 H), 1.40 (t, 3 H, J=6.9 Hz).

Example 125

N*4*-(1H-Benzotriazol-5-yl)-6-(5-chloro-2-methylphenyl)pyrimidine-2,4-diamine

Following the procedure described in Example 4,4-chloro-6-(5-chloro-2-methylphenyl)pyrimidin-2-yl-amine and 4-aminobenzotriazole provided the title compound (66% yield). $^1$H NMR (CD$_3$OD) δ 8.62 (s, 1 H), 7.88-7.90 (m, 1 H), 7.42-7.68 (m, 4 H), 6.37 (s, 1 H), 2.42 (s, 3 H).

Example 126

6-(5-chloro-2-methylphenyl)-N*4*-(6-trifluoromethylpyridin-3-yl)pyrimidine-2,4-diamine Following the procedure described in Example 4,4-chloro-6-(5-chloro-2-methylphenyl)pyrimidin-2-yl-amine and 3-amino-6-trifluoromethylpyridine provided the title compound (49% yield). $^1$H NMR (DMSO-$d_6$) δ 9.86 (s, 1 H), 9.15 (s, 1 H), 8.49 (d, 1H, J=7.9 Hz), 7.77 (d, 1 H, J=8.7 Hz), 7.31-7.43 (m, 3 H), 6.65 (s, 2 H), 6.19 (s, 1 H), 2.35 (s, 3 H).

Example 127

1-{4-[2-amino-6-(5-bromo-2-ethoxyphenyl)pyrimidin-4-ylamino]phenyl}ethanone

Following the procedure described in Example 4,4-chloro-6-(5-bromo-2-ethoxyphenyl)pyrimidin-2-yl-amine and 4'-aminoacetophenone provided the title compound (61% yield). $^1$H NMR (DMSO-$d_6$) δ 9.61 (s, 1 H), 8.05 (d, 1 H, J=2.6 Hz), 7.88-7.93 (m, 4 H), 7.54 (dd, 1 H, J=8.8, 2.6 Hz), 7.10 (d, 1 H, J=8.9 Hz), 6.84, (s, 1 H), 6.47 (s, 2 H), 4.14 (q, 2 H, J=6.9 Hz), 2.52 (s, 3H), 1.40 (t, 3H, J=6.9 Hz).

Example 128

6-(5-bromo-2-ethoxyphenyl)-N*4*-(6-trifluoromethylpyridin-3-yl)-pyrimidine-2,4-diamine Following the procedure described in Example 4,4-chloro-6-(5-bromo-2-ethoxyphenyl)pyrimidin-2-yl-amine and 3-amino-6-trifluoromethylpyridine provided the title compound (26% yield). $^1$H NMR (DMSO-$d_6$) δ 9.81 (s, 1 H), 9.14 (s, 1 H), 8.49 (d, 1H, J=8.4 Hz), 8.06 (s, 1 H), 7.76 (d, 1 H, J=8.7 Hz), 7.55 (dd, 1 H, J=8.8, 2.4 Hz), 7.11 (d, 1 H, J=8.9 Hz), 6.85, (s, 1), 6.58 (s, 2 H), 4.15 (q, 2 H, J=6.9 Hz), 2.52 (s, 3 H), 1.41 (t, 3 H, J=6.9 Hz).

Example 129

1-{4-[2-Amino-6-(5-bromo-2-ethoxy-phenyl)-pyrimidin4-ylamino]-phenyl}-2,2,2-trifluoro-ethanol Following the method described in Example 4,4-chloro-6-(5-bromo-2-ethoxy-phenyl)-pyrimidin-2-yl-amine and 1-(4-amino-phenyl)-2,2,2-trifluoro-ethanol (Example 103) provided the title compound (39%). $^1$H NMR (DMSO-$d_6$) δ 1.37 (t, 3H, J=7.0 Hz, CH$_3$), 4.12 (q, 2H, J=7.0 Hz, CH$_2$), 5.08 (m, 1H, CH), 6.32 (s, 2H, NH$_2$), 6.70 (d, 1H, J=5.5 Hz, OH), 6.79 (s, 1H, Ar), 7.07-7.10 (m, 1H, Ar), 7.38 (d, 2H, J=8.5 Hz, Ar), 7.51 (m, 1H, Ar), 7.73 (d, 2H, J=8.5 Hz, Ar), 8.05 (s, 1H, Ar), 9.25 (s, 1H, NH).

Example 130

1-{4-[2-Amino-6-(5-bromo-2-ethoxy-phenyl)-pyrimidin4-ylamino]-phenyl}-ethanone-oxime Following the method described in Example 4,4-chloro-6-(5-bromo-2-ethoxy-phenyl)-pyrimidin-2-yl-amine and 1-(4-amino-phenyl)-ethanone-oxime (Example 104) provided the title compound (5%) $^1$H NMR (DMSO-$d_6$) δ 1.39 (t, 3H, J=6.9 Hz, CH$_3$), 2.14 (s, 3H, CH$_3$), 4.13 (q, 2H, J=6.9 Hz, CH$_2$), 6.35 (s, 2H, NH$_2$), 6.80 (s, 1H, Ar), 7.10 (d, 1H, J=8.8 Hz, Ar), 7.52-7.55 (m, 1H, Ar), 7.58 (d, 2H, J=8.6 Hz, Ar), 7.76 (d, 2H, J=8.6 Hz, Ar), 8.05 (s, 1H, Ar), 9.31 (s, 1H, NH), 11.01 (s, 1H, OH).

Example 131

1-{4-[2-Amino-6-(5-bromo-2-ethoxy-phenyl)-pyrimidin-4-ylamino]-phenyl}-2,2,2-trifluoro-ethanone To a mixture of 4-nitro-benzoic acid methyl ester (4.4 g, 24.3 mmol), trimethyl-trifluoromethyl-silane (5.0 ml, 32 mmol) and anhydrous dichloromethane (30 ml), cooled to −78° C., was added tetrabutylammonium fluoride (1 M in dichloromethane, previously dried over 4A molecular sieves, 0.6 ml). After stirring for 24 hours, the mixture was washed with saturated aqueous sodium chloride solution and concentrated under reduced pressure. The residue was purified by flash chromatography on silica gel eluting with ethyl acetate-hexane (1:10) to afford trimethyl-[2,2,2-trifluoro-1-methoxy-1-(4-nitro-phenyl)-ethoxy]-silane (5.5 g, 77% yield).

A mixture of trimethyl-[2,2,2-trifluoro-1-methoxy-1-(4-nitro-phenyl)-ethoxy]-silane (5.5 g), a solution of hydrogen chloride in dioxane (4 M, 15 ml), and water (5 ml) was stirred for 4 hours. The mixture was treated with saturated aqueous sodium chloride solution (100 ml) and extracted with ethyl acetate (100 ml). The organic extract was concentrated under reduced pressure to afford 2,2,2-trifluoro-1-(4-nitro-phenyl)-ethanone (4.5 g, 85% yield)

To a suspension of 2,2,2-trifluoro-1-(4-nitro-phenyl)-ethanone (4.5 g, 20.5 mmol) in concentrated hydrochloric acid (15 ml) and water (15 ml) was added tin (II) chloride (14 g, 74 mmol). After stirring for 24 hours, the mixture was adjusted to pH 10 by addition of aqueous sodium hydroxide solution (50%) and extracted with ethyl acetate. The organic extract was concentrated under reduced pressure. The residue was purified by flash chromatography on silica gel eluting with ethyl acetate-hexane (1:5) followed by recrystallization (ethyl acetate-hexane) to afford 1-(4-amino-phenyl)-2,2,2-trifluoro-ethanone (750 mg, 19% yield).

Following the method described in Example 4,4-chloro-6-(5-bromo-2-ethoxy-phenyl)-pyrimidin-2-yl-amine and 1-(4-amino-phenyl)-2,2,2-trifluoro-ethanone provided the title compound (28% yield). $^1$H NMR (DMSO-$d_6$) δ 1.42 (t, 3H, J=6.9 Hz, CH$_3$), 4.17 (q, 2H, J=7.0 Hz, CH$_2$), 6.60 (s, 2H, NH$_2$), 6.90 (s, 1H, Ar), 7.13 (d, 2H, J=8.9 Hz, Ar), 7.56 (m, 1H, Ar), 7.99 (d, 2H, J=8.7 Hz, Ar), 8.06 (s, 1H, Ar), 8.12 (d, 2H, J=8.9 Hz, Ar), 10.00 (s, 1H, NH).

Example 132

6-(5-Bromo-2-ethoxy-phenyl)-N*4*-(3,4-dimethyl-phenyl)-pyrimidine-2,4-diamine

Following the method described in Example 59, the hydrochloride salt of 4-chloro-6-(5-bromo-2-ethoxy-phenyl)-pyrimidin-2-ylamine and 3,4-dimethyl-phenylamine provided the title compound as the hydrochloride salt (55% yield). $^1$H NMR (CD$_3$OD) δ 1.44-1.48 (m, 3H, CH$_3$), 2.29 (s, 3H, CH$_3$), 2.33 (s, 3H, CH$_3$), 4.15-4.24 (m, 2H, CH$_2$), 6.45 (s, 1H, Ar), 7.18-7.20 (m, 2H, Ar), 7.51-7.55 (m, 2H, Ar), 7.71-7.75 (m, 2H, Ar).

Example 133

6-(5-Bromo-2-ethoxy-phenyl)-N*4*-(4-nitro-phenyl)-pyrimidine-2,4-diamine

Following the method described in Example 4, the hydrochloride salt of 4-chloro-6-(5-bromo-2-ethoxy-phenyl)-pyrimidin-2-ylamine and 4-nitroaniline provided the title compound as the hydrochloride salt (62% yield). $^1$H NMR (DMSO-$d_6$) δ 1.38 (t, 3H, J=6.9 Hz, CH$_3$), 4.17 (q, 2H, J=6.9 Hz, CH$_3$), 6.73 (s, 1H, Ar), 7.22 (d, 1H, J=9.0 Hz, Ar), 7.73-7.80 (m, 2H, Ar), 8.13 (d, 2H, J=9.1 Hz, Ar), 8.25 (d, 2H, J—9.1 Hz, Ar).

Example 134

1-{4-[2-Amino-6-(5-bromo-2-ethoxy-phenyl)-N*4*-(3,4-dimethyl-phenyl)-pyrimidin-4-ylamino]-phenyl}-ethanol Following the method described in Example 59, the hydrochloride salt of 4-chloro-6-(5-bromo-2-ethoxy-phenyl)-pyrimidin-2-ylamine and 1-(4-amino-phenyl)-ethanone provided 1-{4-[2-amino-6-(5-bromo-2-ethoxy-phenyl)-N*4*-(3,4-dimethyl-phenyl)-pyrimidin-4-ylamino]-phenyl}-ethanone (0.828 g, 71% yield).

To a stirred solution of 1-{4-[2-amino-6-(5-bromo-2-ethoxy-phenyl)-N*4*-(3,4-dimethyl-phenyl)-pyrimidin-4-ylamino]-phenyl}-ethanone in tetrahydrofuran (15 ml), cooled in an ice bath, was added lithium aluminum hydride (0.018 g, 0.468 mmol). After stirring at 0° C. for 2 hours, aqueous sodium hydroxide solution (1.0 M, 15 ml) was added carefully. The mixture was extracted with tetrahydrofuran (3×30 ml). The organic phase was dried over magnesium sulfate. Evaporation of the solvent under reduced pressure provided the title compound (0.033 g, 33% yield) as a white powder. $^1$H NMR (DMSO-$d_6$) δ 1.32 (d, 3H, J=6.4 Hz, CH$_3$), 1.38 (t, 3H, J=6.9 Hz, CH$_3$), 4.12 (q, 2H, J=6.9 Hz, CH$_2$), 4.66-4.72 (m, 1H, CH), 5.05 (d, 1H, J=4.1 Hz, OH), 6.25 (s, 2H, NH$_2$), 6.77 (s, 1H, Ar), 7.09 (d, 1H, J=8.9 Hz, Ar), 7.26 (d, 2H, J=8.4 Hz, Ar), 7.52 (dd, 1H, J=8.8 Hz, J=2.5 Hz, Ar), 7.60 (d, 2H, J=8.3 Hz, Ar), 8.07 (d, 1H, J=2.6 Hz, Ar), 9.09 (s, 1H, NH).

Example 135

6-(5-Bromo-2-propoxy-phenyl)-N*4*-(4-chloro-phenyl)-pyrimidine-2,4-diamine

To the stirred solution of 2-(2-amino-6-chloro-pyrimidin-4-yl)-4-bromo-phenol (0.060 g, 0.20 mmol), 1-propanol (0.036 g, 0.60 mmol), and triphenylphosphine (0.157 g, 0.60 mmol) in tetrahydrofuran (5.0 ml) was added diethyl azodicarboxylate (0.104 g, 0.60 mmol). After stirring for 16 hours, the mixture was concentrated under reduced pressure. The residue was purified by flash chromatography on silica gel eluting with ethyl acetate-hexane (1:6) to provide 4-(5-bromo-2-propoxy-phenyl)-6-chloro-pyrimidin-2-ylamine (0.036 g, 52% yield) as a white powder.

Following the method described in Example 4,4-(5-bromo-2-propoxy-phenyl)-6-chloro-pyrimidin-2-ylamine and 4-chloroaniline provided the title compound (63% yield). $^1$H NMR (DMSO-$d_6$) δ 0.94 (t, 3H, J=7.4 Hz, $CH_3$), 1.73-1.79 (m, 2H, $CH_2$), 4.01 (t, 3H, J=6.6 Hz, $CH_2$), 6.34 (s, 2H, $NH_2$), 6.72 (s, 1H, Ar), 7.09 (d, 1H, J=8.9 Hz, Ar), 7.31 (d, 2H, J=8.8 Hz, Ar), 7.52 (dd, 1H, J=8.8 Hz, J=2.6 Hz, Ar), 7.76 (d, 2H, J=8.7 Hz, Ar), 8.01 (d, 1H, J=2.6 Hz, Ar), 9.27 (s, 1H, NH).

Example 136

6-(5-Bromo-2-isopropoxy-phenyl)-N*4*-(4-chloro-phenyl)-pyrimidine-2,4-diamine Following the method described in Example 135 for the synthesis of 4-(5-bromo-2-propoxy-phenyl)-6-chloro-pyrimidin-2-ylamine, 2-(2-amino-6-chloro-pyrimidin-4-yl)-4-bromo-phenol and 2-propanol provided 4-(5-bromo-2-isopropoxy-phenyl)-6-chloro-pyrimidin-2-ylamine (68% yield).

Following the method described in Example 4,4-(5-bromo-2-isopropoxy-phenyl)-6-chloro-pyrimidin-2-ylamine and 4-chloro-phenylamine provided the title compound (83% yield). $^1$H NMR (DMSO-$d_6$) δ 1.73-1.79 (m, 2H, $CH_2$), 4.01 (t, 3H, J=6.6 Hz, $CH_2$), 6.34 (s, 2H, $NH_2$), 6.72 (s, 1H, Ar), 7.09 (d, 1H, J=8.9 Hz, Ar), 7.31 (d, 2H, J=8.8 Hz, Ar), 7.52 (dd, 1H, J=8.8 Hz, J=2.6 Hz, Ar), 7.76 (d, 2H, J=8.7 Hz, Ar), 8.01 (d, 1H, J=2.6 Hz, Ar), 9.27 (s, 1H, NH).

Example 137

6-(5-Bromo-2-ethoxy-phenyl)-N*4*-[4-(1-methoxy-ethyl)-phenyl]-pyrimidin-2,4-diamine Following the method described in Example 4,4-chloro-6-(5-bromo-2-ethoxy-phenyl)-pyrimidin-2-ylamine and 1-(4-amino-phenyl)-ethanol provided the title compound (24% yield). $^1$H NMR (DMSO-$d_6$) δ 1.33-1.39 (m, 6H, $CH_3$), 3.11 (s, 3H, $CH_3$), 4.12 (q, 2H, J=6.9 Hz, $CH_2$), 4.27 (q, 1H, J=6.3 Hz, CH), 6.28 (s, 2H, $NH_2$), 6.80 (s, 1H, Ar), 7.09 (d, 1H, J=8.9 Hz, Ar), 7.22 (d, 2H, J=8.9 Hz, Ar), 7.51-7.54 (m, 1H, Ar), 7.65 (d, 2H, J=8.1 Hz, Ar), 8.07-8.08 (m, 1H, Ar), 9.15 (s, 1H, NH).

Example 138

3-[2-Amino-6-(5-Bromo-2-ethoxy-phenyl)-pyrimidin-4yl-amino]-benzamide

Following the method described in Example 4, the hydrochloride salt of 4-chloro-6-(5-bromo-2-ethoxy-phenyl)-pyrimidin-2-ylamine and 3-amino-benzamide provided the title compound as the hydrochloride salt (73% yield). $^1$H NMR ($CD_3OD$) δ 1.44-1.48 (m, 3H, $CH_3$), 4.18-4.25 (m, 2H, $CH_2$), 6.52 (s, 1H, Ar), 7.19 (d, 1H, J=8.6 Hz, Ar), 7.52 (t, 1H, J=7.9 Hz, Ar), 7.71-7.75 (m, 4H, Ar), 7.83 (d, 1H, J=7.7 Hz, Ar), 8.54 (s, 1H, NH).

Example 139

1-{4-[2-Amino-6-(3-chloro-phenyl)-pyrimidin-4-ylamino]-phenyl}-ethanone

Following the method described in Example 4,3-chloro-phenyl boronic acid and 4,6-dichloro-pyrimidin-2-yl-amine provided 4-chloro-6-(3-chloro-phenyl)-pyrimidin-2-yl-amine (60% yield).

Following the method described in Example 4,4-chloro-6-(3-chloro-phenyl)-pyrimidin-2-yl-amine and 1-(4-amino-phenyl)-ethanone provided the title compound (45% yield). $^1$H NMR (DMSO-$d_6$) δ 2.54 (s, 3H, $CH_3$), 6.61 (m, 3H, Ar), 7.54-7.56 (m, 2H, $NH_2$), 7.86-7.88 (m, 1H, Ar), 7.93 (q, 4H, J=8.9 Hz, Ar), 8.02 (s, 1H, Ar), 9.72 (s, 1H, NH).

Example 140

N*4*-{4-Azido-phenyl)-6-(2-ethoxy-5-iodo-phenyl)-pyrimidine-2,4-diamine

To a solution of 4-chloro-6-(5-bromo-2-ethoxy-phenyl) pyrimidin-2-ylamine (1.60 g, 4.9 mmol), synthesized as described in Example 59, in dimethylformamide (15 ml) was added bistributyl tin (5.7 g, 9.8 mmol) followed by bistriphenylphosphine palladium dibromide (0.39 g, 0.49 mmol). The mixture was degassed, and stirred under an atmosphere of argon at 95° C. for 16 hours. After cooling to room temperature, the mixture was treated with water (100 ml) and extracted with ethyl acetate (3×50 ml). The combined extracts were washed with a 30% aqueous potassium carbonate solution (25 ml) and with water (100 ml). The organic layer was dried over sodium sulfate and concentrated under reduced pressure. The residue was purified by flash chromatography on a silica gel eluting with 10% ethyl acetate-hexane to yield 4-chloro-6-(5-tributylstannyl-2-ethoxy-phenyl)pyrimidin-2-ylamine (343 mg, 15% yield) as a colorless oil. $^1$H NMR ($CDCl_3$) δ 7.90 (d, J=2.2 Hz, 1H), 7.47 (dd, J=2.1, 8.1 Hz, 1H), 6.98 (d, J=8.1 Hz, 1H), 4.13 (q, J=6.9 Hz, 2H), 1.45-1.76 (m, 6H), 1.37 (t, J=7.0 Hz, 3H), 1.34-1.36 (m, 6H), 1.05-1.09 (m, 6H), 0.89-0.93 (m, 9H).

To a solution of 4-chloro-6-(5-tributylstannyl-2-ethoxy-phenyl)pyrimidin-2-ylamine (79 mg, 0.13 mmol) in a 3% solution of acetic acid in ethanol (1 ml) was added a solution of sodium iodide (24 mg, 0.16 mmol) in a 0.1 M aqueous sodium hydroxide solution (0.2 ml) followed by a solution of chloramine-T (15.0 mg, 0.065 mmol) in water (0.15 ml). The orange solution was stirred at room temperature for 1 hour, treated with saturated aqueous sodium thiosulfate solution (0.3 ml), and extracted with ethyl acetate (2×1 ml). The combined extracts were concentrated under reduced pressure. The residue was purified by preparative TLC eluting with 20% ethyl acetate-hexane to provide 4-chloro-6-(5-iodo-2-ethoxy-phenyl)pyrimidin-2-ylamine (39 mg, 71% yield) as a white powder. $^1$H NMR ($CDCl_3$) δ 8.24 (d, J=2.3 Hz, 1H), 7.67 (dd, J=2.3, 8.70 Hz, 1H), 7.38 (d, J=8.70 Hz, 2H), s, 1H), 6.76 (d, J=8.70 Hz, 1H), 5.23 (s, 1H), 4.13 (q, J=7.0 Hz, 2H), 1.47 (t, J=7.0 Hz, 3H).

To a mixture of 4-chloro-6-(5-iodo-2-ethoxy-phenyl)pyrimidin-2-ylamine (7.0 mg, 0.02 mmol) and 4-azidoaniline hydrochloride (5.0 mg, 0.03 mmol) in tert-butanol (1 ml) was added a 1 M hydrogen chloride in dioxane (0.2 ml). The mixture was heated at 90° C. for 2 hours. After cooling to room temperature, the mixture was treated with 1 M aqueous sodium bicarbonate solution (1 ml) and extracted with ethyl acetate (2×1 ml). The combined extracts were concentrated under reduced pressure and the residue was purified by preparative TLC eluting with 35% ethyl acetate-hexane to provide the title compound (6 mg, 68% yield) as a light brown solid. $^1$H NMR (CDCl$_3$) δ 8.20 (d, J=2.3 Hz, 1H), 7.60 (dd, J=2.3, 8.70 Hz, 1H), 7.38 (d, J=8.70 Hz, 2H), 7.04 (d, J=8.70 Hz, 2H), 6.77 (s, 1H), 6.72 (d, J=5.0 Hz, 1H), 6.63 (br s, 1H), 4.91 (br s, 2H), 4.09 (q, J=7.0 Hz, 2H), 1.38 (t, J=7.0 Hz, 3H).

Example 141

2-{4-[2-Amino-6-(5-bromo-2-isopropoxy-phenyl)-pyrimidin-4-ylamino]-phenyl}-ethanol Following the method described in Example 135 for the synthesis of 4-(5-bromo-2-propoxy-phenyl)-6-chloro-pyrimidin-2-ylamine, 2-(2-amino-6-chloro-pyrimidin-4-yl)-4-bromo-phenol and propan-2-ol provided 4-(5-bromo-2-isopropoxy-phenyl)-6-chloro-pyrimidin-2-ylamine (68% yield).

Following the method described in Example 4,4-(5-bromo-2-isopropoxy-phenyl)-6-chloro-pyrimidin-2-ylamine and 2-(4-amino-phenyl)-ethanol provided the title compound (55% yield) as its hydrochloride salt. $^1$H NMR (DMSO-16) δ 1.31 (s, 6H, CH$_3$), 2.72 (d, 2H, J=7.0 Hz, CH$_2$), 3.60 (t, 3H, J=7.0 Hz, CH$_2$), 4.70-4.75 (m, 1H, CH), 6.58 (s, 1H, Ar), 7.26-7.27 (m, 3H, Ar), 7.62-7.75 (m, 4H, Ar), 10.77 (s, 1H), 12.39 (s, 1H).

Example 142

6-(5-Bromo-2-methoxy-phenyl)-N*4*-(4-chloro-phenyl)-pyrimidine-2,4-diamine

Following the method described in Example 4 for the synthesis of 4-chloro-6-(5-chloro-2-methoxy-phenyl)-pyrimidin-2-yl-amine, 4,6-dichloro-pyrimidin-2-yl-amine and 5-bromo-2-methoxy-phenyl boronic acid provided 4-chloro-6-(5-bromo-2-methoxy-phenyl)-pyrimidin-2-yl-amine (53% yield).

Following the method described in Example 4,4-chloro-6-(5-bromo-2-methoxy-phenyl)-pyrimidin-2-yl-amine and 4-chloro-phenylamine provided the title compound (85% yield) as its hydrochloride salt. $^1$H NMR (CD$_3$OD) δ 3.96 (s, 3H, CH$_3$), 6.49 (s, 1H, Ar), 7.20 (d, 1H, J=9.6 Hz, Ar), 7.41 (d, 2H, J=8.8 Hz, Ar), 7.72-7.82 (m, 4H, Ar).

Example 143

6-[5-Bromo-2-(2-methoxy-ethoxy)-phenyl]-N*4*-(4-chloro-phenyl)-pyrimidine-2,4-diamine Following the method described in Example 135 for the synthesis of 4-(5-bromo-2-propoxy-phenyl)-6-chloro-pyrimidin-2-ylamine, 2-(2-amino-6-chloro-pyrimidin-4-yl)-4-bromo-phenol and 2-methoxy-ethanol provided 4-[5-bromo-2-(2-methoxy-ethoxy)-phenyl]-6-chloro-pyrimidin-2-ylamine (42% yield).

Following the method described in Example 4, 4-[5-bromo-2-(2-methoxy-ethoxy)-phenyl]-6-chloro-pyrimidin-2-ylamine and 4-chloro-phenylamine provided the title compound (79% yield). $^1$H NMR (DMSO-d$_6$) δ 3.26 (s, 3H, CH$_3$), 3.71 (t, 2H, J=4.7 Hz, CH$_2$), 4.19 (t, 2H, J=4.4 Hz, CH$_2$), 6.36 (s, 2H, NH$_2$), 6.74 (s, 1H, Ar), 7.11 (d, 1H, J=8.8 Hz, Ar), 7.31 (d, 2H, J=8.8 Hz, Ar), 7.52 (dd, 1H, J=8.8 Hz, J=2.6 Hz, Ar), 7.76 (d, 2H, J=8.7 Hz, Ar), 8.01 (d, 1H, J=2.6 Hz, Ar), 9.27 (s, 1H, NH).

Example 144

6-(5-Bromo-2-ethoxy-phenyl)-N*4*-quinolin-3-yl-pyrimidine-2,4-diamine

Following the method described in Example 4,4-(5-bromo-2-ethoxy-phenyl)-6-chloro-pyrimidin-2-ylamine and quinolin-3-ylamine provided the title compound (88% yield) as its hydrochloride salt. $^1$H NMR (CD$_3$OD) δ 1.46 (t, 3H, J=7.0 Hz, CH$_3$), 4.22 (q, 2H, J=7.0 Hz, CH$_2$), 6.61 (s, 1H, Ar), 7.19 (d, 1H, J=8.9 Hz, Ar), 7.67-7.77 (m, 4H, Ar), 8.00-8.05 (m, 2H, Ar), 9.05-9.06 (m, 2H).

Example 145

6-(5-Bromo-2-hexyloxy-phenyl)-N*4*-(4-chloro-phenyl)-pyrimidine-2,4-diamine

Following the method described in Example 135 for the synthesis of 4-(5-bromo-2-propoxy-phenyl)-6-chloro-pyrimidin-2-ylamine, 2-(2-amino-6-chloro-pyrimidin-4-yl)-4-bromo-phenol and hexan-1-ol provided 4-(5-bromo-2-hexyloxy-phenyl)-6-chloro-pyrimidin-2-ylamine (47% yield).

Following the method described in Example 4,4-(5-bromo-2-hexyloxy-phenyl)-6-chloro-pyrimidin-2-ylamine and 4-chloro-phenylamine provided the title compound (80% yield) as its hydrochloride salt. $^1$H NMR (CD$_3$OD) δ 0.88 (t, 3H, J=7.1 Hz, CH$_3$), 1.30-1.44 (m, 6H, CH$_2$), 1.79-1.83 (m, 2H, CH$_2$), 4.13 (t, 2H, J=6.3 Hz, CH$_2$), 6.45 (s, 1H, Ar), 7.17 (d, 1H, J=9.6 Hz, Ar), 7.42 (d, 2H, J=8.8 Hz, Ar), 7.69-7.79 (m, 4H, Ar).

Example 146

6-(2-Benzyloxy-5-bromo-phenyl)-N*4*-(4-chloro-phenyl)-pyrimidine-2,4-diamine

Following the method described in Example 135 for the synthesis of 4-(5-bromo-2-propoxy-phenyl)-6-chloro-pyrimidin-2-ylamine, 2-(2-amino-6-chloro-pyrimidin-4-yl)-4-bromo-phenol and benzyl alcohol provided 4-(2-benzyloxy-5-bromo-phenyl)-6-chloro-pyrimidin-2-ylamine (43% yield).

Following the method described in Example 4,4-(2-benzyloxy-5-bromo-phenyl)-6-chloro-pyrimidin-2-ylamine and 4-chloro-phenylamine provided the title compound (65% yield) as its hydrochloride salt. $^1$H NMR (CD$_3$OD) δ 5.25 (s, 2H, CH$_2$), 6.44 (s, 1H, Ar), 7.26-7.41 (m, 8H, Ar), 7.70-7.81 (m, 4H, Ar).

Example 147

1-{4-[2-Amino-6-(2,3,5-trichloro-phenyl)-pyrimidin-4-ylamino]-phenyl}-ethanone oxime A mixture of 2,3,5-trichloro-phenyl boronic acid (12 g, 53 mmol) and 4,6-dichloro-pyrimidin-2-yl-amine (10.5 g, 64 mmol) in ethylene glycol dimethyl ether (300 ml) under Argon atmosphere was stirred for 30 minutes. A mixture of palladium (II) acetate (1.8 g, 8 mmol), a solution of sodium carbonate (28.2 g, 270 mmol) in water (100 ml), and triphenylphosphine (4.2 g, 16 mmol) were added and the mixture was stirred for 18 hours. The mixture was treated with acetone (500 ml), filtered through a pad of celite under suction and concentrated under reduced pressure. The residue was treated with water (100 ml) and the mixture was stirred vigorously. The solid was filtered and dissolved in tetrahydrofuran (100 ml). Hydrogen chloride (4 M in dioxane, 20 ml) was added. After stirring for 1 hour, the solid was filtered and dried under reduced pressure. The solid was treated with ethyl acetate (50 ml) and stirred for 30 minutes. The solid was filtered and dried under reduced pressure to afford 4-chloro-6-(2,3,5-trichloro-phenyl)-pyrimidin-2-yl-amine-hydrochloride salt (3.7 g, 20% yield) as a white powder.

Following the method described in Example 4,4-chloro-6-(2,3,5-trichloro-phenyl)-pyrimidin-2-yl-amine-hydrochloride salt and 1-(4-amino-phenyl)-ethanone oxime provided the title compound (12% yield). $^1$H NMR (DMSO-d$_6$) δ 2.12 (s, 3H, CH$_3$), 6.24 (s, 1H, Ar), 6.52 (s, 2H, NH$_2$), 7.56-7.58 (m, 3H, Ar), 7.75-7.78 (m, 2H, Ar), 7.92 (s, 1H, Ar), 9.43 (s, 1H, NH), 11.00 (s, 1H, OH).

Example 148

6-(5-Bromo-2-butoxy-phenyl)-N*4*-(4-chloro-phenyl)-pyrimidine-2,4-diamine

Following the method described in Example 135 for the synthesis of 4-(5-bromo-2-propoxy-phenyl)-6-chloro-pyrimidin-2-ylamine, 2-(2-amino-6-chloro-pyrimidin-4-yl)-4-bromo-phenol and butan-1-ol provided 4-(5-bromo-2-butoxy-phenyl)-6-chloro-pyrimidin-2-ylamine (51% yield).

Following the method described in Example 4,4-(5-bromo-2-butoxy-phenyl)-6-chloro-pyrimidin-2-ylamine and 4-chloro-phenylamine provided the title compound (71% yield) as its hydrochloride salt. $^1$H NMR (CD$_3$OD) δ 0.98 (t, 3H, J=7.4 Hz, CH$_3$), 1.45-1.51 (m, 2H, CH$_2$), 1.79-1.83 (m, 2H, CH$_2$), 4.13 (t, 2H, J=6.2 Hz, CH$_2$), 6.45 (s, 1H, Ar), 7.17-7.54 (m, 5H, Ar), 7.70-7.83 (m, 4H, Ar).

Example 149

6-[5-Bromo-2-(2-morpholin4-yl-ethoxy)-phenyl]-N*4*-(4-chloro-phenyl)-pyrimidine-2,4-diamine Following the method described in Example 135 for the synthesis of 4-(5-bromo-2-propoxy-phenyl)-6-chloro-pyrimidin-2-ylamine, 2-(2-amino-6-chloro-pyrimidin-4-yl)-4-bromo-phenol and 2-morpholin-4-yl-ethanol provided 4-[5-bromo-2-(2-morpholin-4-yl-ethoxy)-phenyl]-6-chloro-pyrimidin-2-ylamine (41% yield).

Following the method described in Example 4, 4-[5-bromo-2-(2-morpholin-4-yl-ethoxy)-phenyl]-6-chloro-pyrimidin-2-ylamine and 4-chloro-phenylamine provided the title compound (83% yield). $^1$H NMR (CDCl$_3$) δ 2.47 (m, 4H, 2CH$_2$), 2.68 (t, 2H, J=5.6 Hz, CH$_2$), 3.67 (m, 4H, 2CH$_2$), 4.09 (t, 2H, J=5.7 Hz, CH$_2$), 4.95 (s, 2H, NH$_2$), 6.72-6.84 (m, 3H, Ar), 7.28-7.33 (m, 2H, Ar), 7.42-7.45 (m, 1H, Ar), 7.99 (s, 1H, Ar).

Example 150

6-(5-Bromo-2-methoxy-phenyl)-N*4*-(4-trifluoromethyl-phenyl)-pyrimidine-2,4-diamine Following the method described in Example 4,4-chloro-6-(5-bromo-2-methoxy-phenyl)-pyrimidin-2-yl-amine and 4-trifluoromethyl-phenylamine provided the title compound (90% yield). $^1$H NMR (d$_6$-DMSO) δ 3.89 (s, 3H, CH$_3$), 6.46 (s, 2H, NH$_2$), 6.79 (s, 1H, Ar), 7.12 (d, 1H, J=8.9 Hz, Ar), 7.56-7.61 (m, 3H, Ar), 7.99-8.06 (m, 3H, Ar), 9.63 (s, 1H, NH).

Example 151

2-{4-[2-Amino-6-(5-bromo-2-methoxy-phenyl)-pyrimidin-4-ylamino]-phenyl}-ethanol

Following the method described in Example 4,4-chloro-6-(5-bromo-2-methoxy-phenyl)-pyrimidin-2-yl-amine and 2-(4-amino-phenyl)-ethanol provided the title compound (79% yield) as its hydrochloride salt. $^1$H NMR (CD$_3$OD) δ 2.84 (t, 2H, J=7.0 Hz, CH$_2$), 3.77 (t, 2H, J=7.0 Hz, CH$_2$), 3.96 (s, 3H, CH$_3$), 6.46 (s, 1H, Ar), 7.20 (d, 1H, J=9.6 Hz, Ar), 7.28 (d, 2H, J=8.1 Hz, Ar), 7.70-7.74 (m, 4H, Ar).

Example 152

N*4*-(4-Chloro-phenyl)-6-(2-phenoxy-phenyl)-pyrimidin-2,4-diamine

Following the method described in Example 4,2-phenoxy-phenyl boronic acid and 4,6-dichloro-pyrimidin-2-yl-amine provided 4-chloro-6-(2-phenoxy-phenyl)-pyrimidin-2-yl-amine (26% yield).

Following the method described in Example 4,4-chloro-6-(2-phenoxy-phenyl)-pyrimidin-2-yl-amine and 4-chloro-aniline provided the title compound (50% yield). $^1$H NMR (DMSO-d$_6$) δ 6.34 (s, 2H, NH$_2$), 6.64 (s, 1H, Ar), 6.95-6.97 (m, 3H, Ar), 7.11 (t, 1H, J=7.7 Hz, Ar), 7.25-7.28 (m, 3H, Ar), 7.35-7.37 (m, 2H, Ar), 7.39 (m, 1H, Ar), 7.74 (d, 2H, J=8.9 Hz, Ar) 7.93 (dd, 1H, J=7.7 Hz, J=1.6 Hz, Ar), 9.29 (s, 1H, NH).

Example 153

6-(2-Benzyloxy-5-bromo-phenyl)-N*4*-(4-trifluoromethyl-phenyl)-pyrimidine-2,4-diamine Following the method described in Example 4,4-(2-benzyloxy-5-bromo-phenyl)-6-chloro-pyrimidin-2-ylamine and 4-trifluoromethyl-phenylamine provided the title compound (60% yield). $^1$H NMR (DMSO-d$_6$) δ 5.28 (s, 2H, CH$_2$), 6.48 (s, 2H, NH$_2$), 6.82 (s, 1H, Ar), 7.14 (d, 1H, J=8.9 Hz, Ar), 7.29-7.37 (m, 3H, Ar), 7.44 (d, 2H, J=7.4 Hz, Ar), 7.52 (dd, 1H, J=8.8 Hz, J=2.6 Hz, Ar), 7.57 (d, 2H, J=8.6 Hz, Ar), 7.93-7.96 (m, 3H, Ar), 9.60 (s, 1H, NH).

Example 154

1-{4-[2-Amino-6-(2,5-dichloro-phenyl)-pyrimidin-4-yl-amino]-phenyl}-ethanone oxime Following the method described in Example 4, the hydrochloride salt of 4-chloro-6-(2,5-dichloro-phenyl)-pyrimidin-2-ylamine and 1-(4-amino-phenyl)-ethanone provided 1-{4-[2-amino-6-(2,5-dichloro-phenyl)-pyrimidin-4-yl-amino]-phenyl}-ethanone as the hydrochloride salt (60% yield).

A mixture of 1-{4-[2-amino-6-(2,5-dichloro-phenyl)-pyrimidin-4-yl-amino]-phenyl}-ethanone, hydroxylamine hydrochloride, 0.6 M aqueous sodium hydroxide solution (2 ml), and ethanol (20 ml) was stirred 16 hours. The mixture was extracted with tetrahydrofuran (3×15 ml). The combined extracts were dried over magnesium sulfate and concentrated under reduced pressure. The residue was purified by column chromatography on alumina eluting with 7% methanol-chloroform to provide the title compound (0.010 g, 10% yield). $^1$H NMR (DMSO-d$_6$) δ 2.14 (s, 3H, CH$_3$), 6.34 (s, 1H, Ar), 7.51-0.754 (m, 1H, Ar), 7.58-7.61 (m, 3H, Ar), 7.65 (d, 1H, J=2.5 Hz, Ar), 7.79 (d, 2H, J=8.8 Hz, Ar), 9.46 (s, 1H, NH), 11.02 (s, 1H, OH).

Example 155

6-(2-Benzyloxy-5-chloro-phenyl)-N*4*-(4-chloro-phenyl)-pyrimidine-2,4-diamine

Following the method described in Example 72, 2-(2-amino-6-chloro-pyrimidin-4-yl)-4-chloro-phenol and bromomethyl-benzene provided 4-(2-benzyloxy-5-chloro-phenyl)-6-chloro-pyrimidin-2-ylamine (56% yield).

Following the method described in Example 72, 4-(2-benzyloxy-5-chloro-phenyl)-6-chloro-pyrimidin-2-ylamine and 4-chloro-aniline provided the title compound (98% yield). $^1$H NMR (CD$_3$OD) δ 5.26 (s, 2H, CH$_2$), 6.44 (s, 1H, Ar), 7.21 (d, 1H, J=8.8 Hz, Ar), 7.33-7.36 (m, 2H, Ar), 7.38-7.43 (m, 4H, Ar), 7.45 (d, 1H, J=8.8 Hz, Ar), 7.58-7.61 (m, 2H, Ar), 7.80-7.82 (m, 2H, Ar).

Example 156

6-[5-Bromo-2-(3-dimethylamino-propoxy)-phenyl]-N*4*-(4-chloro-phenyl)-pyrimidine-2,4-diamine Following the method described in Example 135 for the synthesis of 4-(5-bromo-2-propoxy-phenyl)-6-chloro-pyrimidin-2-ylamine, 2-(2-amino-6-chloro-pyrimidin-4-yl)-4-bromo-phenol and 3-dimethylamino-propan-1-ol provided 4-[5-bromo-2-(3-dimethylamino-propoxy)-phenyl]-6-chloro-pyrimidin-2-ylamine (43% yield).

Following the method described in Example 4, 4-[5-bromo-2-(3-dimethylamino-propoxy)-phenyl]-6-chloro-pyrimidin-2-ylamine and 4-chloro-phenylamine provided the title compound (55% yield) as its hydrochloride salt. $^1$H NMR (CD$_3$OD) δ 2.28-2.32 (m, 2H, CH$_2$), 2.92 (s, 6H, CH$_3$), 3.28-3.36 (m, 2H, CH$_2$), 4.25 (m, 2H, CH$_2$), 6.51 (s, 1H, Ar), 7.20-7.22 (m, 1H, Ar), 7.41-7.43 (m, 2H, Ar), 7.73-7.76 (m, 2H, Ar), 7.85-7.86 (m, 2H, Ar).

Example 157

6-(2-Benzyloxy-S-chloro-phenyl)-N*4*-(4-trifluoromethyl-phenyl)-pyrimidine-2,4-diamine Following the method described in Example 4, 4-(2-benzyloxy-5-chloro-phenyl)-6-chloro-pyrimidin-2-ylamine and 4-chloro-aniline provided the title compound (68% yield). $^1$H NMR (CD$_3$OD) δ 5.27 (s, 2H, CH$_2$), 6.51 (s, 1H, Ar), 7.34-7.36 (m, 2H, Ar), 7.38 (s, 1H, Ar), 7.40-7.42 (m, 3H, Ar), 7.58-7.62 (m, 2H, Ar), 7.71 (d, 2H, J=8.6 Hz, Ar), 7.99-8.02 (m, 2H, Ar).

Example 158

2-[4-{2-Amino-6-(2-benzyloxy-5-chloro-phenyl)-pyrimidin4-ylamino]-phenyl}-ethanol Following the method described in Example 72, 4-(2-benzyloxy-5-chloro-phenyl)-6-chloro-pyrimidin-2-ylamine and 2-(4-amino-phenyl)-ethanol provided the title compound (71% yield). $^1$H NMR (CD$_3$OD) δ 2.85 (t, 2H, J=6.9 Hz, CH$_2$), 3.78 (t, 2H, J=6.9 Hz, CH$_2$), 5.27 (s, 2H, CH$_2$), 6.42 (s, 1H, Ar), 7.28-7.30 (m, 2H, Ar), 7.32-7.36 (m, 2H, Ar), 7.39 (d, 4H, J=6.3 Hz, Ar), 7.58 (d, 2H, J=8.4 Hz, Ar), 7.68-7.70 (m, 2H, Ar).

Example 159

4-[2-Amino-6-(5-bromo-2-ethoxy-phenyl)-pyrimidin-4-ylamino]-phenyl-boronic acid

Following the method described in Example 4,4-chloro-6-(5-bromo-2-ethoxy-phenyl)-pyrimidin-2-yl-amine and 4-amino-phenyl-boronic acid provided the title compound (31% yield) as its hydrochloride salt. $^1$H NMR (CD$_3$OD) δ 1.45 (t, 3H, J=6.9 Hz, CH$_3$), 4.20 (q, 2H, J=6.9 Hz, CH$_2$), 6.50 (s, 1H, Ar), 7.17 (d, 2H, J=9.6 Hz, Ar), 7.68-7.81 (m, 5H, Ar).

Example 160

4-[2-Amino-6-(5-bromo-2-methoxy-phenyl)-pyrimidin4-ylamino]-benzonitrile

Following the method described in Example 4,4-chloro-6-(5-bromo-2-methoxy-phenyl)-pyrimidin-2-yl-amine and 4-amino-benzonitrile provided the title compound (97% yield) as its hydrochloride salt. $^1$H NMR (DMSO-d$_6$) δ 3.89 (s, 3H, CH$_3$), 6.72 (s, 1H, Ar), 7.25 (d, 1H, J=8.9 Hz, Ar), 7.76-7.78 (m, 2H, Ar), 7.85 (d, 2H, J=8.7 Hz, Ar), 8.07 (d, 2H, J=8.5 Hz, Ar).

Example 161

6-(5-Bromo-2-methoxy-phenyl)-N*4*-(4-nitro-phenyl)-pyrimidine-2,4-diamine

Following the method described in Example 4,4-chloro-6-(5-bromo-2-methoxy-phenyl)-pyrimidin-2-yl-amine and 4-nitro-phenylamine provided the title compound (68% yield) as its hydrochloride salt. $^1$H NMR (DMSO-d$_6$) δ 3.86 (s, 3H, CH$_3$), 6.82 (s, 1H, Ar), 7.25 (d, 1H, J=8.9 Hz, Ar), 7.76-7.82 (m, 2H, Ar), 8.16-8.25 (m, 4H, Ar), 11.94 (s, 1H), 13.00 (s, 1H).

Example 162

6-(5-Bromo-2-methoxy-phenyl)-N*4*-(4-bromo-phenyl)-pyrimidine-2,4-diamine

Following the method described in Example 4,4-chloro-6-(5-bromo-2-methoxy-phenyl)-pyrimidin-2-yl-amine and 4-bromo-phenylamine provided the title compound (87% yield) as its hydrochloride salt. $^1$H NMR (DMSO-d$_6$) δ 3.89 (s, 3H, CH$_3$), 6.64 (s, 1H, Ar), 7.24 (d, 1H, J=9.5 Hz, Ar), 7.57 (d, 2H, J=8.9 Hz, Ar), 7.75-7.82 (m, 4H, Ar), 10.99 (s, 1H), 12.64 (s, 1H).

Example 163

N*4*-(4-Bromo-phenyl)-6-(5-chloro-2-ethyl-phenyl)-pyrimidine-2,4-diamine

A mixture of sodium periodate (12 g, 56 mmol), iodine (9.5 g, 37 mmol), acetic acid (80 ml) and acetic anhydride (40 ml) was cooled to 0° C. Sulfuric acid (18 ml) was added dropwise followed by 1-chloro-4-ethyl benzene (15 ml, 110 mmol) dropwise. After stirring for 18 hours, a solution of sodium sulfite (20 g) in water (300 ml) was added. The mixture was adjusted to about pH 7 by addition of 50% aqueous sodium hydroxide solution and treated with ethyl acetate (200 ml) and saturated aqueous sodium chloride solution (200 ml). The organic layer was dried over sodium sulfate and concentrated under reduced pressure. The residual oil was purified by vacuum distillation (95-100° C., 5-10 mm) followed by flash chromatography on silica gel eluting with hexane to afford 4-chloro-1-ethyl-2-iodo-benzene (7.5 g, 25% yield) as a colorless oil.

To a solution of 4-chloro-1-ethyl-2-iodo-benzene (5 g, 18.8 mmol) in anhydrous tetrahydrofuran (40 ml), cooled to −30° C., was added isopropyl magnesium chloride (2 M in tetrahydrofuran, 10 ml, 20 mmol) dropwise. After stirring at −30° C. for 30 minutes, trimethyl borate (4.2 ml, 38 mmol) was added dropwise and the mixture was stirred for 1.5 hours. The mixture was treated with hydrochloric acid (1 M, 25 ml), ethyl acetate (100 ml), and saturated aqueous sodium chloride solution (100 ml). The organic layer was dried over sodium sulfate and concentrated under reduced pressure. The residue was treated with hexane (50 ml) and the solid was filtered to afford 5-chloro-2-ethyl-phenyl boronic acid (1.8 g, 52% yield) as a white powder.

Following the method described in Example 4,5-chloro-2-ethyl-phenyl boronic acid and 4,6-dichloro-pyrimidin-2-yl-amine provided 4-chloro-6-(5-chloro-2-ethyl-phenyl)-pyrimidin-2-yl-amine as the hydrochloride salt (1.7 g, 45% yield) which on reaction with 4-bromo-aniline provided the title compound (60% yield). $^1$H NMR (DMSO-d$_6$) δ 1.11 (t, 3H, J=7.5 Hz, CH$_3$), 2.51 (q, 2H, J=7.5 Hz, CH$_2$), 6.10 (s, 1H, Ar), 6.60 (s, 2H, NH$_2$), 7.34-7.47 (m, 5H, Ar), 7.78 (d, 2H, J=8.5 Hz, Ar), 9.50 (s, 1H, NH).

Example 164

6-(5-Chloro-2-ethyl-phenyl)-N*4*-(4-trifluoromethyl-phenyl)-pyrimidine-2,4-diamine Following the method described in Example 4,5-chloro-2-ethyl-phenyl boronic acid and 4,6-dichloro-pyrimidin-2-yl-amine provided 4-chloro-6-(5-chloro-2-ethyl-phenyl)-pyrimidin-2-yl-amine as the hydrochloride salt (1.7 g, 45% yield) which upon reaction with 4-trifluoromethyl-phenylamine provided the title compound (66% yield). $^1$H NMR (DMSO-d$_6$) δ 1.10 (t, 3H, J=7.5 Hz, CH$_3$), 2.70 (q, 2H, J=7.5 Hz, CH$_3$), 6.12 (s, 1H, Ar), 6.51 (s, 2H, NH$_2$), 7.31-7.39 (m, 3H, Ar), 7.59 (d, 2H, J=8.6 Hz, Ar), 7.98 (d, 2H, J=8.5 Hz, Ar), 9.60 (s, 1H, NH).

Example 165

6-[5-Bromo-2-(4-chloro-benzyloxy)-phenyl]-N*4*-(4-chloro-phenyl)-pyrimidine-2,4-diamine Following the method described in Example 4, 2-(2-amino-6-chloro-pyrimidin-4-yl)-4-bromo-phenol and 4-chloro-phenylamine provided 2-[2-amino-6-(4-chloro-phenylamino) pyrimidin-4-yl]-4-bromo-phenol (64% yield).

To a stirred suspension of 2-[2-amino-6-(4-chloro-phenylamino) pyrimidin-4-yl]-4-bromo-phenol (0.059 g, 0.15 mmol), 4-chloro-benzylchloride (0.073 g, 0.45 mmol) and cesium carbonate (0.098 g, 0.30 mmol) in acetonitrile (10 ml) was added potassium iodide (40 mg). The mixture was stirred at 80° C. for 2 hours. Filtration and concentration of the filtrate provided a crude product which was purified by preparative TLC eluting with ethyl acetate-hexane (1:3) to provide the title compound (0.02 g, 26% yield). $^1$H NMR (CD$_3$OD) δ 5.23 (s, 1H, CH$_2$), 6.41 (s, 1H, Ar), 7.26 (d, 1H, J=9.6 Hz, Ar), 7.38-7.42 (m, 6H, Ar), 7.71-7.74 (m, 4H, Ar).

Example 166

6-(5-Bromo-2-phenethyloxy-phenyl)-N*4*-(4-chloro-phenyl)-pyrimidine-2,4-diamine

Following the method described in Example 165, 2-(2-amino-6-chloro-pyrimidin-4-yl)-4-bromo-phenol and (2-chloro-ethyl)-benzene provided the title compound (25% yield). $^1$H NMR (CD$_3$OD) δ 3.08 (t, 2H, J=6.2 Hz, CH$_2$), 4.37 (t, 2H, J=6.2 Hz, CH$_2$), 6.27 (s, 1H, Ar), 7.13-7.22 (m, 6H, Ar), 7.43-7.46 (m, 2H, Ar), 7.64 (d, 1H, J—2.5 Hz, Ar), 7.69 (dd, 1H, J=6.4 Hz, J=2.5 Hz, Ar), 7.83 (b, 2H, Ar).

Example 167

6-(5-Chloro-2-ethyl-phenyl)-N*-4*-(4-chloro-phenyl)-pyrimidine-2,4-diamine

Following the method described in Example 4,4-chloro-6-(5-chloro-2-ethyl-phenyl)-pyrimidine-2-ylamine and 4-chloroaniline provided the title compound (33% yield). $^1$H NMR (DMSO-d$_6$) δ 1.12 (t, J=7.5 Hz, CH$_3$), 2.74 (q, J=7.6 Hz, CH$_2$), 6.06 (s, 1H, Ar), 6.43 (br s, NH$_2$), 7.35-7.31 (m, 4H, Ar), 7.41 (dd, J=8.2, 2.3 Hz, 1H, Ar), 7.82 (d, J=8.9 Hz, 2H, Ar), 9.34 (s, NH).

Example 168

6-(5-Chloro-2-cyclohexylmethoxy-phenyl)-N*4*-(4-chloro-phenyl)-pyrimidine-2,4-diamine Following the method described in Example 72, 2-(2-amino-6-chloro-pyrimidin-4-yl)-4-chloro-phenol and bromomethyl-cyclohexane provided 4-chloro-6-(5-chloro-2-cyclohexylmethoxy-phenyl)-pyrimidin-2-ylamine (20% yield).

Following the method described in Example 72, 4-chloro-6-(5-chloro-2-cyclohexylmethoxy-phenyl)-pyrimidin-2-ylamine and 4-chloro-aniline provided the title compound (98% yield). $^1$H NMR (DMSO-d$_6$) δ 1.15-1.19 (m, 4H, CH$_2$) δ 1.65-1.73 (m, 6H, CH$_2$), 3.89 (d, 2H, J=5.7 Hz, Ar), 6.49 (s, 1H, Ar), 7.27 (d, 1H, J=8.4 Hz, Ar), 7.46 (d, 2H, J=8.7 Hz, Ar), 7.61 (d, 2H, J=8.5 Hz, Ar), 7.82-7.85 (m, 2H, Ar).

Example 169

6-(5-Chloro-2-ethyl-phenyl)-N*-4*-(4-nitro-phenyl)-pyrimidine-2,4-diamine

Following the method described in Example 4,4-chloro-6-(5-chloro-2-ethyl-phenyl)-pyrimidine-2-ylamine and 4-nitroaniline provided the title compound (44% yield). $^1$H NMR (DMSO-d$_6$) δ 1.13 (t, J=7.5 Hz, CH$_3$), 2.75 (q, J=7.5 Hz, CH$_2$), 6.20 (s, 1H, Ar), 6.66 (br s, NH$_2$), 7.43-7.35 (m, 3H, Ar), 8.19 (dd, J=42.8, 9.4 Hz, 4H, Ar), 9.98 (s, NH).

Example 170

3-[2-Amino-6-(2,5-dichloro-phenyl)-pyrimidin-4-ylamino]-benzoic acid ethyl ester Following the method described in Example 4, the hydrochloride salt of 4-chloro-6-(2,5-dichloro-phenyl)-pyrimidin-2-ylamine and 3-amino-ethyl-benzoate provided the title compound as the hydrochloride salt (93% yield). $^1$H NMR (DMSO-d$_6$) δ 1.33 (t, 3H, J=7.1 Hz, CH$_3$), 4.32 (q, 2H, J=7.1 Hz, CH$_2$), 6.32 (s, 1H, Ar), 6.50 (s, 2H, NH$_2$), 7.44 (t, 1H, J=7.9 Hz, Ar), 7.50-7.60 (m, 3H, Ar), 7.63-7.64 (m, 1H, Ar), 8.02-8.03 (m, 1H, Ar), 8.36-8.38 (m, 1H, Ar), 9.55 (s, 1H, NH).

Example 171

3-[2-Amino-6-(5-bromo-2-methoxy-phenyl)-pyrimidin4-ylamino]-benzoic acid ethyl ester Following the method described in Example 4,4-chloro-6-(5-bromo-2-methoxy-phenyl)-pyrimidin-2-ylamine and 3-amino-ethyl-benzoate provided the title compound (0.052 g, 74% yield). $^1$H NMR (DMSO-$d_6$) δ 1.34 (t, 3H, J=7.1 Hz, Ar), 3.88 (s, 3H, CH$_3$), 4.32 (q, 2H, J=7.1 Hz, CH$_2$), 6.34 (s, 2H, NH$_2$), 6.77 (s, 1H, Ar), 7.12 (d, 1H, J=8.9 Hz, Ar), 7.42 (t, 1H, J=7.8 Hz, Ar), 7.52-7.58 (m, 2H, Ar), 8.05-8.07 (m, 2H, Ar), 8.38 (d, 1H, J=8.2 Hz, Ar), 9.47 (s, 1H, NH).

Example 172

(4-Bromo-phenyl)-[6-(5-chloro-2-methyl-phenyl)-pyrimidin-4-yl]-amine

Following the method described in Example 4,5-chloro-2-methyl-phenyl boronic acid and 4,6-dichloro-pyrimidine provided 4-chloro-6-(5-chloro-2-methyl-phenyl)-pyrimidine (1.2 g, 50% yield) which upon reaction with 4-bromo-aniline provided the title compound (25% yield). $^1$H NMR (DMSO-$d_6$) δ 2.37 (s, 3H, CH$_3$), 6.91 (s, 1H, Ar), 7.37 (d, 1H, J=8.2 Hz, Ar), 7.44 (d, 1H, J=8.2 Hz, Ar), 7.50-7.54 (m, 3H, Ar), 7.72 (d, 2H, J=8.8 Hz, Ar), 8.74 (s, 1H, Ar), 9.84 (s, 1H, NH).

Example 173

4-[2-Amino 6-(5-bromo-2-methyl-phenyl)-pyrimidin-4-ylamino]-phenyl-boronic acid

Following the method described in Example 4,4-chloro-6-(5-chloro-2-methyl-phenyl)-pyrimidin-2-yl-amine and 4-amino-phenyl-boronic acid provided the title compound (36% yield) as its hydrochloride salt. $^1$H NMR (CD$_3$OD) δ 2.41 (s, 3H, CH$_3$), 6.31 (s, 1H, Ar), 7.43 (d, 2H, J=8.6 Hz, Ar), 7.50-7.53 (m, 3H, Ar), 7.70 (d, 2H, J=8.4 Hz, Ar).

Example 174

6-(2-Allyloxy-5-chloro-phenyl)-N*4*-(4-chloro-phenyl)-pyrimidine-2,4-diamine

Following the method described in Example 72, 4-chloro-6-(5-chloro-2-ethoxy-phenyl)-pyrimidin-2-ylamine provided 2-(2-amino-6-chloro-pyrimidin-4-yl)-4-chloro-phenol (71% yield).
Following the method described in Example 4, 2-(2-amino-6-chloro-pyrimidin-4yl)-4-chloro-phenol and 4-chloro-aniline provided 2-[2-amino-6-(4-chloro-phenylamino)-pyrimidin-4-yl]-4-chloro-phenol (87% yield).
Following the method described in Example 165, 2-[2-amino-6-(4-chloro-phenylamino)-pyrimidin-4-yl]-4-chloro-phenol and 3-bromo-propene provided the title compound (80% yield) $^1$H NMR (DMSO-$d_6$) δ 4.68 (d, 2H, CH$_2$), 5.25-5.28 (m, 1H, Ar), 5.36-5.41 (m, 1H, Ar), 6.03-6.08 (m, 1H, Ar), 6.36 (s, 2H, NH$_2$), 6.70 (s, 1H, Ar), 7.14 (d, 1H, J=8.9 Hz, Ar), 7.31 (d, 2H, J=8.9 Hz, Ar), 7.40 (dd, 1H, J—2.8 Hz, J=8.8 Hz, Ar), 7.78 (d, 2H, J=8.9 Hz, Ar), 7.85 (d, 1H, J=2.8 Hz, Ar), 9.32 (s, 1H, NH).

Example 175

2-{4-[2-amino-6-(5-chloro-2-ethyl-phenyl)-pyrimidin4-ylamino]-phenyl}-ethanol

Following the method described in Example 4,4-chloro-6-(5-chloro-2-ethyl-phenyl)-pyrimidin-2-ylamine and 4-aminophenethyl alcohol provided the title compound (19% yield). $^1$H NMR (DMSO-$d_6$) δ 1.12 (t, J=7.5 Hz, CH$_3$), 2.74-2.66 (m, 4H, CH$_2$), 3.61-3.56 (m, CH$_2$), 4.63 (t, J=5.2 Hz, OH), 6.03 (s, 1H, Ar), 6.32 (br s, NH$_2$), 7.14 (d, J=8.4 Hz, 2H, Ar), 7.41-7.31 (m, 3H, Ar), 7.62 (d, J=8.4 Hz, 2H, Ar), 9.11 (br s, NH).

Example 176

2-{4-[6-(5-Chloro-2-methyl-phenyl)-pyrimidin-4-ylamino]-phenyl}-ethanol

Following the method described in Example 4,5-chloro-2-methyl-phenyl boronic acid and 4,6-dichloro-pyrimidine provided 4-chloro-6-(5-chloro-2-methyl-phenyl)-pyrimidine (1.2 g, 50% yield) which upon reaction with 2-(4-amino-phenyl)-ethanol provided the title compound (51% yield). $^1$H NMR (DMSO-$d_6$) δ 2.34 (s, 3H, CH$_3$), 2.68 (t, 2H, J=7.1 Hz, CH$_2$), 3.58 (m, 2H, CH$_2$), 4.61 (t, 1H, J=5.1 Hz, OH), 6.83 (s, 1H, Ar), 7.17 (d, 2H, J=8.4 Hz, Ar), 7.34 (m, 1H, Ar), 7.41 (m, 1H, Ar), 7.47 (s, 1H, Ar), 7.56 (d, 2H, J=8.4 Hz, Ar), 8.65 (s, 1H, Ar), 9.60 (s, 1H, NH).

Example 177

6-(2-Benzyloxy-5-bromo-phenyl)-N*4*-(4-nitro-phenyl)-pyrimidine-2,4-diamine

Following the method described in Example 4,4-(2-benzyloxy-5-bromo-phenyl)-6-chloro-pyrimidin-2-ylamine and 4-nitro-phenylamine provided the title compound (76% yield) as its hydrochloride salt. $^1$H NMR (DMSO-$d_6$) δ 5.27 (s, 2H, CH$_2$), 6.66 (s, 1H, Ar), 7.28-7.46 (m, 6H, Ar), 7.75-7.79 (m, 2H, Ar), 8.09-8.11 (m, 2H, Ar), 8.24 (d, 2H, J=9.2 Hz, Ar).

Example 178

6-[5-Bromo-2-(4-nitro-benzyloxy)-phenyl]-N*4*-(4-chloro-phenyl)-pyrimidine-2,4-diamine A stirred suspension of 2-(2-amino-6-chloro-pyrimidin-4-yl)-4-bromo-phenol (0.151 g, 0.50 mmol), 1-bromomethyl-4-nitro-benzene (0.218 g, 1.0 mmol), and cesium carbonate (0.325 g, 1.0 mmol) in acetonitrile (10 ml) was stirred at 80° C. for 2 hours. Filtration and concentration of the filtrate provided a crude product which was dissolved in ethyl acetate (10 ml) and stirred while a 4 M solution of hydrogen chloride in dioxane (0.50 ml, 2.0 mmol) was added. Filtration provided 6-[5-bromo-2-(4-nitro-benzyloxy)-phenyl]-6-chloro-pyrimidin-2-ylamine as hydrochloride salt (0.23 g, 96% yield).
Following the method described in Example 4, 6-[5-bromo-2-(4-nitro-benzyloxy)-phenyl]-6-chloro-pyrimidin-2-ylamine and 4-chloro-phenylamine provided the title compound (82% yield) as its hydrochloride salt. $^1$H NMR (DMSO-$d_6$) δ 5.42 (s, 2H, CH$_2$), 6.55 (s, 1H, Ar), 7.29 (d, 1H, J=9.4 Hz, Ar), 7.45 (d, 2H, J=8.8 Hz, Ar), 7.72-7.84 (m, 6H, Ar), 8.24 (d, 2H, J=8.7 Hz, Ar).

Example 179

N*4*-(4-Chloro-3-trifluoromethyl-phenyl)-6-(2,5-dichloro-phenyl)-pyrimidin-2,4-diamine Following the method described in Example 4, the hydrochloride salt of 4-chloro-6-(2,5-dichloro-phenyl)-pyrimidin-2-ylamine and 4-chloro-3-trifluoromethyl-phenylamine provided the title compound as the hydrochloride salt (0.031 g, 30% yield).

$^1$H NMR (DMSO-d$_6$) δ 6.47 (s, 1H, Ar), 7.71-7.73 (m, 3H, Ar), 7.79 (s, 1H, Ar), 8.14 (s, 1H, Ar), 8.25 (m, 1H, Ar).

Example 180

[6-(5-Bromo-2-ethoxy-phenyl)-pyrimidin-4-yl]-(4-trifluoromethyl-phenyl)-amine

Following the method described in Example 4, 5-bromo-2-ethoxy-phenyl boronic acid and 4,6-dichloro-pyrimidine provided 4-chloro-6-(5-bromo-2-ethoxy-phenyl)-pyrimidine (1.1 g, 39% yield) which upon reaction with 4-trifluoromethyl-phenylamine provided the title compound (80% yield). $^1$H NMR (DMSO-d$_6$) δ 1.41 (t, 3H, J=7.0 Hz, CH$_3$), 4.20 (q, 2H, J=7.0 Hz, CH$_2$), 7.19 (d, 1H, J=8.9 Hz, Ar), 7.60-7.61 (m, 2H, Ar), 7.71 (d, 2H, J=8.7 Hz, Ar), 8.11 (s, 1H, Ar), 8.79 (s, 1H, Ar), 10.07 (s, 1H, NH).

Example 181

[6-(5-Bromo-2-ethoxy-phenyl)-pyrimidin-4-yl]-(4-bromo-phenyl)-amine

Following the method described in Example 4, 5-bromo-2-ethoxy-phenyl boronic acid and 4,6-dichloro-pyrimidine provided 4-chloro-6-(5-bromo-2-ethoxy-phenyl)-pyrimidine (1.1 g, 39% yield) which upon reaction with 4-bromo-aniline provided the title compound (45% yield). $^1$H NMR (DMSO-d$_6$) δ 1.40 (t, 3H, J=6.9 Hz, CH$_3$), 4.18 (q, 2H, J=7.0 Hz, CH$_2$), 7.16 (d, 1H, J=8.9 Hz, Ar), 7.52-7.54 (m, 3H, Ar), 7.60 (m, 2H, Ar), 7.69 (d, 2H, J=8.8 Hz, Ar) 8.11 (s, 1H, Ar), 8.72 (s, 1H, Ar), 9.80 (s, 1H, NH).

Example 182

6-[5-Bromo-2-(2-methoxy-benzyloxy)-phenyl]-N*4*-(4-chloro-phenyl)-pyrimidine-2,4-diamine Following the method described in Example 178, 6-[5-bromo-2-(2-methoxy-benzyloxy)-phenyl]-6-chloro-pyrimidin-2-ylamine and 4-chloro-phenylamine provided the title compound (57% yield). $^1$H NMR (CD$_3$OD) δ 3.82 (s, 3H, CH$_3$), 5.25 (s, 2H, CH$_2$), 6.35 (s, 1H, Ar), 6.89-6.98 (m, 2H, Ar), 7.21-7.48 (m, 3H, Ar), 7.38-7.42 (m, 2H, Ar), 7.69-7.82 (m, 4H, Ar).

Example 183

4-[2-Amino-6-(5-bromo-2-ethoxy-phenyl)-pyrimidin-4-ylamino]-N-hydroxy-benzamide

To a stirred solution of 4-[2-amino-6-(5-bromo-2-ethoxy-phenyl)-pyrimidin-4-ylamino]-benzoic acid (0.086 g, 0.20 mmol) in dimethylformamide (3.0 ml) was added benzotriazol-1-ol (0.054 g, 0.40 mmol) followed by 1-(3-dimethylaminopropyl)-3-ethylcarbodiimide hydrochloride (0.086 g, 0.44 mmol). After stirring at room temperature for 1 hour, hydroxylamine hydrochloride (0.070 g, 1.0 mmol) was added followed by triethylamine (0.1 g, 1.0 mmol). After stirring for 16 hours, the solvent was evaporated under reduced pressure and the residue was treated with 1 M aqueous sodium carbonate solution (10 ml). Filtration provided the title compound (0.065 g, 73% yield) as a light brown solid. $^1$H NMR (DMSO-d$_6$) δ 1.38 (t, 3H, J=6.9 Hz, CH$_3$), 4.12 (q, 2H, J=6.9 Hz, CH$_2$), 6.32 (s, 2H, NH$_2$), 6.79 (s, 1H, Ar), 7.08 (d, 1H, J=8.9 Hz, Ar), 7.52 (dd, 1H, J=8.9 Hz, J=2.6 Hz, Ar), 7.66 (b, 4H, Ar), 8.04 (d, 1H, J=2.6 Hz, Ar), 9.24 (s, 1H, NH).

Example 184

5-[2-Amino-6-(5-bromo-2-methoxy-phenyl)-pyrimidin4-ylamino]-2-chloro-N-methyl-benzamide Following the method described in Example 4, 4-chloro-6-(5-bromo-2-methoxy-phenyl)-pyrimidin-2-yl-amine and 5-amino-2-chloro-N-methyl-benzamide provided the title compound (62% yield) as its hydrochloride salt. $^1$H NMR (DMSO-d$_6$) δ 2.78 (d, 1H, J=4.6 Hz, CH$_3$), 3.89 (s, 3H, CH$_3$), 6.63 (s, 1H, Ar), 7.24 (d, 1H, J—9.4 Hz, Ar), 7.49 (d, 11H, J=8.8 Hz, Ar), 7.75-7.78 (m, 3H, Ar), 7.93 (b, 1H, Ar), 8.39 (q, 1H, J=4.6 Hz, NH), 10.97 (s, 1H), 12.61 (s, 1H).

Example 185

6-[5-Bromo-2-(4-methoxy-benzyloxy)-phenyl]-N*4*-(4-chloro-phenyl)-pyrimidine-2,4-diamine Following the method described in Example 165, 2-[2-amino-6-(4-chloro-phenylamino) pyrimidin-4-yl]-4-bromo-phenol and 4-methoxy-benzyl chloride provided the title compound (50% yield). $^1$H NMR (CD$_3$OD) δ 3.76 (s, 3H, CH$_3$), 5.16 (s, 2H, CH$_2$), 6.37 (s, 1H, Ar), 6.89-6.92 (m, 2H, Ar), 7.28-7.30 (m, 3H, Ar), 7.39-7.42 (m, 2H, Ar), 7.69-7.32 (m, 4H, Ar).

Example 186

4-[2-Amino-6-(5-bromo-2-ethoxy-phenyl)-pyrimidin4-ylamino]-benzamide

Following the method described in Example 4, 4-chloro-6-(5-bromo-2-ethoxy-phenyl)-pyrimidin-2-yl-amine and 4-amino-benzamide provided the title compound (77% yield) as its hydrochloride salt. $^1$H NMR (DMSO-d$_6$) δ 1.37 (t, 3H, J=6.9 Hz, CH$_3$), 4.16 (q, 2H, J=6.9 Hz, CH$_2$), 6.64 (s, 1H, Ar), 7.22 (d, 1H, J=8.9 Hz, Ar), 7.35 (s, 1H), 7.27-7.76 (m, 2H, Ar), 7.90-7.96 (m, 4H, Ar).

Example 187

6-(5-Bromo-2-chloro-phenyl)-N*4*-(4-chloro-phenyl)-pyrimidine-2,4-diamine

To a stirred suspension of copper (II) chloride (1.62 g, 12.0 mmol) and tert-butyl nitrite (15.0 mmol) in acetonitrile (40 ml), heated at 60° C., was added a solution of 4-bromo-2-iodo-phenylamine (2.98 g, 10.0 mmol) in acetonitrile (10 ml) dropwise over 50 minutes. After stirring at 60° C. for 1 hour, the mixture was poured into 20% hydrochloric acid (200 ml) and extracted with ether (2×30 ml). The crude product was purified by flash chromatography on silica gel eluting with hexane to provide 4-bromo-1-chloro-2-iodo-benzene (2.4 g, 76% yield).

Following the method described in Example 81, 4-bromo-1-chloro-2-iodo-benzene, isopropylmagnesium chloride and trimethylborate provided 5-bromo-2-chloro-phenylboronic acid (36% yield).

Following the method described in Example 4, 5-bromo-2-chloro-phenylboronic acid and 4,6-dichloro-pyrimidin-2-yl-amine provided 4-chloro-6-(5-bromo-2-chloro-phenyl)-pyrimidin-2-yl-amine (21% yield).

Following the method described in Example 4, 4-chloro-6-(5-bromo-2-chloro-phenyl)-pyrimidin-2-yl-amine and 4-chloro-phenylamine provided the title compound (50% yield). $^1$H NMR (DMSO-d$_6$) δ 6.30 (s, 1H, Ar), 6.52 (s, 2H, NH$_2$), 7.30-7.33 (m, 2H, Ar), 7.51 (d, 1H, J=8.6 Hz, Ar), 7.63 (dd, 1H, J=8.6 Hz, J=2.5 Hz, Ar), 7.77 (d, 1H, J=2.5 Hz, Ar), 7.79-7.82 (m, 2H, Ar).

Example 188

6-[5-Bromo-2-(2-methoxy-benzyloxy)-phenyl]-N*4*-p-tolyl-pyrimidine-2,4-diamine

Following the method described in Example 4, 6-[5-bromo-2-(2-methoxy-benzyloxy)-phenyl]-6-chloro-pyrimidin-2-ylamine and 4-methyl-phenylamine provided the title compound (36% yield). $^1$H NMR (CD$_3$OD) δ 3.82 (s, 3H, CH$_3$), 5.25 (s, 2H, CH$_2$), 6.32 (s, 1H, Ar), 6.89-6.98 (m, 2H, Ar), 7.21-7.30 (m, 6H, Ar), 7.59-7.72 (m, 3H, Ar).

Example 189

6-(5-Bromo-2-chloro-phenyl)-N*4*-(4-trifluoromethyl-phenyl)-pyrimidine-2,4-diamine Following the method described in Example 4, 4-chloro-6-(5-bromo-2-chloro-phenyl)-pyrimidin-2-yl-amine and 4-trifluoro-phenylamine provided the title compound (34% yield). $^1$H NMR (DMSO-d$_6$) δ 6.38 (s, 1H, Ar), 6.62 (s, 2H, NH$_2$), 7.52 (d, 1H, J=8.6 Hz, Ar), 7.60-7.66 (m, 3H, Ar), 7.77 (d, 1H, J=2.5 Hz, Ar), 7.99 (d, 2H, J=8.6 Hz, Ar), 9.71 (s, 1H, NH).

Example 190

[6-(5-Bromo-2-ethoxy-phenyl)-pyrimidin4-yl]-(4-chloro-phenyl)-amine

Following the method described in Example 4, 5-bromo-2-ethoxy-phenyl boronic acid and 4,6-dichloro-pyrimidine provided 4-chloro-6-(5-bromo-2-ethoxy-phenyl)-pyrimidine (39% yield).

Following the method described in Example 4, 4-chloro-6-(5-bromo-2-ethoxy-phenyl)-pyrimidine and 4-chloro-phenylamine provided the title compound (62% yield). $^1$H NMR (DMSO-d$_6$) δ 1.40 (t, 3H, J=6.9 Hz, CH$_3$), 4.18 (q, 2H, J=7.0 Hz, CH$_2$), 7.16 (d, 1H, J=8.9 Hz, Ar), 7.40 (d, 2H, J=8.8 Hz, Ar), 7.51 (s, 1H, Ar), 7.59-7.62 (m, 1H, Ar), 7.74 (d, 2H, J=8.9 Hz, Ar), 8.10 (s, 1H, Ar), 8.72 (s, 1H, Ar), 9.82 (s, 1H, NH).

Example 191

2-{4-[6-(5-Bromo-2-ethoxy-phenyl)-pyrimidin-4-ylamino]-phenyl}-ethanol

Following the method described in Example 4, 4-chloro-6-(5-bromo-2-ethoxy-phenyl)-pyrimidine and 2-(4-amino-phenyl)-ethanol provided the title compound (11% yield). $^1$H NMR (DMSO-d$_6$) δ 1.37 (t, 3H, J=6.9 Hz, CH$_3$), 2.27 (t, 3H, J=7.1 Hz, CH$_3$), 3.60 (m, 2H, CH$_2$), 4.15 (q, 2H, J=7.0 Hz, CH$_2$), 4.64 (t, 1H, J=5.2 Hz, OH), 7.14 (d, 1H, J=8.9 Hz, Ar), 7.20 (d, 2H, J=8.4 Hz, Ar), 7.48 (s, H, Ar), 7.52 (m, 2H, Ar), 7.58-7.61 (m, 1H, Ar), 8.11 (s, 1H, Ar), 8.66 (s, 1H, Ar), 9.60 (s, 1H, NH).

Example 192

[6-(5-Bromo-2-ethoxy-phenyl)-pyrimidin4-yl]-(4-fluoro-phenyl)-amine

Following the method described in Example 4, 4-chloro-6-(5-bromo-2-ethoxy-phenyl)-pyrimidine and 4-fluoro-aniline provided the title compound (18% yield).

$^1$H NMR (DMSO-d$_6$) δ 1.35 (t, 3H, J=6.9 Hz, CH$_3$), 4.14 (q, 2H, J=7.0 Hz, CH$_2$), 7.12-7.21 (m, 3H, Ar), 7.45 (s, 1H, Ar), 7.57-7.59 (m, 1H, Ar), 7.64-7.67 (m, 2H, Ar), 8.10 (s, 1H, Ar), 8.66 (s, 1H, Ar), 9.65 (s, 1H, NH).

Example 193

LPAAT-β Assay

A. Production of Recombinant LPAAT-β for Assays

For the construction of Baculovirus expression vectors, the full-length human LPAAT-β cDNA was amplified by PCR from the DNA template pCE9.LPAAT-β (West et al., *DNA Cell Bid.* 16.691-701 (1997)) using the primers 5'-TGATATCCGA AGAAGATCTT ATGGAGCTGT GGC-CGTCTC-3' (olpb1F; SEQ ID NO:1) and 5'-CAGGCTCTAG ACTACTGGGC CGGCTGCAC-3' (olpb1R; SEQ ID NO:2). The ~870 bp fragment generated was reamplified by PCR using the primers 5' CCTACGTCG ACATGGAACA AAAATTGATA TCCGAAGAAG ATC-3' (olpb2F; SEQ ID NO:3) and 5'-CAGGCTCTAG ACTACTGGGC CGGCTG-CAC-3' (olpb1R; SEQ ID NO:2). The ~890 bp fragment generated was then cleaved with Sal I and Xba I for insertion into pFastBac™ HTc vector (Life Technologies, Gaithersberg, M.d.) between the Sal I and Xba I sites for the generation of the plasmid pFB.LPAAT-β. This plasmid was then transformed into *E. coli* DH10Bac™ (Life Technologies, Gaithersberg, M.d.) for the generation of recombinant Bacmid DNA for transfection in HighFive (Invitrogen, San Diego, Calif.) or SF9 insect cells for the production of recombinant Baculovirus stocks using the protocol described in the Bac-to-Bac® Baculovirus Expression System (Life Technologies, Gaithersberg, M.d.), a eukaryotic expression system for generating recombinant baculovirus through site-specific transposition in *E. coli*. Viral stocks harvested from the transfected cells can then be used to infect fresh insect cells for the subsequence expression of LPAAT-β fusion protein with a poly-histidine tag and a myc-epitope near its N-terminus. The membrane fraction from these Sf9 cells would be the source of LPAAT enzyme.

B. Preparation of Cell Membranes from SJ9 Cells

For the preparation of membranes from Sf9 Cells, all steps are performed on ice or at 4° C. Sf9 cell pellets (~10$^8$ cells) were thawed and resuspended in 1-2 ml of buffer A (20 mM Hepes, pH 7.5, 1 mM DTT, 1 mM EDTA, 20% w/v glycerol, 1 mM Benzamidine, 1 μg/ml soybean trypsin inhibitor (SBTI), 1 μug/ml pepstatin A) w/o DTT but with 1 mM Pefabloc. The cells were lysed by sonication using a Branson Sonifier at output=2, duty cycle=2, 10 pulses each at 10 s. with the tip of small sonicator probe submerged but not touching the walls. DTT was then added to 1 mM from a 1 M stock. The samples were centrifuged at 1500 rpm for 5 min. The low speed supernatant was saved and centrifuged (TLA 100.3 rotor, polycarbonate tubes, 2 ml/tube or 1.5 ml/tube minimum) at 100000×g for 1 hr. The high speed pellet was resuspend in Buffer A with a probe sonicator (10 pulses @ output #2 and duty cycle 20%) as a source of LPAAT enzyme.

C. Assay of LPAAT-β Activity

LPAAT-β catalyzes the transfer of an acyl group from a donor such as acyl-CoA to LPA. The transfer of the acyl group from acyl-CoA to LPA leads to the release of free CoA, which can be reacted with the thiol reagent, 5,5'-dithiobis(2-nitrobenzoic acid) (DTNB). The reaction between DTNB and the free sulfhydryl group from CoA generates a yellow-colored product, 3-carboxylato-4-nitrothiophenolate (CNP), that absorbs at 413 nm. LPAAT-β derived from Sf9 cell membrane overexpressing LPAAT-β were resuspended in HEPES saline buffer (20 mM HEPES pH 7.5, 150 mM NaCl), 1 mg/ml BSA and 72 µl aliquots were distributed into 96-well microtiter plates. 8 µl of compound of interest at 200 µM dissolved in 100% DMSO was added into each well. 20 g of 1 mM 18:1-CoA and 1 mM sn-1-18:1 lysoPA was then added to each well to initiate the reaction and allowed to run at room temperature for 25 min. 100 µl of 1 mM DTNB in 100% ethanol was then added to each well to quench the reaction and for color development. The absorbance at 405 nm, measured using a spectrophotometer plate reader, is proportional to the activity of LPAAT-2 in the sample. This colorimetric assay was used for the high throughput screening of LPAAT inhibitors. Compounds that showed >50% inhibition of the change in absorbance at 405 nm compared to control were selected for a secondary assay.

A secondary assay for LPAAT activity in cell extracts based on either the conversion of fluorescent NBD-LPA to NBD-PA (West, et al., *DNA Cell Biol.* 6:691-701, 1997) or [$^{14}$C]LPA to [$^{14}$C]PA using TLC analysis was used to screen compounds that showed >50% inhibition of LPAAT activity in the primary colorimetric assay. The radiometric assay was carried out in Sf9 cell membrane overexpressing LPAAT-β resuspended in HEPES-saline buffer, pH 7.5, 1 mg/ml BSA, 1 mM EDTA and 200 µM [$^{14}$C]18:1-CoA and 200 µM sn-1-18:1 lysoPA. The samples were incubated 7 min at 37° C., extracted into organic solvent ($CHCl_3/CH_3OH/HCl$ at 33/66/1), before loading onto TLC plates. A more detailed protocol for the radiometric assay is described below:

Specifically, this LPAAT assay is a modification of the acyltransferase assay published previously (Hollenback and Glomset, *Biochemistry* 37:363-376 (1999)).

1. The basic assay, in a total volume of 50 µl, employs a solution of substrates and the protein sample. Total assay volume, as well as the volume of each solution, can be changed to fit an experiment. In addition, other compounds, ex inhibitors and activators, can be included in the assay as well.

2. To prepare the solution of substrates:

a. Stocks of Hepes (pH 7.5), NaCl, EDTA, BSA and acyl-CoA (from Serdery or Sigma) are mixed with water to make the appropriate concentration of each compound. This can be varied from assay-to-assay, but the final reaction mix is about 50 mM Hepes, 100 mM NaCl, 1 mM EDTA, 1 mg/ml BSA and 0-400 µM acyl-CoA.

b. The lysoPA (from Avanti) is typically stored in chloroform and the $^{14}$C-labeled acyl-CoA (from Amersham) is typically stored in water/ethanol=1:1. Appropriate amounts of each solution are added the to a 12×75 mm borosilicate glass test tube and dry the solvent under $N_2$ or Ar. An appropriate volume of the solution prepared in 2a is added to the lysoPA and $^{14}$C-labeled acyl-CoA. The lipids are resuspend by sonication for 15 sec in a bath sonicator. The resulting suspension is then incubated (with occasional gentle vortexing) for about 10 minutes at room temp. The sn-1-16:0 lysoPA may require brief warming of the solvent to solubilize it. The concentration of lysoPA and $^{14}$C-labeled acyl-CoA can vary, but typically the final lysoPA concentration ranges between 0 and 400 µM and the $^{14}$C-labeled acyl-CoA specific activity ranges between 0.5 and 2 Ci/mol.

3. Protein sample: varies from experiment-to-experiment.

4. The assay is performed by mixing the components in 12×75 mm borosilicate glass test tubes (the order of addition does not matter unless indicated) and incubating at 37° C. for 5 to 10 minutes such that the assay within the linear range for time and protein.

5. The reaction is quenched by adding 1.3 ml of chloroform/methanol/HCl=48/51/0.7 and vortexing. 10 µl of carrier solution is then added (3 mg/ml each PA, ex. 16:0-18:1, and lysoPA, ex sn-1-18:1, in chloroform). Two phases are formed by adding 0.3 ml of water to each tube and vortexing.

6. The sample is centrifuged for 3 minutes at 1000×g, the upper (aqueous/methanol) phase is aspirated and the lower phase is dried under nitrogen.

7. Thin layer chromatography:

a. The dried samples are resuspended in 50 µl of chloroform and a 15 µl aliquot is immediately spotted on an Analtech silica gel 60 HP-TLC plate (10×20 cm).

b. Plates are developed in chloroform/methanol/acetic acid/water=85/12.5/12.5/3 (takes about 15 min) and dried.

c. To be able to convert pixel volume (determined by the Storm phosphor imager, see step 8b) into cpm, cpm standard curve must be generated on the plate. $^{14}$C-labeled oleate dilutions in chloroform are made for this purpose. Four stocks (50 cpm/µl to 800 cpm/µl) are made and 2 µl of a different concentration are spotted in each corner of the plate (where previously there was no radioactivity).

d. For quality control purposes, the plates are stained with primuline and scanned with the Storm (blue chemiluminescence mode).

The PA and lysoPA bands are easily detected in this system because of the carrier added in step 5. PA and lysoPA have respective Rf's of about 0.63 and 0.21.

8. Quantitating activity:

a. The plates are then wrapped in saran wrap and exposed to a freshly blanked phosphor screen overnight (longer exposures can also be done to increase the signal).

b. The screens are scanned (Phosphorimager mode), and LPAAT activity is determined by quantifying the pixels in the band comigrating with PA standard versus the standard curve generated from the cpm standards that were spotted in step 7c.

TABLE 1

| | Compound | LPAAT-β cell-free assay (IC$_{50}$, μM) | Compound Name |
|---|---|---|---|
| 1 | | 0.12 | 6-(5-Chloro-2-methoxy-phenyl)-N*4*-p-tolyl-pyrimidine-2,4-diamine |
| 2 | | 0.054 | 6-(5-Chloro-2-methoxy-phenyl)-N*4*-(4-chloro-phenyl)-pyrimidine-2,4-diamine |
| 3 | | 0.08 | 6-(5-Chloro-2-methoxy-phenyl)-N*4*-(1H-indazol-6-yl)-pyrimidine-2,4-diamine |
| 4 | | 0.088 | 6-(5-Chloro-2-methoxy-phenyl)-N*4*-(4-trifluoromethylphenyl)-pyrimidine-2,4-diamine |
| 5 | | 0.029 | N*4*-(4-Bromo-phenyl)-6-(5-chloro-2-methoxy-phenyl)-pyrimidine-2,4-diamine |

TABLE 1-continued

| Compound | | LPAAT-β cell-free assay (IC$_{50}$, μM) | Compound Name |
|---|---|---|---|
| 6 | 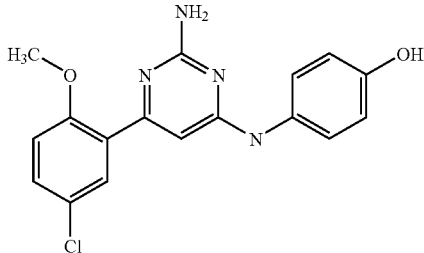 | 0.45 | 4-[2-Amino-6-(5-chloro-2-methoxy-phenyl)-pyrimidin-4-ylamino]-phenol |
| 7 | 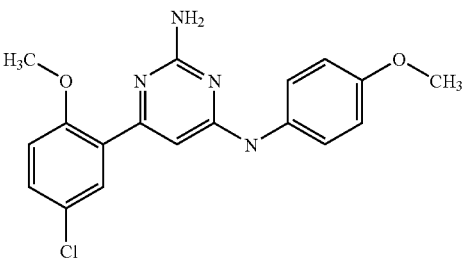 | 0.41 | 6-(5-Chloro-2-methoxy-phenyl)-N*4*-(4-methoxy-phenyl)-pyrimidine-2,4-diamine |
| 8 | 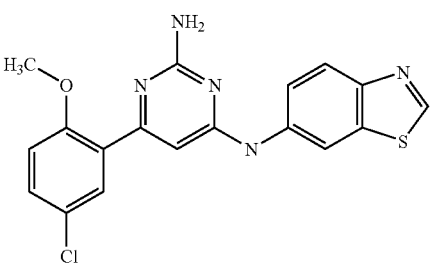 | 0.27 | N*4*-Benzothiazol-6-yl-6-(5-chloro-2-methoxy-phenyl)-pyrimidine-2,4-diamine |
| 9 | 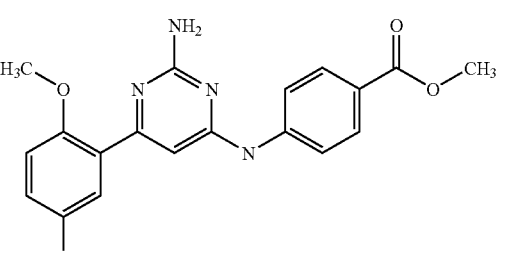 | 0.6 | 4-[2-Amino-6-(5-chloro-2-methoxy-phenyl)-pyrimidin-4-ylamino]-benzoic acid methyl ester |
| 10 | 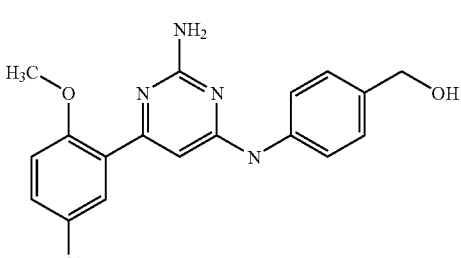 | 0.12 | {4-[2-Amino-6-(5-chloro-2-methoxy-phenyl)-pyrimidin-4-ylamino]-phenyl}-methanol |

TABLE 1-continued
| Compound | | LPAAT-β cell-free assay (IC$_{50}$, μM) | Compound Name |
|---|---|---|---|
| 11 | 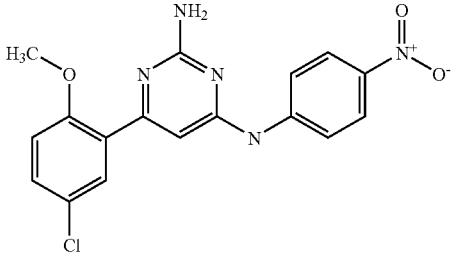 | 0.014 | 6-(5-Chloro-2-methoxy-phenyl)-N*4*-(4-nitro-phenyl)-pyrimidine-2,4-diamine |
| 12 | 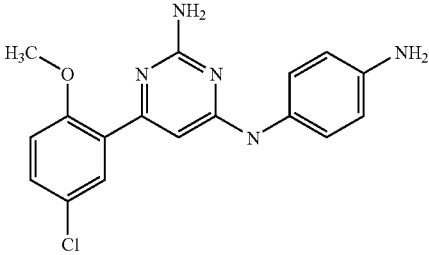 | 0.095 | N*4*-(4-Amino-phenyl)-6-(5-chloro-2-methoxy-phenyl)-pyrimidine-2,4-diamine |
| 13 | 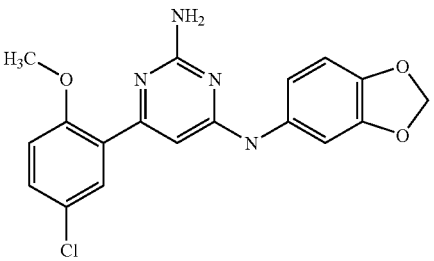 | 0.1 | N*4*-Benzo[1,3]dioxol-5-yl-6-(5-chloro-2-methoxy-phenyl)-pyrimidine-2,4-diamine |
| 14 | 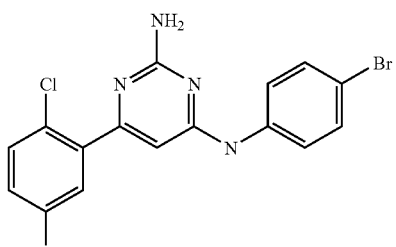 | 0.026 | N*4*-(4-Bromo-phenyl)-6-(2,5-dichloro-phenyl)-pyrimidine-2,4-diamine |
| 15 | 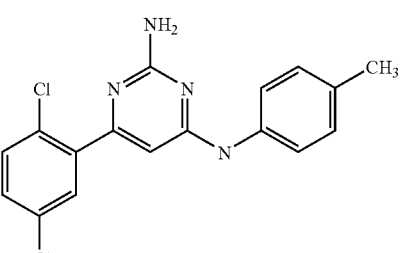 | 0.05 | 6-(2,5-Dichloro-phenyl)-N*4*-p-tolyl-pyrimidine-2,4-diamine |

TABLE 1-continued
| | Compound | LPAAT-β cell-free assay (IC$_{50}$, μM) | Compound Name |
|---|---|---|---|
| 16 | 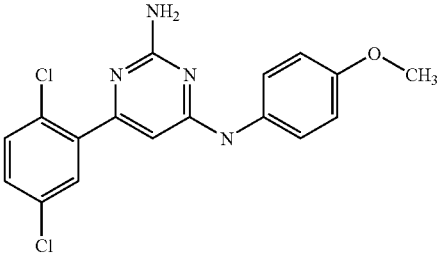 | 0.12 | 6-(2,5-Dichloro-phenyl)-N*4*-(4-methoxy-phenyl)-pyrimidine-2,4-diamine |
| 17 | 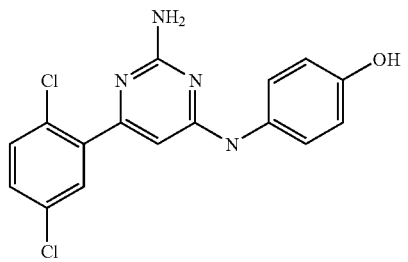 | 0.24 | 4-[2-Amino-6-(2,5-dichloro-phenyl)-pyrimidine-4-ylamino]-phenol |
| 18 | 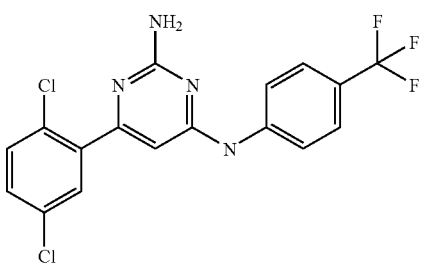 | 0.082 | 6-(2,5-Dichloro-phenyl)-N*4*-(4-trifluoromethyl-phenyl)-pyrimidine-2,4-diamine |
| 19 | 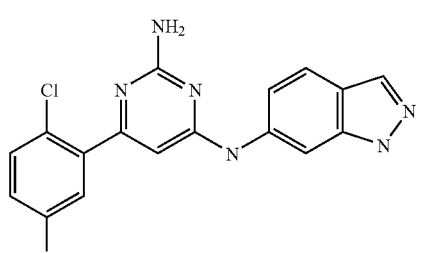 | 0.027 | 6-(2,5-Dichloro-phenyl)-N*4*-(1H-indazol-6-yl)-pyrimidine-2,4-diamine |
| 20 | 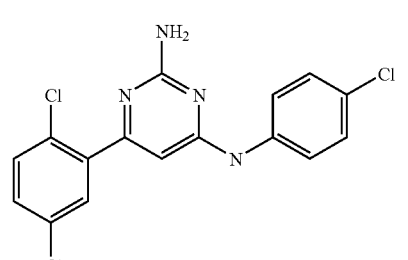 | 0.02 | N*4*-(4-Chloro-phenyl)-6-(2,5-dichloro-phenyl)-pyrimidine-2,4-diamine |

TABLE 1-continued

| Compound | | LPAAT-β cell-free assay (IC$_{50}$, μM) | Compound Name |
|---|---|---|---|
| 21 | (structure) | 0.33 | 4-[2-Amino-6-(2,5-dichloro-phenyl)-pyrimidin-4-yl-amino]-benzoic acid methyl ester |
| 22 | (structure) | 0.06 | {4-[2-Amino-6-(2,5-dichloro-phenyl)-pyrimidin-4-yl-amino]-phenyl}-methanol |
| 23 | (structure) | 0.095 | N*4*-Benzo[1,3]dioxol-5-yl-6-(2,5-dichloro-phenyl)-pyrimidine-2,4-diamine |
| 24 | (structure) | 0.029 | 4-[2-Amino-6-(2,5-dichloro-phenyl)-pyrimidin-4-ylamino]-benzonitrile |
| 25 | (structure) | 0.009 | 6-(2,5-Dichloro-phenyl)-N*4*-(4-nitro-phenyl)-pyrimidine-2,4-diamine |

TABLE 1-continued

| Compound | | LPAAT-β cell-free assay (IC$_{50}$, μM) | Compound Name |
|---|---|---|---|
| 26 | 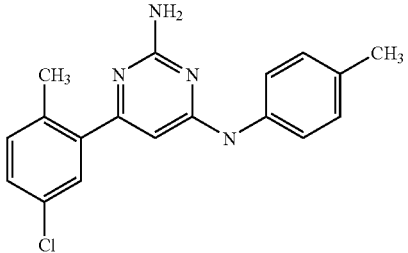 | 0.094 | 6-(5-Chloro-2-methyl-phenyl)-N*4*-p-tolyl-pyrimidine-2,4-diamine |
| 27 | 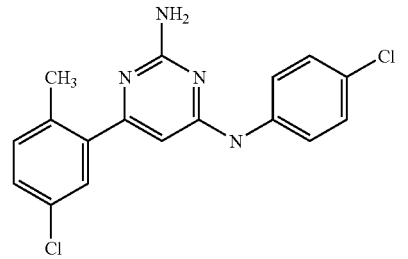 | 0.028 | 6-(5-Chloro-2-methyl-phenyl)-N*4*-(4-chloro-phenyl)-pyrimidine-2,4-diamine |
| 28 | 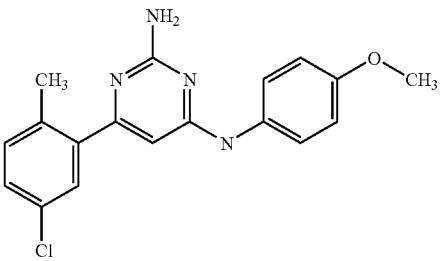 | 0.2 | 6-(5-Chloro-2-methyl-phenyl)-N*4*-(4-methoxy-phenyl)-pyrimidine-2,4-diamine |
| 29 | 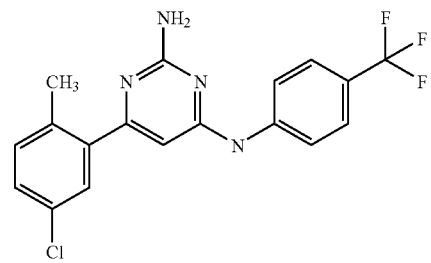 | 0.134 | 6-(5-Chloro-2-methyl-phenyl)-N*4*-(4-trifluoromethyl-phenyl)-pyrimidine-2,4-diamine |
| 30 | 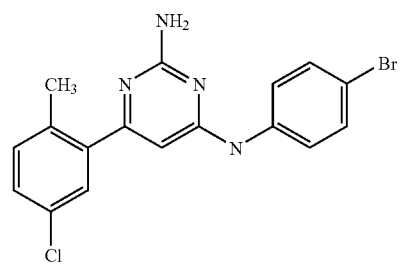 | 0.034 | N*4*-(4-Bromo-phenyl)-6-(5-chloro-2-methyl-phenyl)-pyrimidine-2,4-diamine |

TABLE 1-continued

| | Compound | LPAAT-β cell-free assay (IC$_{50}$, μM) | Compound Name |
|---|---|---|---|
| 31 | | 0.032 | 6-(5-Chloro-2-methyl-phenyl)-N*4*-(1H-indazol-6-yl)-pyrimidine-2,4-diamine |
| 32 | | 0.038 | 4-[2-Amino-6-(5-chloro-2-methyl-phenyl)-pyrimidin-2-ylamino]-benzonitrile |
| 33 | | 0.095 | {4-[2-Amino-6-(5-chloro-2-methyl-phenyl)-pyrimidin-4-ylamino]-phenyl}-methanol |
| 34 | | 2 | 6-(5-Chloro-2-methoxy-phenyl)-N*2*-(4-chloro-phenyl)-pyrimidine-2,4-diamine |
| 35 | | 0.8 | 6-(5-Chloro-2-methoxyphenyl)-N*2*-(1H-indazol-6yl)-pyrimidine-2,4-diamine |

TABLE 1-continued

| Compound | | LPAAT-β cell-free assay (IC$_{50}$, μM) | Compound Name |
|---|---|---|---|
| 36 | [structure] | 8 | N-(4-Bromo-phenyl)-2-(5-chloro-2-methoxy-phenyl)-pyrimidine-4,6-diamine |
| 37 | [structure] | 2.1 | 2-(5-Chloro-2-methoxy-phenyl)-N-(1H-indazol-6-yl)-pyrimidine-4,6-diamine |
| 38 | [structure] | 0.05 | [6-(5-Chloro-2-methoxy-phenyl)-2-methyl-pyrimidin-4-yl]-(4-chloro-phenyl)-amine |
| 39 | [structure] | 0.18 | [6-(5-Chloro-2-methoxy-phenyl)-2-methyl-pyrimidin-4-yl]-(4-bromo-phenyl)-amine |
| 40 | [structure] | 0.014 | [6-(5-Chloro-2-methoxy-phenyl)-2-methyl-pyrimidin-4-yl]-(1H-indazol-6-yl)-amine |

TABLE 1-continued

| Compound | | LPAAT-β cell-free assay (IC$_{50}$, μM) | Compound Name |
|---|---|---|---|
| 41 | (structure) | 0.021 | [6-(5-Chloro-2-methyl-phenyl)-2-methyl-pyrimidin-4-yl]-(4-bromo-phenyl)-amine |
| 42 | (structure) | 0.01 | [6-(5-Chloro-2-methyl-phenyl)-2-methyl-pyrimidin-4-yl]-(4-chloro-phenyl)-amine |
| 43 | (structure) | 0.017 | [6-(5-Chloro-2-methyl-phenyl)-2-methyl-pyrimidin-4-yl]-(1H-indazol-6-yl)-amine |
| 44 | (structure) | 0.075 | {4-[2-Amino-6-(5-chloro-2-ethoxy-phenyl)-pyrimidin-4-ylamino]-phenyl}-methanol |
| 45 | (structure) | 0.033 | 4-[2-Amino-6-(5-chloro-2-methoxy-phenyl)-pyrimidin-4-ylamino]-benzonitrile |

TABLE 1-continued

| | Compound | LPAAT-β cell-free assay (IC$_{50}$, μM) | Compound Name |
|---|---|---|---|
| 46 | | 0.010 | 6-(5-Chloro-2-ethoxy-phenyl)-N*4*-(4-nitro-phenyl)-pyrimidine-2,4-diamine |
| 47 | | 0.028 | 2-{4-[2-Amino-6-(5-chloro-2-ethoxy-phenyl)-pyrimidin-4-ylamino]-phenyl}-ethanol |
| 48 | | 0.028 | 2-{4-[2-Amino-6-(2,5-dichloro-phenyl)-pyrimidin-4-ylamino]-phenyl}-ethanol |
| 49 | | 0.049 | 2-{4-[2-Amino-6-(5-chloro-2-methyl-phenyl)-pyrimidin-4-ylamino]-phenyl}-ethanol |
| 50 | | 0.046 | 2-{4-[2-Amino-6-(5-chloro-2-methoxy-phenyl)-pyrimidin-4-ylamino]-phenyl}-ethanol |

TABLE 1-continued

| | Compound | LPAAT-β cell-free assay (IC$_{50}$, μM) | Compound Name |
|---|---|---|---|
| 51 | | Less active | 6-(5-Chloro-2-methoxy-phenyl)-5-methyl-N*4*-(1H-indazol-6-yl)-pyrimidine-2,4-diamine |
| 52 | | 0.500 | 5-Bromo-6-(5-chloro-2-methoxy-phenyl)-N*4*-(1H-indazol-6-yl)-pyrimidine-2,4-diamine |
| 53 | | 0.095 | 6-(5-Chloro-2-ethoxy-phenyl)-N*4*-p-tolyl-pyrimidine-2,4-diamine |
| 54 | | 0.024 | 6-(5-Chloro-2-ethoxy-phenyl)-N*4*-(1H-indazol-6-yl)-pyrimidine-2,4-diamine |
| 55 | | 0.017 | 6-(5-Chloro-2-ethoxy-phenyl)-N*4*-(4-chloro-phenyl)-pyrimidine-2,4-diamine |

TABLE 1-continued

| | Compound | LPAAT-β cell-free assay (IC$_{50}$, μM) | Compound Name |
|---|---|---|---|
| 56 | | 0.070 | 6-(5-Chloro-2-ethoxy-phenyl)-N*4*-(4-trifluoromethyl-phenyl)-pyrimidine-2,4-diamine |
| 57 | | 0.022 | 4-[2-Amino-6-(5-chloro-2-ethoxy-phenyl)-pyrimidin-4-ylamino]-benzonitrile |
| 58 | | 0.200 | 6-(5-Chloro-2-ethoxy-phenyl)-N*4*-(4-methoxy-phenyl)-pyrimidine-2,4-diamine |
| 59 | | 0.210 | {4-[2-Amino-6-(5-bromo-2-ethoxy-phenyl)-pyrimidin-4-ylamino]-phenyl}-phenyl-methanone |
| 60 | | 0.060 | 6-(5-Bromo-2-ethoxy-phenyl)-N*4*-(4-trifluoromethyl-phenyl)-pyrimidin-2,4-diamine |

TABLE 1-continued

| Compound | | LPAAT-β cell-free assay (IC$_{50}$, μM) | Compound Name |
|---|---|---|---|
| 61 | | 0.350 | 4-[2-Amino-6-(5-bromo-2-ethoxy-phenyl)-pyrimidin-4-ylamino]-benzoic acid methyl ester |
| 62 | | 0.080 | {4-[2-Amino-6-(5-bromo-2-ethoxy-phenyl)-pyrimidin-4-ylamino]-phenyl}-methanol |
| 63 | | 0.083 | Succinic acid mono-{4-[2-amino-6-(5-chloro-2-ethoxy-phenyl)-pyrimidin-4-ylamino]-benzyl}-ester |
| 64 | | 1.500 | Amino acetic acid-4-[2-amino-6-(5-chloro-2-ethoxy-phenyl)-pyrimidin-4-ylamino]-benzyl ester |
| 65 | | 0.140 | {4-[6-(5-Chloro-2-ethoxy-phenyl)-2-methylamino-pyrimidin-4-ylamino]-phenyl}-methanol |

TABLE 1-continued

| Compound | | LPAAT-β cell-free assay (IC$_{50}$, μM) | Compound Name |
|---|---|---|---|
| 66 | | 0.450 | 6-(5-Chloro-2-ethoxy-phenyl)-N*4*-(4-oxazol-5-yl-phenyl)-pyrimidine-2,4-diamine |
| 67 | | prodrug | (S)-2-Amino-succinic acid 4-{4-[2-amino-6-(5-chloro-2-ethoxy-phenyl)-pyrimidin-4-ylamino]-benzyl}ester |
| 68 | | prodrug | 2-Amino-propionic acid 4-[2-amino-6-(5-chloro-2-ethoxy-phenyl)-pyrimidin-4-ylamino]-benzyl ester |
| 69 | | prodrug | Succinic acid mono-(2-{4-[2-amino-6-(5-chloro-2-ethoxy-phenyl)-pyrimidin-4-ylamino]-phenyl}-ethyl)ester |
| 70 | | 0.029 | 2-{4-[2-Amino-6-(5-bromo-2-ethoxy-phenyl)-pyrimidin-4-ylamino]-phenyl}-ethanol |

TABLE 1-continued

| Compound | LPAAT-β cell-free assay (IC$_{50}$, μM) | Compound Name |
|---|---|---|
| 71 | 0.21 | N*4*-(4-Chloro-phenyl)-6-(5-methoxy-2-methyl-phenyl)-pyrimidine-2,4-diamine |
| 72 | 0.45 | 2-[2-Amino-6-(4-chloro-phenylamino)-pyrimidin-4-yl]-4-bromo-phenol |
| 73 | 0.16 | N*4*-(4-Chloro-phenyl)-6-(2,5-dimethyl-phenyl)-pyrimidine-2,4-diamine |
| 74 | 0.55 | 2-{4-[2-Amino-6-(2,5-dimethyl-phenyl)-pyrimidin-4-ylamino]-phenyl}-ethanol |
| 75 | 0.18 | 5-[2-Amino-6-(5-bromo-2-methyl-phenyl)-pyrimidin-4-ylamino]-2-chloro-N-methyl-benzamide |

TABLE 1-continued

| | Compound | LPAAT-β cell-free assay (IC$_{50}$, μM) | Compound Name |
|---|---|---|---|
| 76 | | 0.71 | 6-(5-Fluoro-2-methyl-phenyl)-N*4*-(4-trifluoromethyl-phenyl)-pyrimidine-2,4-diamine |
| 77 | | 0.37 | 5-[2-Amino-6-(5-chloro-2-methyl-phenyl)-pyrimidin-4-ylamino]-2-bromo-N-methyl-benzamide |
| 78 | | 0.21 | 5-[2-Amino-6-(5-bromo-2-methyl-phenyl)-pyrimidin-4-ylamino]-2-bromo-N-methyl-benzamide |
| 79 | | 0.9 | 5-[2-Amino-6-(5-chloro-2-methyl-phenyl)-pyrimidin-4-ylamino]-isoindole-1,3-dione |
| 80 | | prodrug | N-[4-(5-Chloro-2-methyl-phenyl)-6-(4-trifluoromethyl-phenylamino)-pyrimidin-2-yl]-succinamic acid |

TABLE 1-continued

| Compound | LPAAT-β cell-free assay (IC$_{50}$, μM) | Compound Name |
|---|---|---|
| 81 | 0.19 | [6-(5-Bromo-2-methyl-phenyl)-(4-azido-phenyl)-pyrimidine]-2,4-diamine |
| 82 | 0.1 | 6-(5-Bromo-2-methyl-phenyl)-N*4*-(4-trifluoromethyl-phenyl)-pyrimidine-2,4-diamine |
| 83 | 1.3 | 3-(4-{4-[2-Amino-6-(5-chloro-2-methyl-phenyl)-pyrimidin-4-ylamino]-phenyl}-oxazol-2-yl)-propionic acid |
| 84 | 0.031 | 6-(5-Bromo-2-methyl-phenyl)-N*4*-(4-chloro-phenyl)-pyrimidine-2,4-diamine |
| 85 | 0.018 | 6-(5-Bromo-2-methyl-phenyl)-N*4*-(4-bromo-phenyl)-pyrimidine-2,4-diamine |

TABLE 1-continued

| Compound | | LPAAT-β cell-free assay (IC$_{50}$, μM) | Compound Name |
|---|---|---|---|
| 86 | | 0.04 | 4-[2-Amino-6-(5-bromo-2-methyl-phenyl)-pyrimidin-2-ylamino]-benzonitrile |
| 87 | | 1.2 | 6-(5-Bromo-2-methyl-phenyl)-N*4*-(4-oxazol-4-yl-phenyl)-pyrimidine-2,4-diamine |
| 88 | | 0.021 | 6-(5-Bromo-2-methyl-phenyl)-N*4*-(4-nitro-phenyl)-pyrimidine-2,4-diamine |
| 89 | | 0.1 | N*4*-(4-Chloro-phenyl)-6-[5-chloro-2-(2,2,2-trifluoro-ethoxy)-phenyl]-pyrimidine-2,4-diamine |
| 90 | | 0.78 | 2-{4-[2-Amino-6-(5-chloro-2-ethoxy-phenyl)-pyrimidin-4-ylamino]-phenoxy}-ethanol |

TABLE 1-continued

| Compound | | LPAAT-β cell-free assay (IC$_{50}$, μM) | Compound Name |
|---|---|---|---|
| 91 | | 0.19 | N*4*-(4-Bromo-phenyl)-6-[5-bromo-2-(2,2,2-trifluoro-ethoxy)-phenyl]-pyrimidine-2,4-diamine |
| 92 | | 0.23 | 3-{4-[2-Amino-6-(5-chloro-2-ethoxy-phenyl)-pyrimidin-4-ylamino]-phenyl}-propan-1-ol |
| 93 | | 0.12 | 4-{4-[2-Amino-6-(5-chloro-2-ethoxy-phenyl)-pyrimidin-4-ylamino]-phenyl}-butan-1-ol |
| 94 | | 0.032 | 6-(5-Chloro-2-ethoxy-phenyl)-N*4*-(4-fluoro-phenyl)-pyrimidine-2,4-diamine |
| 95 | | 0.31 | 4-{4-[2-Amino-6-(5-chloro-2-ethoxy-phenyl)-pyrimidin-4-ylamino]-phenyl}-butyric acid |

TABLE 1-continued

| Compound | | LPAAT-β cell-free assay (IC$_{50}$, μM) | Compound Name |
|---|---|---|---|
| 96 | (structure) | 0.073 | 4-[2-Amino-6-(5-chloro-2-ethoxy-phenyl)-pyrimidin-4-ylamino]-benzenesulfonamide |
| 97 | (structure) | 0.073 | 6-(5-Chloro-2-methyl-phenyl)-N*4*-(4-fluoro-phenyl)-pyrimidin2-2,4-diamine |
| 98 | (structure) | 0.091 | N*4*-(4-Chloro-phenyl)-6-(2,3,5-trichloro-phenyl)-pyrimidine-2,4-diamine |
| 99 | (structure) | 0.13 | N*4*-(4-Bromo-phenyl)-6-(2,3,5-trichloro-phenyl)-pyrimidine-2,4-diamine |
| 100 | (structure) | 0.049 | 2-{4-[2-Amino-6-(5-bromo-2-methyl-phenyl)-pyrimidin-4-ylamino]-phenyl}-ethanol |

TABLE 1-continued

| Compound | | LPAAT-β cell-free assay (IC$_{50}$, μM) | Compound Name |
|---|---|---|---|
| 101 | (structure) | 0.29 | 4-{4-[2-Amino-6-(5-bromo-2-methyl-phenyl)-pyrimidin-4-ylamino]-phenyl}-butan-1-ol |
| 102 | (structure) | 0.5 | 6-(2,3,5-trichloro-phenyl)-N*4*-(4-trifluoromethyl-phenyl)-pyrimidine-2,4-diamine |
| 103 | (structure) | 0.054 | 1-{4-[2-Amino-6-(5-chloro-2-methyl-phenyl)-pyrimidin-4-ylamino]-phenyl}-2,2,2-trifluoro-ethanol |
| 104 | (structure) | 0.16 | 1-{4-[2-Amino-6-(5-chloro-2-methyl-phenyl)-pyrimidin-4-ylamino]-phenyl}-ethanone-oxime |
| 105 | (structure) | 1.8 | N*4*-(4-Chloro-phenyl)-6-(2-trifluoromethyl-phenyl)-pyrimidine-2,4-diamine |
| 106 | (structure) | 1.1 | N*4*-(4-Chloro-phenyl)-6-phenyl-pyrimidine-2,4-diamine |

TABLE 1-continued

| | Compound | LPAAT-β cell-free assay (IC$_{50}$, μM) | Compound Name |
|---|---|---|---|
| 107 | | 0.31 | 6-(3-Chloro-phenyl)-N*4*-(4-trifluoromethyl-phenyl)-pyrimidine-2,4-diamine |
| 108 | | 0.015 | 6-(5-Chloro-2-methyl-phenyl)-N*4*-(4-nitro-phenyl)-pyrimidine-2,4-diamine |
| 109 | | 0.85 | 3-{4-[2-Amino-6-(5-Chloro-2-methyl-phenyl)-pyrimidin-4-ylamino]-phenyl}-propan-1-ol |
| 110 | | 0.21 | 4-{4-[2-Amino-6-(5-Chloro-2-methyl-phenyl)-pyrimidin-4-ylamino]-phenyl}-butan-1-ol |
| 111 | | 0.28 | 6-(5-Chloro-2-methyl-phenyl)-N*4*-(3-methylsulfanyl-phenyl)-pyrimidine-2,4-diamine |

TABLE 1-continued

| Compound | | LPAAT-β cell-free assay (IC$_{50}$, μM) | Compound Name |
|---|---|---|---|
| 112 | | 0.64 | 6-(3,5-Dichloro-phenyl)-N*4*-(4-trifluoromethyl-phenyl)-pyrimidine-2,4-diamine |
| 113 | | 0.19 | {5-[2-Amino-6-(5-chloro-2-methyl-phenyl)-pyrimidin-4-ylamino]-2-chloro-phenyl}-methanol |
| 114 | | 0.042 | 3-[2-Amino-6-(5-chloro-2-methyl-phenyl)-pyrimidin-4-ylamino]-benzoic acid ethyl ester |
| 115 | | 0.21 | 6-(5-Chloro-2-methyl-phenyl)-N*4*-(3-ethyl-phenyl)-pyrimidine-2,4-diamine |
| 116 | | 1.1 | 2-{4-{2-Amino-6-(5-chloro-2-methyl-phenyl)-pyrimidin-2-yl-amino]-phenyl}-propane-1,3-diol |

TABLE 1-continued

| Compound | | LPAAT-β cell-free assay (IC$_{50}$, μM) | Compound Name |
|---|---|---|---|
| 117 | | 4.9 | 6-(5-Chloro-2-ethoxy-phenyl)-N*4*-(2-chloro-phenyl)-pyrimidine-2,4-diamine |
| 118 | | 0.71 | 6-(2,3-Dichloro-phenyl)-N*4*-(4-chloro-phenyl)-pyrimidine-2,4-diamine |
| 119 | | 0.61 | 6-(3-Bromo-phenyl)-N*4*-(4-trifluoromethyl-phenyl)-pyrimidine-2,4-diamine |
| 120 | | 0.18 | 1-{4-[2-amino-6-(5-chloro-2-ethoxyphenyl)pyrimidin-4-ylamino]phenyl}-2-methyl-propan-2-ol |
| 121 | | 0.049 | 1-{4-[2-amino-6-(5-chloro-2-ethoxyphenyl)pyrimidin-4-ylamino]phenyl}ethanone |
| 122 | | 1.2 | 6-(5-chloro-2-ethoxyphenyl)-N*4*-(4-chlorophenyl)-N*4*-methylpyrimidine-2,4-diamine |

TABLE 1-continued

| Compound | | LPAAT-β cell-free assay (IC$_{50}$, μM) | Compound Name |
|---|---|---|---|
| 123 | (structure) | 0.15 | 1-{4-[2-amino-6-(5-chloro-2-methylphenyl)pyrimidin-4-ylamino]phenyl}ethanone |
| 124 | (structure) | 0.11 | 6-(5-chloro-2-ethoxyphenyl)-N*4*-(4-methanesulfonylphenyl)pyrimidine-2,4-diamine |
| 125 | (structure) | 0.09 | N*4*-(1H-Benzotriazol-5-yl)-6-(5-chloro-2-methylphenyl)pyrimidine-2,4-diamine |
| 126 | (structure) | 0.5 | 6-(5-chloro-2-methylphenyl)-N*4*-(6-trifluoromethylpyridin-3-yl)pyrimidine-2,4-diamine |
| 127 | (structure) | 0.034 | 1-{4-[2-amino-6-(5-bromo-2-ethoxyphenyl)pyrimidin-4-ylamino]phenyl}ethanone |

TABLE 1-continued

| Compound | | LPAAT-β cell-free assay (IC$_{50}$, μM) | Compound Name |
|---|---|---|---|
| 128 | | 0.19 | 6-(5-bromo-2-ethoxyphenyl)-N*4*-(6-trifluoromethylpyridin-3-yl)-pyrimidine-2,4-diamine |
| 129 | | 0.014 | 1-{4-[2-Amino-6-(5-bromo-2-ethoxy-phenyl)-pyrimidin-4-ylamino]-phenyl}-2,2,2-trifluoro-ethanol |
| 130 | | 0.084 | 1-{4-[2-Amino-6-(5-bromo-2-ethoxy-phenyl)-pyrimidin-4-ylamino]-phenyl}-ethanone-oxime |
| 131 | | 0.012 | 1-{4-[2-Amino-6-(5-bromo-2-ethoxy-phenyl)-pyrimidin-4-ylamino]-phenyl}-2,2,2-trifluoro-ethanone |
| 132 | | 0.14 | 6-(5-Bromo-2-ethoxy-phenyl)-N*4*-(3,4-dimethyl-phenyl)-pyrimidine-2,4-diamine |

TABLE 1-continued

| Compound | | LPAAT-β cell-free assay (IC$_{50}$, μM) | Compound Name |
|---|---|---|---|
| 133 | | 0.015 | 6-(5-Bromo-2-ethoxy-phenyl)-N*4*-(4-nitro-phenyl)-pyrimidine-2,4-diamine |
| 134 | | 0.11 | 1-{4-[2-Amino-6-(5-bromo-2-ethoxy-phenyl)-N*4*-(3,4-dimethyl-phenyl)-pyrimidin-4-ylamino]-phenyl}-ethanol |
| 135 | | 0.008 | 6-(5-Bromo-2-propoxy-phenyl)-N*4*-(4-chloro-phenyl)-pyrimidine-2,4-diamine |
| 136 | | 0.17 | 6-(5-Bromo-2-isopropoxy-phenyl)-N*4*-(4-chloro-phenyl)-pyrimidine-2,4-diamine |
| 137 | | 0.26 | 6-(5-Bromo-2-ethoxy-phenyl)-N*4*-[4-(1-methoxy-ethyl)-phenyl]-pyrimidin-2,4-diamine |

TABLE 1-continued

| Compound | | LPAAT-β cell-free assay (IC$_{50}$, μM) | Compound Name |
|---|---|---|---|
| 138 | | 0.95 | 3-[2-Amino-6-(5-Bromo-2-ethoxy-phenyl)-pyrimidin-4-ylamino]-benzamide |
| 139 | | 0.34 | 1-{4-[2-Amino-6-(3-chloro-phenyl)-pyrimidin-4-ylamino]-phenyl}ethanone |
| 140 | | 0.1 | N*4*-{4-Azido-phenyl)-6-(2-ethoxy-5-iodo-phenyl)-pyrimidine-2,4-diamine |
| 141 | | 0.39 | 2-{4-[2-Amino-6-(5-bromo-2-isopropoxy-phenyl)-pyrimidin-4-ylamino]-phenyl}-ethanol |
| 142 | | 0.018 | 6-(5-Bromo-2-methoxy-phenyl)-N*4*-(4-chloro-phenyl)-pyrimidine-2,4-diamine |

TABLE 1-continued

| Compound | | LPAAT-β cell-free assay (IC$_{50}$, μM) | Compound Name |
|---|---|---|---|
| 143 | | 0.022 | 6-[5-Bromo-2-(2-methoxy-ethoxy)-phenyl]-N*4*-(4-chloro-phenyl)-pyrimidine-2,4-diamine |
| 144 | | 0.46 | 6-(5-Bromo-2-ethoxy-phenyl)-N*4*-quinolin-3-yl-pyrimidine-2,4-diamine |
| 145 | | 0.005 | 6-(5-Bromo-2-hexyloxy-phenyl)-N*4*-(4-chloro-phenyl)-pyrimidine-2,4-diamine |
| 146 | | 0.003 | 6-(2-Benzyloxy-5-bromo-phenyl)-N*4*-(4-chloro-phenyl)-pyrimidine-2,4-diamine |
| 147 | | 0.39 | 1-{4-[2-Amino-6-(2,3,5-trichloro-phenyl)-pyrimidin-4-ylamino]-phenyl}-ethanone oxime |

TABLE 1-continued

| | Compound | LPAAT-β cell-free assay (IC$_{50}$, μM) | Compound Name |
|---|---|---|---|
| 148 | | 0.005 | 6-(5-Bromo-2-butoxy-phenyl)-N*4*-(4-chloro-phenyl)-pyrimidine-2,4-diamine |
| 149 | | 0.071 | 6-[5-Bromo-2-(2-morpholin-4-yl-ethoxy)-phenyl]-N*4*-(4-chloro-phenyl)-pyrimidine-2,4-diamine |
| 150 | | 0.1 | 6-(5-Bromo-2-methoxy-phenyl)-N*4*-(4-trifluoromethyl-phenyl)-pyrimidine-2,4-diamine |
| 151 | | 0.055 | 2-{4-[2-Amino-6-(5-bromo-2-methoxy-phenyl)-pyrimidin-4-ylamino]-phenyl}-ethanol |
| 152 | | 0.24 | N*4*-(4-Chloro-phenyl)-6-(2-phenoxy-phenyl)-pyrimidin-2,4-diamine |

TABLE 1-continued

| Compound | | LPAAT-β cell-free assay (IC$_{50}$, μM) | Compound Name |
|---|---|---|---|
| 153 | [structure] | 0.006 | 6-(2-Benzyloxy-5-bromo-phenyl)-N*4*-(4-trifluoromethyl-phenyl)-pyrimidine-2,4-diamine |
| 154 | [structure] | 0.098 | 1-{4-[2-Amino-6-(2,5-dichloro-phenyl)-pyrimidin-4-yl-amino]-phenyl}-ethanone oxime |
| 155 | [structure] | 0.004 | 6-(2-Benzyloxy-5-chloro-phenyl)-N*4*-(4-chloro-phenyl)-pyrimidine-2,4-diamine |
| 156 | [structure] | 1.4 | 6-[5-Bromo-2-(3-dimethylamino-propoxy)-phenyl]-N*4*-(4-chloro-phenyl)-pyrimidine-2,4-diamine |
| 157 | [structure] | 0.006 | 6-(2-Benzyloxy-5-chloro-phenyl)-N*4*-(4-trifluoromethyl-phenyl)-pyrimidine-2,4-diamine |

TABLE 1-continued

| | Compound | LPAAT-β cell-free assay (IC$_{50}$, μM) | Compound Name |
|---|---|---|---|
| 158 | | 0.016 | 2-{4-[2-Amino-6-(2-benzyloxy-5-chloro-phenyl)-pyrimidin-4-ylamino]-phenyl}-ethanol |
| 159 | | 0.2 | 4-[2-Amino-6-(5-bromo-2-ethoxy-phenyl)-pyrimidin-4-ylamino]-phenyl-boronic acid |
| 160 | | 0.038 | 4-[2-Amino-6-(5-bromo-2-methoxy-phenyl)-pyrimidin-4-ylamino]-benzonitrile |
| 161 | | 0.014 | 6-(5-Bromo-2-methoxy-phenyl)-N*4*-(4-nitro-phenyl)-pyrimidine-2,4-diamine |
| 162 | | 0.036 | 6-(5-Bromo-2-methoxy-phenyl)-N*4*-(4-bromo-phenyl)-pyrimidine-2,4-diamine |

TABLE 1-continued

| | Compound | LPAAT-β cell-free assay (IC$_{50}$, μM) | Compound Name |
|---|---|---|---|
| 163 | | 0.31 | N*4*-(4-Bromo-phenyl)-6-(5-chloro-2-ethyl-phenyl)-pyrimidine-2,4-diamine |
| 164 | | 0.67 | 6-(5-Chloro-2-ethyl-phenyl)-N*4*-(4-trifluoromethyl-phenyl)-pyrimidine-2,4-diamine |
| 165 | | 0.003 | 6-[5-Bromo-2-(4-chloro-benzyloxy)-phenyl]-N*4*-(4-chloro-phenyl)-pyrimidine-2,4-diamine |
| 166 | | 0.005 | 6-(5-Bromo-2-phenethyloxy-phenyl)-N*4*-(4-chloro-phenyl)-pyrimidine-2,4-diamine |
| 167 | | 0.18 | 6-(5-Chloro-2-ethyl-phenyl)-N*-4*-(4-chloro-phenyl)-pyrimidine-2,4-diamine |

TABLE 1-continued

| Compound | | LPAAT-β cell-free assay (IC$_{50}$, μM) | Compound Name |
|---|---|---|---|
| 168 | [structure] | 0.016 | 6-(5-Chloro-2-cyclohexylmethoxy-phenyl)-N*4*-(4-chloro-phenyl)-pyrimidine-2,4-diamine |
| 169 | [structure] | 0.093 | 6-(5-Chloro-2-ethyl-phenyl)-N*-4*-(4-nitro-phenyl)-pyrimidine-2,4-diamine |
| 170 | [structure] | 0.024 | 3-[2-Amino-6-(2,5-dichloro-phenyl)-pyrimidin-4-ylamino]-benzoic acid ethyl ester |
| 171 | [structure] | 0.26 | 3-[2-Amino-6-(5-bromo-2-methoxy-phenyl)-pyrimidin-4-ylamino]-benzoic acid ethyl ester |
| 172 | [structure] | 0.045 | (4-Bromo-phenyl)-[6-(5-chloro-2-methyl-phenyl)-pyrimidin-4-yl]-amine |

TABLE 1-continued

| | Compound | LPAAT-β cell-free assay (IC$_{50}$, μM) | Compound Name |
|---|---|---|---|
| 173 | | 0.21 | 4-[2-Amino-6-(5-bromo-2-methyl-phenyl)-pyrimidin-4-ylamino]-phenyl-boronic acid |
| 174 | | 0.009 | 6-(2-Allyloxy-5-chloro-phenyl)-N*4*-(4-chloro-phenyl)-pyrimidine-2,4-diamine |
| 175 | | 0.1 | 2-{4-[2-amino-6-(5-chloro-2-ethyl-phenyl)-pyrimidin-4-ylamino]-phenyl}-ethanol |
| 176 | | 0.06 | 2-{4-[6-(5-Chloro-2-methyl-phenyl)-pyrimidin-4-ylamino]-phenyl}-ethanol |
| 177 | | 0.002 | 6-(2-Benzyloxy-5-bromo-phenyl)-N*4*-(4-nitro-phenyl)-pyrimidine-2,4-diamine |

TABLE 1-continued

| Compound | | LPAAT-β cell-free assay (IC$_{50}$, μM) | Compound Name |
|---|---|---|---|
| 178 | | 0.021 | 6-[5-Bromo-2-(4-nitro-benzyloxy)-phenyl]-N*4*-(4-chloro-phenyl)-pyrimidine-2,4-diamine |
| 179 | | 0.18 | N*4*-(4-Chloro-3-trifluoromethyl-phenyl)-6-(2,5-dichloro-phenyl)-pyrimidin-2,4-diamine |
| 180 | | 0.16 | [6-(5-Bromo-2-ethoxy-phenyl)-pyrimidin-4-yl]-(4-trifluoromethyl-phenyl)-amine |
| 181 | | 0.04 | [6-(5-Bromo-2-ethoxy-phenyl)-pyrimidin-4-yl]-(4-bromo-phenyl)-amine |
| 182 | | 0.004 | 6-[5-Bromo-2-(2-methoxy-benzyloxy)-phenyl]-N*4*-(4-chloro-phenyl)-pyrimidine-2,4-diamine |

TABLE 1-continued

| Compound | | LPAAT-β cell-free assay (IC$_{50}$, μM) | Compound Name |
|---|---|---|---|
| 183 | (structure) | 0.088 | 4-[2-Amino-6-(5-bromo-2-ethoxy-phenyl)-pyrimidin-4-ylamino]-N-hydroxy-benzamide |
| 184 | (structure) | 0.2 | 5-[2-Amino-6-(5-bromo-2-methoxy-phenyl)-pyrimidin-4-ylamino]-2-chloro-N-methyl-benzamide |
| 185 | (structure) | 0.004 | 6-[5-Bromo-2-(4-methoxy-benzyloxy)-phenyl]-N*4*-(4-chloro-phenyl)-pyrimidine-2,4-diamine |
| 186 | (structure) | 0.74 | 4-[2-Amino-6-(5-bromo-2-ethoxy-phenyl)-pyrimidine-4-ylamino]-benzamide |
| 187 | (structure) | 0.022 | 6-(5-Bromo-2-chloro-phenyl)-N*4*-(4-chloro-phenyl)-pyrimidine-2,4-diamine |

TABLE 1-continued

| | Compound | LPAAT-β cell-free assay (IC$_{50}$, μM) | Compound Name |
|---|---|---|---|
| 188 | | 0.021 | 6-[5-Bromo-2-(2-methoxy-benzyloxy)-phenyl]-N*4*-p-tolyl-pyrimidine-2,4-diamine |
| 189 | | 0.079 | 6-(5-Bromo-2-chloro-phenyl)-N*4*-(4-trifluoromethyl-phenyl)-pyrimidine-2,4-diamine |
| 190 | | 0.03 | [6-(5-Bromo-2-ethoxy-phenyl)-pyrimidin-4-yl]-(4-chloro-phenyl)-amine |
| 191 | | 0.02 | 2-{4-[6-(5-Bromo-2-ethoxy-phenyl)-pyrimidine-4-ylamino]-phenyl}-ethanol |
| 192 | | 0.06 | [6-(5-Bromo-2-ethoxy-phenyl)-pyrimidin-4-yl]-(4-fluoro-phenyl)-amine |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:

1. A compound or physiologically acceptable salt thereof, wherein the compound has the formula:

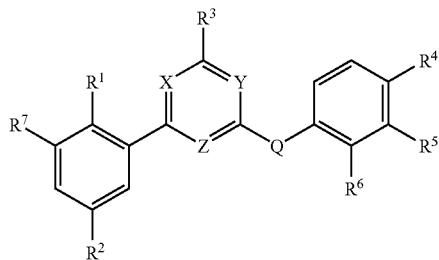

wherein:
X and Y are N, and Z is CH or CR where R is alkyl, alkoxy, Cl, Br, $NH_2$, NHR' or NR'R" where R' and R" independently are alkyl;

Q is NR where R is H or alkyl;

$R^1$ is OH, alkyl, alkoxy, Cl, F, Br, $CR_3$ where $R_3$ is $Cl_3$, $F_3$ or $Br_3$, $NH_2$, NHR or NRR' where R and R' independently are alkyl;

$R^2$ is OH, alkyl, alkoxy, Cl, F, Br, I or $CR_3$ where $R_3$ is $Cl_3$, $F_3$ or $Br_3$;

$R^7$ is H, OH, alkyl, alkoxy, Cl, F, Br, I or $CR_3$ where $R_3$ is $Cl_3$, $F_3$ or $Br_3$;

$R^3$ is H, alkyl, alkoxy, Cl, $CCl_3$, $NH_2$, NHR or NRR' where R and R' independently are alkyl or acyl containing group;

one of $R^4$ or $R^5$ is acyl containing group, and the other is H, OH, alkyl, alkenyl, alkynyl, alkoxy, $(CH_2)_n$-OR where R is H or alkyl and n is 1-10, Cl, F, Br, $CR_3$ where $R_3$ is $Cl_3$, $F_3$ or $Br_3$, acyl containing group, heterocycle, $N^+(=O)O^-$, C≡N, $N_3$, $B(OH)_2$, SH, SR or $S(=O)_2R$ where R is alkyl, $NH_2$, NHR or NRR' where R and R' independently are alkyl;

$R^6$ is H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl containing group, heterocycle, $N^+(=O)O^-$, C≡N, $N_3$, $B(OH)_2$, SH, SR or $S(=O)_2R$ where R is alkyl, $NH_2$, NHR or NRR' where R and R' independently are alkyl, or $R^5$ and $R^6$ are taken together with the benzene ring to form a heterocycle.

2. A compound or physiologically acceptable salt thereof, wherein the compound has the formula:

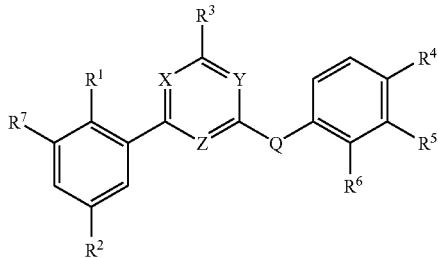

wherein:
X and Y are N, and Z is CH or CR where R is alkyl, alkoxy, Cl, Br, $NH_2$, NHR' or NR'R" where R' and R" independently are alkyl;
Q is NR where R is H or alkyl;
$R^1$ is alkyl, alkoxy or Cl;
$R^2$ is OH, alkyl, alkoxy, Cl, F, Br, I or $CR_3$ where $R_3$ is $Cl_3$, $F_3$ or $Br_3$;
$R^7$ is H, OH, alkyl, alkoxy, Cl, F, Br, I or $CR_3$ where $R_3$ is $Cl_3$, $F_3$ or $Br_3$;
$R^3$ is alkoxy, Cl, $CCl_3$, $NH_2$, NHR or NRR' where R and R' independently are alkyl or acyl containing group;
$R^4$, $R^5$, and $R^6$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl containing group, heterocycle, $N^+(=O)O^-$, $C\equiv N$, $N_3$, $B(OH)_2$, SH, SR or $S(=O)_2R$ where R is alkyl, $NH_2$, NHR or NRR' where R and R' independently are alkyl, or $R^4$ and $R^5$ or $R^5$ and $R^6$ are taken together with the benzene ring to form a heterocycle.

3. A compound or physiologically acceptable salt thereof, wherein the compound has the formula:

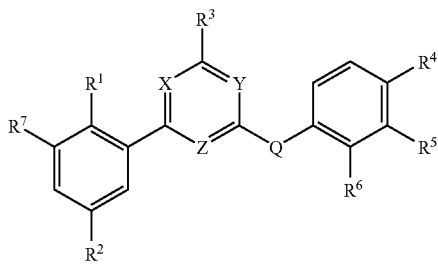

wherein:
X and Y are N, and Z is CH or CR where R is alkyl, alkoxy, Cl, Br, $NH_2$, NHR' or NR'R"where R'and R" independently are alkyl;
Q is NR where R is H or alkyl;
$R^1$ is OH, alkyl, alkoxy, Cl, F, Br, $CR_3$ where $R_3$ is $Cl_3$, $F_3$ or $Br_3$, $NH_2$, NHR or NRR' where R and R' independently are alkyl;
$R^2$ is Cl or Br;
$R^7$ is H, OH, alkyl, alkoxy, Cl, F, Br, I or $CR_3$ where $R_3$ is $Cl_3$, $F_3$ or $Br_3$;
$R^3$ is H, alkyl, alkoxy, Cl, $CCl_3$, $NH_2$, NHR or NRR' where R and R' independently are alkyl or acyl containing group;
$R^4$, $R^5$, and $R^6$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl containing group, heterocycle, $N^+(=O)O^-$, $C\equiv N$, $N_3$, $B(OH)_2$, SH, SR or $S(=O)_2R$ where R is alkyl, $NH_2$, NHR or NRR' where R and R' independently are alkyl, or $R^4$ and $R^5$ or $R^5$ and $R^6$ are taken together with the benzene ring to form a heterocycle.

4. A compound or physiologically acceptable salt thereof, wherein the compound has the formula:

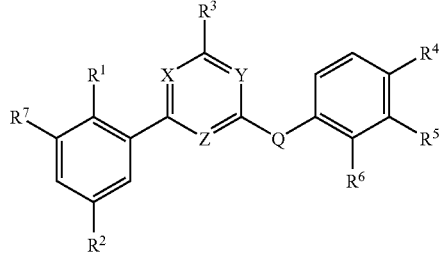

wherein:
X and Y are N, and Z is CH or CR where R is alkyl, alkoxy, Cl, Br, $NH_2$, NHR' or NR'R" where R'and R" independently are alkyl;
Q is NR where R is H or alkyl;
$R^1$ is OH, alkyl, alkoxy, Cl, F, Br, $CR_3$ where $R_3$ is $Cl_3$, $F_3$ or $Br_3$, $NH_2$, NHR or NRR' where R and R' independently are alkyl;
$R^2$ is OH, alkyl, alkoxy, Cl, F, Br, I or $CR_3$ where $R_3$ is $Cl_3$, $F_3$ or $Br_3$;
$R^7$ is H, OH, alkyl, alkoxy, Cl, F, Br, I or $CR_3$ where $R_3$ is $Cl_3$, $F_3$ or $Br_3$;
$R^3$ is alkyl or $NH_2$;
$R^4$, $R^5$, and $R^6$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl containing group, heterocycle, $N^+(=O)O^-$, $C\equiv N$, $N_3$, $B(OH)_2$, SH, SR or $S(=O)_2R$ where R is alkyl, $NH_2$, NHR or NRR' where R and R' independently are alkyl, or $R^4$ and $R^5$ or $R^5$ and $R^6$ are taken together with the benzene ring to form a heterocycle.

5. A compound or physiologically acceptable salt thereof, wherein the compound has the formula:

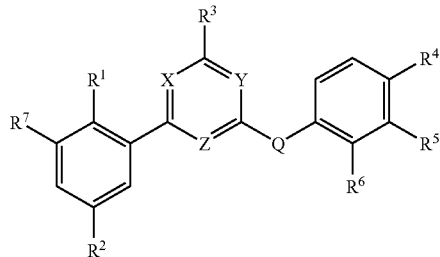

wherein:
X and Y are N, and Z is CH or CR where R is alkyl, alkoxy, Cl, Br, $NH_2$, NHR' or NR'R" where R' and R" independently are alkyl;
Q is NR where R is H or alkyl;
$R^1$ is OH, alkyl, alkoxy, Cl, F, Br, $CR_3$ where $R_3$ is $Cl_3$, $F_3$ or $Br_3$, $NH_2$, NHR or NRR' where R and R' independently are alkyl;

R² is OH, alkyl, alkoxy, Cl, F, Br, I or CR₃ where R₃ is Cl₃, F₃ or Br₃;

R⁷ is H, OH, alkyl, alkoxy, Cl, F, Br, I or CR₃ where R₃ is Cl₃, F₃ or Br₃;

R³ is H, alkyl, alkoxy, Cl, CCl₃, NH₂, NHR or NRR' where R and R' independently are alkyl or acyl containing group;

one of R⁴ or R⁵ is alkyl, Cl, Br, CF₃, CH₂—OH, (CH₂)₂—OH, N⁺(=O)O⁻, C≡N, or C(=O)R wherein R is alkyl or alkoxy, and the other is H, OH, alkyl, alkenyl, alkynyl, alkoxy, (CH₂)ₙ—OR where R is H or alkyl and n is 1-10, Cl, F, Br, CR₃ where R₃ is Cl₃, F₃ or Br₃, acyl containing group, heterocycle, N⁺(=O)O⁻, C≡N, N₃, B(OH)₂, SH, SR or S(=O)₂R where R is alkyl, NH₂, NHR or NRR' where R and R' independently are alkyl, or R⁴ and R⁵ are taken together with the benzene ring to form indazole;

R⁶ is H, OH, alkyl, alkenyl, alkynyl, alkoxy, (CH₂)ₙ—OR where R is H or alkyl and n is 1-10, Cl, F, Br, CR₃ where R₃ is Cl₃, F₃ or Br₃, acyl containing group, heterocycle, N⁺(=O)O⁻, C≡N, N₃, B(OH)₂, SH, SR or S(=O)₂R where R is alkyl, NH₂, NHR or NRR' where R and R' independently are alkyl, or R⁵ and R⁶ are taken together with the benzene ring to form a heterocycle.

6. A compound or salt thereof wherein the compound is any one of compounds 6-(5-Chloro-2-methoxy-phenyl)-N*4*-p-tolyl-pyrimidine-2,4-diamine, 6-(5-Chloro-2-methoxy-phenyl)-N*4*-(4chloro-phenyl)-pyrimidine-2,4-diamine, 6-(5-Chloro-2-methoxy-phenyl)-N*4*-(1H-indazol-6-yl)-pyrimidine-2,4-diamine, 6-(5-Chloro-2-methoxy-phenyl)-N*4*-(4-trifluoromethylphenyl)-pyrimidine-2,4-diamine, N*4*-(4-Bromo-phenyl)-6-(5-chloro-2-methoxy-phenyl)-pyrimidine-2,4-diamine, 4-[2-Amino-6-(5-chloro-2-methoxy-phenyl)-pyrimidin-4-ylamino]-phenol, 6-(5-Chloro-2-methoxy-phenyl)-N*4*-(4-methoxy-phenyl)-pyrimidine-2,4-diamine, N*4*-Benzothiazol-6-yl-6-(5-chloro-2-methoxy-phenyl)-pyrimidine-2,4-diamine, 4-[2-Amino-6-(5-chloro-2-methoxy-phenyl)-pyrimidin-4-ylamino]-benzoic acid methyl ester, {4-[2-Amino-6-(5-chloro-2-methoxy-phenyl)-pyrimidin-4-ylamino]-phenyl}-methanol, 6-(5-Chloro-2-methoxy-phenyl)-N*4*-(4-nitro-phenyl)-pyrimidine-2,4-diamine, N*4*-(4-Amino-phenyl)-6-(5-chloro-2-methoxy-phenyl)-pyrimidine-2,4-diamine, N*4*-Benzo[1,3]dioxol-5-yl-6-(5-chloro-2-methoxy-phenyl)-pyrimidine-2,4-diamine, N*4*-(4-Bromo-phenyl)-6-(2,5-dichloro-phenyl)-pyrimidine-2,4-diamine, 6-(2,5-Dichloro-phenyl)-N*4*-p-tolyl-pyrimidine-2,4-diamine, 6-(2,5-Dichloro-phenyl)-N*4*-(4-methoxy-phenyl)-pyrimidine-2,4-diamine, 4-[2-Amino-6-(2,5-dichloro-phenyl)-pyrimidin-4-ylamino]-phenol, 6-(2,5-Dichloro-phenyl)-N*4*-(4-trifluoromethyl-phenyl)-pyrimidine-2,4-diamine, 6-(2,5-Dichloro-phenyl)-N*4*-(1H-indazol-6-yl)-pyrimidine-2,4-diamine, N*4*-(4-Chloro-phenyl)-6-(2,5-dichloro-phenyl)-pyrimidine-2,4-diamine, 4-[2-Amino-6-(2,5-dichloro-phenyl)-pyrimidin-4-yl-amino]-benzoic acid methyl ester, {4-[2-Amino-6-(2,5-dichloro-phenyl)-pyrimidin-4-yl-amino]-phenyl}-methanol, N*4*-Benzo[1,3]dioxol-5-yl-6-(2,5-dichloro-phenyl)-pyrimidine-2,4-diamine, 4-[2-Amino-6-(2,5-dichloro-phenyl)-pyrimidin-4-ylamino]-benzonitrile, 6-(2,5-Dichloro-phenyl)-N*4*-(4-nitro-phenyl)-pyrimidine-2,4-diamine, 6-(5-Chloro-2-methyl-phenyl)-N*4*-p-tolyl-pyrimidine-2,4-diamine, 6-(5-Chloro-2-methyl-phenyl)-N*4*-(4-chloro-phenyl)-pyrimidine-2,4-diamine, 6-(5-Chloro-2-methyl-phenyl)-N*4*-(4-methoxy-phenyl)-pyrimidine-2,4-diamine, 6-(5-Chloro-2-methyl-phenyl)-N*4*-(4-trifluoromethyl-phenyl)-pyrimidine-2,4-diamine, N*4*-(4-Bromo-phenyl)-6-(5-chloro-2-methyl-phenyl)-pyrimidine-2,4-diamine, 6-(5-Chloro-2-methyl-phenyl-N*4*-(1H-indazol-6-yl)-pyrimidine-2,4-diamine, 4-[2-Amino-6-(5-chloro-2-methyl-phenyl)-pyrimidin-4-ylamino]-benzonitrile, {4-[2-Amino-6-(5-chloro-2-methyl-phenyl)-pyrimidin-4-ylamino]-phenyl}-methanol, [6-(5-Chloro-2-methoxy-phenyl)-2-methyl-pyrimidin-4-yl]-(4-chloro-phenyl)-amine, [6-(5-Chloro-2-methoxy-phenyl)-2-methyl-pyrimidin-4-yl]-(4-bromo-phenyl)-amine, [6-(5-Chloro-2-methoxy-phenyl)-2-methyl-pyrimidin-4-yl]-(1H-indazol-6-yl)-amine, [6-(5-Chloro-2-methyl-phenyl)-2-methyl-pyrimidin-4-yl]-(4-bromo-phenyl)-amine, [6-(5-Chloro-2-methyl-phenyl)-2-methyl-pyrimidin-4-yl]-(4-chloro-phenyl)-amine, [6-(5-Chloro-2-methyl-phenyl)-2-methyl-pyrimidin-4-yl]-(1H-indazol-6-yl)-amine, {4-[2-Amino-6-(5-chloro-2-ethoxy-phenyl)-pyrimidin-4-ylamino]-phenyl}-methanol, 4-[2-Amino-6-(5-chloro-2-methoxy-phenyl)-pyrimidin-4-ylamino]-benzonitrile, 6-(5-Chloro-2-ethoxy-phenyl)-N*4*-(4-nitro-phenyl)-pyrimidine-2,4-diamine, 2-{4-[2-Amino-6-(5-chloro-2-ethoxy-phenyl)-pyrimidin-4-ylamino]-phenyl}-ethanol, 2-{4-[2-Amino-6-(2,5-dichloro-phenyl)-pyrimidin-4-ylamino]-phenyl}-ethanol, 2-{4-[2-Amino-6-(5-chloro-2-methyl-phenyl)-pyrimidin-4-ylamino]-phenyl}-ethanol, 2-}4-[2-Amino-6-(5-chloro-2-methoxy-phenyl)-pyrimidin-4-ylamino]-phenyl}-ethanol, 6-(5-Chloro-2-methoxy-phenyl)-5-methyl-N*4*-(1H-indazol-6-yl)-pyrimidine-2,4-diamine, 5-Bromo-6-(5-chloro-2-methoxy-phenyl)-N*4*-(1H-indazol-6-yl)-pyrimidine-2,4-diamine, 6-(5-Chloro-2-ethoxy-phenyl)-N*4*-p-tolyl-pyrimidine-2,4-diamine, 6-(5-Chloro-2-ethoxy-phenyl)-N*4*-(1H-indazol-6-yl)-pyrimidine-2,4-diamine, 6-(5-Chloro-2-ethoxy-phenyl)-N*4*-(4-chloro-phenyl)-pyrimidine-2,4-diamine, 6-(5-Chloro-2-ethoxy-phenyl)-N*4*-(4-trifluoromethyl-phenyl)-pyrimidine-2,4-diamine, 4-[2-Amino-6-(5-chloro-2-ethoxy-phenyl)-pyrimidin-4-ylamino]-benzonitrile, 6-(5-Chloro-2-ethoxy-phenyl-N*4*-(4-methoxy-phenyl)-pyrimidine-2,4-diamine, }4-[2-Amino-6-(5-bromo-2-ethoxy-phenyl)-pyrimidin-4-ylamino]-phenyl}-phenyl-methanone, 6-(5-Bromo-2-ethoxy-phenyl)-N*4*-(4-trifluoromethyl-phenyl)-pyrimidin-2,4-diamine, 4-[2-Amino-6-(5-bromo-2-ethoxy-phenyl)-pyrimidin-4-ylamino]-benzoic acid methyl ester, {4-[2-Amino-6-(5-bromo-2-ethoxy-phenyl)-pyrimidin-4-ylamino]-phenyl}-methanol, Succinic acid mono-{4-[2-amino-6-(5-chloro-2-ethoxy-phenyl)-pyrimidin-4-ylamino]-benzyl}-ester, Amino acetic acid-4-[2-amino-6-(5-chloro-2-ethoxy-phenyl)-pyrimidin-4-ylamino]-benzyl ester, {4-[6-(5-Chloro-2-ethoxy-phenyl)-2-methylamino-pyrimidin-4-ylamino]-phenyl}-methanol, 6-(5-Chloro-2-ethoxy-phenyl)-N*4*-(4-oxazol-5-yl-phenyl)-pyrimidine-2,4-diamine, (S)-2-Amino-succinic acid 4-{4-[2-amino-6-(5-chloro-2-ethoxy-phenyl)-pyrimidin-4-ylamino]-benzyl}ester, 2-Amino-propionic acid 4-[2-amino-6-(5-chloro-2-ethoxy-phenyl)-pyrimidin-4-ylamino]-benzyl ester, Succinic acid mono-(2-{4-[2-amino-6-(5-chloro-2-ethoxy-phenyl)-pyrimidin-4-ylamino]-phenyl}-ethyl) ester, 2-{4-[2-Amino-6-(5-bromo-2-ethoxy-phenyl)-pyrimidin-4-ylamino]-phenyl}-ethanol, N *4*-(4-Chloro-phenyl)-6-(5-methoxy-2-methyl-phenyl)-pyrimidine-2,4-diamine, 2-[2-Amino-6-(4-chloro-phenylamino)-pyrimidin-4-yl]-4-bromo-phenol, N*4*-(4-Chloro-phenyl)-6-(2,5-dimethyl-phenyl)-pyrimidine-2,4-diamine, 2-{4-[2-Amino-6-(2,5-dimethyl-phenyl)-pyrimidin-4-ylamino]-phenyl}-ethanol, 5-[2-Amino-6-(5-bromo-2-methyl-phenyl)-pyrimidin-4-ylamino]-2-chloro-N-methyl-benzamide, 6-(5-Fluoro-2-methyl-phenyl)-N*4*-(4-trifluoromethyl-phenyl)-pyrimidine-2,4-diamine, 5-[2-Amino-6-(5-chloro-2-methyl-phenyl)-pyrimidin-4-ylamino]-2-bromo-N-methyl-benzamide, 5-[2-Amino-6-(5- bromo-2-methyl-phenyl)-pyrimidin-4-ylamino]-2-bromo-N-methyl-benzamide, 5-[2-Amino-6-(5-chloro-2-methyl-phenyl)-pyrimidin-4-ylamino]-isoindole-1,3-dione, N-[4-(5-Chloro-2-methyl-phenyl)-6-(4-trifluoromethyl-phenylamino)-pyrimidin-2-yl]-succinamic acid, [6-(5-Bromo-2-methyl-phenyl)-(4-azido-phenyl)-pyrimidine]-2,4-diamine, 6-(5-Bromo-2-methyl-phenyl)-N*4*-(4-trifluoromethyl-phenyl)-pyrimidine-2,4-diamine, 3-(4-(4-[2-Amino-6-(5-chloro-2-methyl-phenyl)-pyrimidin-4-ylamino]-phenyl}-oxazol-2-yl)-propionic acid, 6-(5-Bromo-2-methyl-phenyl)-N*4*-(4-chloro-phenyl)-pyrimidine-2,4-diamine, 6-(5-Bromo-2-methyl-phenyl)-N*4*-(4-bromo-phenyl)-pyrimidine-2,4-diamine, 4-[2-Amino-6-(5-bromo-2-methyl-phenyl)-pyrimidin-4-ylamino]-benzonitrile, 6-(5-Bromo-2-methyl-phenyl)-N*4*-(4-oxazol-4-yl-phenyl)-pyrimidine-2,4-diamine, 6-(5-Bromo-2-methyl-phenyl-N*4*-(4-nitro-phenyl)-pyrimidine-2,4-diamine, N*4*-(4-Chloro-phenyl)-6-[5-chloro-2-(2,2,2-trifluoro-ethoxy)-phenyl]-pyrimidine-2,4-diamine, 2-{4-[2-Amino-6-(5-chloro-2-ethoxy-phenyl)-pyrimidin-4-ylamino]-phenoxy}-ethanol, N*4*-(4-Bromo-phenyl)-6-[5-bromo-2-(2,2,2-trifluoro-ethoxy)-phenyl]-pyrimidine-2,4-diamine, 3-{4-[2-Amino-6-(5-chloro-2-ethoxy-phenyl)-pyrimidin-4-ylamino]-phenyl}-propan-1-ol, 4-{4-[2-Amino-6-(5-chloro-2-ethoxy-phenyl)-pyrimidin-4-ylamino]-phenyl}-butan-1-ol, 6-(5-Chloro-2-ethoxy-phenyl)-N*4*-(4-fluoro-phenyl)-pyrimidine-2,4-diamine, 4-{4-[2-Amino-6-(5-chloro-2-ethoxy-phenyl)-pyrimidin-4-ylamino]-phenyl}-butyric acid, 4-[2-Amino-6-(5-chloro-2-ethoxy-phenyl)-pyrimidin-4-ylamino]-benzenesulfonamide, 6-(5-Chloro-2-methyl-phenyl)-N*4-(4-fluoro-phenyl)-pyrimidin2-2,4-diamine, N*4*-(4-Chloro-phenyl)-6-(2,3,5-trichloro-phenyl)-pyrimidine-2,4-diamine, N*4*-(4-Bromo-phenyl)-6-(2,3,5-trichloro-phenyl)-pyrimidine-2,4-diamine, 2-(4-[2-Amino-6-(5-bromo-2-methyl-phenyl)-pyrimidin-4-ylamino]-phenyl}-ethanol, 4-{4-[2-Amino-6-(5-bromo-2-methyl-phenyl)-pyrimidin-4-ylamino]-phenyl}-butan-1-ol, 6-(2,3,5-trichloro-phenyl)-N*4*-(4-trifluoromethyl-phenyl)-pyrimidine-2,4-diamine, 1-{4-[2-Amino-6-(5-chloro-2-methyl-phenyl)-pyrimidin-4-ylamino]-phenyl}-2,2,2-trifluoro-ethanol, 1-{4-[2-Amino-6-(5-chloro-2-methyl-phenyl)-pyrimidin-4-ylamino]-phenyl}-ethanone-oxime, 6-(5-Chloro-2-methyl-phenyl)-N*4*-(4-nitro-phenyl)-pyrimidine-2,4-diamine, 3-{4-[2-Amino-6-(5-Chloro-2-methyl-phenyl)-pyrimidin-4-ylamino]-phenyl}-propan-1-ol, 4-{4-[2-Amino-6-(5-Chloro-2-methyl-phenyl)-pyrimidin-4-ylamino]-phenyl}-butan-1-ol, 6-(5-Chloro-2-methyl-phenyl)-N*4*-(3-methylsulfanyl-phenyl)-pyrimidine-2,4-diamine, {5-[2-Amino-6-(5-chloro-2-methyl-phenyl)-pyrimidin-4-ylamino]-2-chloro-phenyl}-methanol, 3-[2-Amino-6-(5-chloro-2-methyl-phenyl)-pyrimidin-4-ylamino]-benzoic acid ethyl ester, 6-(5-Chloro-2-methyl-phenyl)-N*4*-(3-ethyl-phenyl)-pyrimidine-2,4-diamine, 2-{4-{2-Amino-6-(5-chloro-2-methyl-phenyl)-pyrimidin-2-yl-amino]-phenyl}-propane-1,3-diol, 6-(5-Chloro-2-ethoxy-phenyl)-N*4*-(2-chloro-phenyl)-pyrimidine-2,4-diamine, 1-{4-[2-amino-6-(5-chloro-2-ethoxyphenyl)pyrimidin-4-ylamino]phenyl}-2-methyl-propan-2-ol, 1-{4-[2-amino-6-(5-chloro-2-ethoxyphenyl)pyrimidin-4-ylamino]phenyl}ethanone, 6-(5-chloro-2-ethoxyphenyl)-N*4*-(4-chlorophenyl)-N*4*-methylpyrimidine-2,4-diamine, 1-(4-[2-amino-6-(5-chloro-2-methylphenyl)pyrimidin-4-ylamino]phenyl}ethanone, -6-(5-chloro-2-ethoxyphenyl)-N*4*-(4-methanesulfonylphenyl)pyrimidine-2,4-diamine, N*4*-(1H-Benzotriazol-5-yl)-6-(5-chloro-2-methylphenyl) pyrimidine-2,4-diamine, 6-(5-chloro-2-methylphenyl)-N*4*-(6-trifluoromethylpyridin-3-yl)pyrimidine-2,4-diamine, 1-{4-[2-amino-6-(5-bromo-2-ethoxyphenyl)pyrimidin-4-ylamino]phenyl}ethanone, 6-(5-bromo-2-ethoxyphenyl)-N*4*-(6-4*-(6-trifluoromethylpyridin-3-yl)-pyrimidine-2,4-diamine, 1-{4-[2-Amino-6-(5-bromo-2-ethoxy-phenyl)-pyrimidin-4-ylamino]-phenyl}-2,2,2-trifluoro-ethanol, 1-{4-[2-Amino-6-(5-bromo-2-ethoxy-phenyl)-pyrimidin-4-ylamino]-phenyl}-ethanone-oxime, 1-{4-[2-Amino-6-(5-bromo-2-ethoxy-phenyl)-pyrimidin-4-ylamino]-phenyl}-2,2,2-trifluoro-ethanone, 6-(5-Bromo-2-ethoxy-phenyl)-N*4*-(3,4-dimethyl-phenyl)-pyrimidine-2,4-diamine, 6-(5-Bromo-2-ethoxy-phenyl)-N*4*-(4-nitro-phenyl)-pyrimidine-2,4-diamine, 1-{4-[2-Amino-6-(5-bromo-2-ethoxy-phenyl)-N*4*-(3,4-dimethyl-phenyl)-pyrimidin-4-ylamino]-phenyl}-ethanol, 6-(5-Bromo-2-propoxy-phenyl)-N*4*-(4-chloro-phenyl)-pyrimidine-2,4-diamine, 6-(5-Bromo-2-isopropoxy-phenyl)-N*4*-(4-chloro-phenyl)-pyrimidine-2,4-diamine, 6-(5-Bromo-2-ethoxy-phenyl)-N*4*-[4-(1methoxy-ethyl)-phenyl]-pyrimidine-2,4-diamine, 3-[2-Amino-6-(5-Bromo-2-ethoxy-phenyl)-pyrimidin-4yl-amino]-benzamide, N*4*-{4-Azido-phenyl)-6-(2-ethoxy-5-iodo-phenyl)-pyrimidine-2,4-diamine, 2-{4-[2-Amino-6-(5-bromo-2-isopropoxy-phenyl)-pyrimidin-4-ylamino]-phenyl}-ethanol, 6-(5-Bromo-2-methoxy-phenyl)-N*4*-(4-chloro-phenyl)-pyrimidine-2,4-diamine, 6-[5-Bromo-2-(2-methoxy-ethoxy)-phenyl]-N*4*-(4-chloro-phenyl)-pyrimidine-2,4-diamine, 6-(5-Bromo-2-ethoxy-phenyl)-N*4*-quinolin-3-yl-pyrimidine-2,4-diamine, 6-(5-Bromo-2-hexyloxy-phenyl)-N*4*-(4-chloro-phenyl)-pyrimidine-2,4-diamine, 6-(2-Benzyloxy-5-bromo-phenyl)-N*4*-(4-chloro-phenyl)-pyrimidine-2,4-diamine, 1-{4-[2-Amino-6-(2,3,5-trichloro-phenyl)-pyrimidin-4-ylamino]-phenyl}-ethanone oxime, 6-(5-Bromo-2-butoxy-phenyl)-N*4*-(4-chloro-phenyl)-pyrimidine-2,4-diamine, 6-[5-Bromo-2-(2-morpholin-4-yl-ethoxy)-phenyl]-N*4*-(4-chloro-phenyl)-pyrimidine-2,4-diamine, 6-(5-Bromo-2-methoxy-phenyl)-N*4*-(4-trifluoromethyl-phenyl)-pyrimidine-2,4-diamine, 2-{4-[2-Amino-6-(5-bromo-2-methoxy-phenyl)-pyrimidin-4-ylamino]-phenyl}-ethanol, 6-(2-Benzyloxy-5-bromo-phenyl)-N*4*-(4-trifluoromethyl-phenyl)-pyrimidine-2,4-diamine, 1-{4-[2-Amino-6-(2,5-dichloro-phenyl)-pyrimidin-4-yl-amino]-phenyl}-ethanone oxime, 6-(2-Benzyloxy-5-chloro-phenyl)-N*4*-(4-chloro-phenyl)-pyrimidine-2,4-diamine, 6-[5-Bromo-2-(3-dimethylamino-propoxy)-phenyl]-N*4*-(4-chloro-phenyl)-pyrimidine-2,4-diamine, 6-(2-Benzyloxy-5-chloro-phenyl)-N*4*-(4-trifluoromethyl-phenyl)-pyrimidine-2,4-diamine, 2-{4-[2-Amino-6-(2-benzyloxy-5-chloro-phenyl)-pyrimidin-4-ylamino]-phenyl}-ethanol, 4-[2-Amino-6-(5-bromo-2-ethoxy-phenyl)-pyrimidin-4-ylamino]-phenyl-boronic acid, 4-[2-Amino-6-(5-bromo-2-methoxy-phenyl)-pyrimidin-4-ylamino]-benzonitrile, 6-(5-Bromo-2-methoxy-phenyl)-N*4*-(4-nitro-phenyl)-pyrimidine-2,4-diamine, 6-(5-Bromo-2-methoxy-phenyl)-N*4*-(4-bromo-phenyl)-pyrimidine-2,4-diamine, N*4*-(4-Bromo-phenyl)-6-(5-chloro-2-ethyl-phenyl)-pyrimidine-2,4-diamine, 6-(5-Chloro-2-ethyl-phenyl)-N*4*-(4-trifluoromethyl-phenyl)-pyrimidine-2,4-diamine, 6-[5-Bromo-2-(4-chloro-benzyloxy)-phenyl]-N*4*-(4-chloro-phenyl)-pyrimidine-2,4-diamine, 6-(5-Bromo-2-phenethyloxy-phenyl)-N*4*-(4-chloro-phenyl)-pyrimidine-2,4diamine, 6-(5-Chloro-2-ethyl-phenyl)-N*4*-(4-chloro-phenyl)-pyrimidine-2,4-diamine, 6-(5-Chloro-2-cyclohexylmethoxy-phenyl)-N*4*-(4-chloro-phenyl)-pyrimidine-2,4-diamine, 6-(5-Chloro-2-ethyl-phenyl)-N*4*-(4-nitro-phenyl)-pyrimidine-2,4-diamine, 3-[2-Amino-6-(2,5-dichloro-phenyl)-pyrimidin-4-ylamino]-benzoic acid ethyl ester, 3-[2-Amino-6-(5-bromo- 2-methoxy-phenyl)-pyrimidin-4-ylamino]-benzoic acid ethyl ester, (4-Bromo-phenyl)-[6-(5-chloro-2-methyl-phenyl)-pyrimidin-4-yl]-amine, 4-[2-Amino-6-(5-bromo-2-methyl-phenyl)-pyrimidin-4-ylamino]-phenyl-boronic acid, 6-(2-Allyloxy-5-chloro-phenyl)-N*4*-(4-chloro-phenyl)-pyrimidine-2,4-diamine, 2-{4-[2-amino-6-(5-chloro-2-ethyl-phenyl)-pyrimidin-4-ylamino]-phenyl}-ethanol, 2-(4-[6-(5-Chloro-2-methyl-phenyl)-pyrimidin-4-ylamino]-phenyl}-ethanol, 6-(2-Benzyloxy-5-bromo-phenyl)-N*4*-(4-nitro-phenyl)-pyrimidine-2,4-diamine, 6-[5-Bromo-2-(4-nitro-benzyloxy)-phenyl]-N*4*-(4-chloro-phenyl)-pyrimidine-2,4-diamine, N*4*-(4-Chloro-3-trifluoromethyl-phenyl)-6-(2,5-dichloro-phenyl)-pyrimidin-2,4-diamine, [6-(5-Bromo-2-ethoxy-phenyl)-pyrimidin-4-yl]-(4-trifluoromethyl-phenyl)-amine, [6-(5-Bromo-2-ethoxy-phenyl)-pyrimidin-4-yl]-(4-bromo-phenyl)-amine, 6-[5-Bromo-2-(2-methoxy-benzyloxy)-phenyl]N*4*-(4-chloro-phenyl)-pyrimidine-2,4-diamine, 4-[2-Amino-6-(5-bromo-2-ethoxy-phenyl)-pyrimidin-4-ylamino]-N-hydroxy-benzamide, 5-[2-Amino-6-(5-bromo-2-methoxy-phenyl)-pyrimidin-4-ylamino]-2-chloro-N-methyl-benzamide, 6-[5-Bromo-2-(4-methoxy-benzyloxy)-phenyl]-N*4*-(4-chloro-phenyl)-pyrimidine-2,4-diamine, 4-[2-Amino-6-(5-bromo-2-ethoxy-phenyl)-pyrimidin-4-ylamino]-benzamide, 6(5-Bromo-2-chloro-phenyl)-N*4*-(4-chloro-phenyl)-pyrimidine-2,4-diamine, 6-[5-Bromo-2-(2-methoxy-benzyloxy)-phenyl]-N*4*-p-tolyl-pyrimidine-2,4-diamine, 6-(5-Bromo-2-chloro-phenyl)-N*4*-(4-trifluoromethyl-phenyl)-pyrimidine-2,4-diamine, [6-(5-Bromo-2-ethoxy-phenyl)-pyrimidin-4-yl]-(4-chloro-phenyl)-amine, 2-{4-[6-(5-Bromo-2-ethoxy-phenyl)-pyrimidin-4-ylamino]-phenyl}-ethanol, [6-(5-Bromo-2-ethoxy-phenyl)-pyrimidin-4-yl]-(4-fluoro-phenyl)-amine, or physiologically acceptable salts thereof.

7. A pharmaceutical composition comprising a compound or salt thereof according to claim 1 in combination with a pharmaceutically acceptable carrier or diluent.

8. A pharmaceutical composition comprising a compound or salt thereof according to claim 2 in combination with a pharmaceutically acceptable carrier or diluent.

9. A pharmaceutical composition comprising a compound or salt thereof according to claim 3 in combination with a pharmaceutically acceptable carrier or diluent.

10. A pharmaceutical composition comprising a compound or salt thereof according to claim 4 in combination with a pharmaceutically acceptable carrier or diluent.

11. A pharmaceutical composition comprising a compound or salt thereof according to claim 5 in combination with a pharmaceutically acceptable carrier or diluent.

12. A pharmaceutical composition comprising a compound or salt thereof according to claim 6 in combination with a pharmaceutically acceptable carrier or diluent.

* * * * *

SEQUENCE LISTING

```
<160> NUMBER OF SEQ ID NOS: 3

<210> SEQ ID NO 1
<211> LENGTH: 39
<212> TYPE: DNA
<213> ORGANISM: Artificial Sequence
<220> FEATURE:
<223> OTHER INFORMATION: Primer

<400> SEQUENCE: 1
tgatatccga agaagatctt atggagctgt ggccgtgtc                             39

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
caggctctag actactgggc cggctgcac                                        29

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
cctacgtcga catggaacaa aaattgatat ccgaagaaga tc                         42
```